US012727793B2

(12) United States Patent
Fernandez de Avila et al.

(10) Patent No.: US 12,727,793 B2
(45) Date of Patent: Sep. 8, 2026

(54) DEVICES AND METHODS FOR MEASURING A CONCENTRATION OF A TARGET ANALYTE IN A BIOLOGICAL FLUID IN VIVO

(71) Applicant: DexCom, Inc., San Diego, CA (US)

(72) Inventors: Berta Esteban Fernandez de Avila, San Diego, CA (US); Devon M. Headen, San Diego, CA (US); Stacy Hunt DuVall, San Diego, CA (US); Jiong Zou, San Diego, CA (US); Shane Richard Parnell, San Diego, CA (US); Nicholas Vincent Apollo, San Diego, CA (US); Joshua Ray Windmiller, San Diego, CA (US)

(73) Assignee: DEXCOM, INC., San Diego, CA (US)

( * ) Notice: Subject to any disclaimer, the term of this patent is extended or adjusted under 35 U.S.C. 154(b) by 81 days.

(21) Appl. No.: 18/241,658

(22) Filed: Sep. 1, 2023

(65) Prior Publication Data

US 2024/0074682 A1 Mar. 7, 2024

Related U.S. Application Data

(60) Provisional application No. 63/403,568, filed on Sep. 2, 2022, provisional application No. 63/403,582, filed on Sep. 2, 2022.

(51) Int. Cl.
*A61B 5/145* (2006.01)
*A61B 5/00* (2006.01)
(Continued)

(52) U.S. Cl.
CPC ...... *A61B 5/14546* (2013.01); *A61B 5/14865* (2013.01); *A61B 5/318* (2021.01); *A61B 5/6847* (2013.01)

(58) Field of Classification Search
CPC . A61B 5/14546; A61B 5/14865; A61B 5/318; A61B 5/6847; A61B 5/0031;
(Continued)

(56) References Cited

U.S. PATENT DOCUMENTS 5,225,064 A 7/1993 Henkens et al.
5,866,353 A 2/1999 Berneth et al.
(Continued)

FOREIGN PATENT DOCUMENTS

EP 0300082 A2 1/1989
EP 3492014 B1 10/2022
(Continued)

OTHER PUBLICATIONS

Wang et al. , All-solid-state blood calcium sensors based on screen-printed poly(3,4-ethylenedioxythiophene) as the solid contact, Sensors and Actuators B, 2012, 173, 630-635 (Year: 2012).*
(Continued)

*Primary Examiner* — Shizhi Qian
(74) *Attorney, Agent, or Firm* — Christopher J. Knors; Moore & Van Allen PLLC

(57) ABSTRACT

Devices and methods for measuring a concentration of a target analyte in a biological fluid in vivo are provided herein. In some examples, a device includes an indwelling sensor and sensor electronics. The sensor may include a substrate; a first electrode disposed on the substrate; an ionophore disposed on the substrate to selectively transport the target ion to or within the first electrode; and a second electrode disposed on the substrate. The sensor electronics is configured to generate a signal corresponding to an electromotive force which is at least partially based on a potential difference that is generated between the first electrode and the second electrode responsive to the ionophore transporting the target ion to the first electrode.

15 Claims, 33 Drawing Sheets

(51) Int. Cl.
*A61B 5/1486* (2006.01)
*A61B 5/318* (2021.01)

(58) Field of Classification Search
CPC ... A61B 5/02438; A61B 5/0245; A61B 5/145; A61B 5/14507; A61B 5/14539; A61B 5/1473; A61B 5/287; A61B 5/316; A61B 5/7257; A61B 5/14532; G01N 27/3335
See application file for complete search history.

(56) References Cited

U.S. PATENT DOCUMENTS 6,134,461 A 10/2000 Say et al.
6,605,200 B1 8/2003 Mao et al.
6,605,201 B1 8/2003 Mao et al.
6,736,957 B1 5/2004 Forrow et al.
7,018,518 B2 3/2006 Willner et al.
7,485,212 B2 2/2009 Willner et al.
7,501,053 B2 3/2009 Karinka et al.
7,754,093 B2 7/2010 Forrow et al.
8,268,143 B2 9/2012 Liu et al.
8,444,834 B2 5/2013 Liu et al.
10,852,268 B2 12/2020 Hahn et al.
11,235,163 B2 2/2022 Huelskamp et al.
11,253,184 B2 2/2022 Shute et al.
11,253,190 B2 2/2022 Ortiz et al.
11,278,218 B2 3/2022 Guy et al.
11,278,219 B2 3/2022 Gassler et al.
11,298,068 B2 4/2022 Perschbacher et al.
11,331,009 B2 5/2022 Ionescu et al.
11,331,018 B2 5/2022 Rice et al.
11,338,135 B2 5/2022 Schmidt et al.
11,344,230 B2 5/2022 Coppedèet al.
11,382,539 B2 7/2022 Brister et al.
11,389,087 B2 7/2022 Nyberg et al.
11,389,112 B1 7/2022 Miller et al.
11,389,140 B2 7/2022 Pizer et al.
11,395,868 B2 7/2022 Roettger et al.
11,412,938 B2 8/2022 LeBoeuf et al.
11,412,962 B1 8/2022 Miller et al.
11,412,980 B2 8/2022 Miller et al.
11,439,304 B2 9/2022 Stahmann et al.
11,471,099 B2 10/2022 Burnes et al.
11,478,201 B2 10/2022 Kharam et al.
11,480,561 B2 10/2022 Wen et al.
11,490,809 B2 11/2022 Krueger
11,504,537 B2 11/2022 Perschbacher et al.
11,540,752 B1 1/2023 Miller et al.
11,545,015 B1 1/2023 Lee et al.
11,583,196 B2 2/2023 Shute et al.
11,627,900 B2 4/2023 Simpson et al.
11,636,950 B2 4/2023 Kazar
11,649,353 B2 5/2023 Al-Rashid et al.
11,666,216 B2 6/2023 Scherer et al.
11,684,272 B2 6/2023 Thakur et al.
11,691,006 B2 7/2023 Schmidt et al.
11,717,232 B1 8/2023 Miller et al.
11,723,544 B2 8/2023 Wariar et al.
11,723,545 B2 8/2023 Thakur et al.
11,737,694 B2 8/2023 Phan et al.
11,751,812 B2 9/2023 Linder et al.
11,759,557 B2 9/2023 Gerber et al.
11,786,126 B2 10/2023 Hunter et al.
11,806,142 B2 11/2023 Schibli et al.
11,819,650 B2 11/2023 Pushpala et al.
11,831,594 B2 11/2023 Jackson et al.
11,832,968 B2 12/2023 Perschbacher et al.
11,832,970 B2 12/2023 An et al.
11,864,891 B2 1/2024 Boock et al.
11,865,241 B2 1/2024 Elbadry et al.
11,867,652 B2 1/2024 Hoss et al.
11,867,655 B2 1/2024 Lillehoj et al.
11,872,034 B2 1/2024 Escobar et al.
11,872,036 B2 1/2024 Polytaridis et al.
11,877,821 B2 1/2024 Tran
11,887,467 B1 1/2024 Lee et al.
2009/0266719 A1* 10/2009 Hsiung .................. C12Q 1/002 204/403.1
2012/0197231 A1* 8/2012 Kane .................. A61B 5/14546 607/18
2013/0284609 A1 10/2013 Liu et al.
2016/0374597 A1* 12/2016 Stahmann .......... A61B 5/14503 600/309
2017/0188916 A1* 7/2017 Wang .................. C12N 11/093
2019/0167163 A1 6/2019 Simpson et al.
2020/0072782 A1* 3/2020 Hahn ................. A61B 5/14532
2020/0085341 A1* 3/2020 Windmiller ......... A61M 5/1723
2020/0237275 A1 7/2020 Feldman et al.
2020/0237276 A1 7/2020 Oja et al.
2020/0237277 A1 7/2020 Ouyang et al.
2020/0241015 A1 7/2020 Ouyang et al.
2021/0379370 A1 12/2021 Windmiller et al.
2022/0031204 A1 2/2022 Sonkusale et al.
2022/0039699 A1 2/2022 Esenaliev
2022/0047193 A1 2/2022 Yang et al.
2022/0047217 A1 2/2022 Mayo et al.
2022/0056500 A1 2/2022 Ouyang et al.
2022/0062607 A1 3/2022 Davis et al.
2022/0092526 A1 3/2022 Dalforno et al.
2022/0095968 A1 3/2022 Wang et al.
2022/0095983 A1 3/2022 Mahajan et al.
2022/0096020 A1 3/2022 Ahmed et al.
2022/0104773 A1 4/2022 Lee et al.
2022/0117503 A1 4/2022 Wang et al.
2022/0125384 A1 4/2022 Shute et al.
2022/0133178 A1 5/2022 Li et al.
2022/0133234 A1 5/2022 Li et al.
2022/0150308 A1 5/2022 Hua et al.
2022/0151558 A1 5/2022 Pushpala et al.
2022/0160265 A1 5/2022 Sankhala et al.
2022/0160280 A1 5/2022 Toyota
2022/0160298 A1 5/2022 Panneer Selvam et al.
2022/0167857 A1 6/2022 Lin
2022/0167867 A1 6/2022 Hunter
2022/0176088 A1 6/2022 Salahieh et al.
2022/0192547 A1 6/2022 Liang et al.
2022/0192552 A1 6/2022 Feldman
2022/0192597 A1 6/2022 Feldman
2022/0194644 A1 6/2022 Grucela et al.
2022/0211614 A1 7/2022 Welch et al.
2022/0233107 A1 7/2022 Pushpala et al.
2022/0255356 A1 8/2022 Tseng et al.
2022/0263904 A1 8/2022 Hua et al.
2022/0265173 A1 8/2022 Zhong et al.
2022/0265180 A1 8/2022 Choi et al.
2022/0265224 A1 8/2022 Hauptman et al.
2022/0273196 A1 9/2022 Jones et al.
2022/0280095 A1 9/2022 Perschbacher et al.
2022/0323006 A1 10/2022 Conia et al.
2022/0334077 A1* 10/2022 Uchiyama ............ G01N 27/301
2022/0346675 A1 11/2022 Nyberg et al.
2022/0346759 A1 11/2022 Pizer et al.
2022/0369961 A1 11/2022 Mothilal et al.
2022/0378337 A1 12/2022 Vanslyke et al.
2022/0386961 A1 12/2022 Mitchell et al.
2022/0412914 A1 12/2022 Hagen et al.
2023/0023786 A1* 1/2023 Crespo Paravano ........................ A61B 5/14514
2023/0027200 A1 1/2023 Pal et al.
2023/0028745 A1 1/2023 Al-Ali et al.
2023/0029042 A1 1/2023 Facteau et al.
2023/0033467 A1 2/2023 Pushpala et al.
2023/0051289 A1 2/2023 Pai et al.
2023/0064744 A1 3/2023 Epstein et al.
2023/0073214 A1 3/2023 Wang et al.
2023/0082672 A1 3/2023 Weinstein et al.
2023/0097649 A1 3/2023 An et al.
2023/0099851 A1 3/2023 Cole
2023/0101926 A1 3/2023 Karmon
2023/0103473 A1 4/2023 Thakur et al.
2023/0105123 A1 4/2023 Thakur et al.
2023/0107996 A1 4/2023 Mahajan et al.
2023/0109023 A1 4/2023 Park et al.
2023/0113175 A1 4/2023 Garai et al.

(56) References Cited

U.S. PATENT DOCUMENTS

2023/0113717 A1 4/2023 Poudineh et al.
2023/0122366 A1 4/2023 Thakur et al.
2023/0129902 A1 4/2023 Park et al.
2023/0133195 A1 5/2023 Diener et al.
2023/0134919 A1 5/2023 Dowd et al.
2023/0135175 A1 5/2023 Jepson et al.
2023/0136188 A1 5/2023 Pickus et al.
2023/0138673 A1 5/2023 Crawford et al.
2023/0140143 A1 5/2023 Acciaroli et al.
2023/0148920 A1 5/2023 Harley-Trochimczyk et al.
2023/0157640 A1 5/2023 Weber et al.
2023/0170083 A1 6/2023 Davis et al.
2023/0181094 A1 6/2023 Osorio
2023/0190178 A1 6/2023 Even et al.
2023/0200710 A1 6/2023 Thakur et al.
2023/0200752 A1 6/2023 Reihman et al.
2023/0210414 A1 7/2023 Connell
2023/0210415 A1 7/2023 Ou et al.
2023/0211341 A1 7/2023 Dalton et al.
2023/0218229 A1 7/2023 Curran et al.
2023/0218894 A1 7/2023 Arnholt et al.
2023/0263479 A1 8/2023 Johnson et al.
2023/0270362 A1 8/2023 Ordonez Orellana et al.
2023/0277762 A1 9/2023 Duhamel et al.
2023/0293009 A1 9/2023 Barreras et al.
2023/0293058 A1 9/2023 Rong et al.
2023/0293060 A1 9/2023 Duvall et al.
2023/0301553 A1 9/2023 Rong et al.
2023/0301563 A1 9/2023 Simpson et al.
2023/0307123 A1 9/2023 LeBoeuf et al.
2023/0309873 A1 10/2023 Brancazio
2023/0309881 A1 10/2023 Simpson et al.
2023/0314340 A1 10/2023 Wang et al.
2023/0320661 A1 10/2023 Chickering, III et al.
2023/0329567 A1 10/2023 Courtine et al.
2023/0346274 A1 11/2023 Wang et al.
2023/0369749 A1 11/2023 Zhao
2023/0380729 A1 11/2023 Kamath et al.
2023/0389844 A1 12/2023 Johnson et al.
2023/0404446 A1 12/2023 Hahn et al.
2023/0404662 A1 12/2023 Wu et al.
2023/0414140 A1 12/2023 Li et al.
2024/0008770 A1 1/2024 Koehler et al.
2024/0013924 A1 1/2024 Rajan et al.
2024/0017081 A1 1/2024 Mahajan et al.
2024/0021284 A1 1/2024 Paul et al.
2024/0022636 A1 1/2024 Kanteti et al.
2024/0023849 A1 1/2024 Pesantez et al.
2024/0040348 A1 2/2024 Hua et al.

FOREIGN PATENT DOCUMENTS

EP 3440999 B1 3/2023
EP 4287938 A1 12/2023
EP 4297646 A1 1/2024
EP 4306041 A1 1/2024
WO 03019170 A1 3/2003
WO 2017008816 A1 1/2017
WO 2020046888 A1 3/2020
WO 2022106542 A1 5/2022
WO 2022133308 A1 6/2022
WO 2022133313 A1 6/2022
WO 2022170361 A1 8/2022
WO 2022180184 A1 9/2022
WO 2022245804 A1 11/2022
WO 2022246983 A1 12/2022
WO 2022263992 A1 12/2022
WO 2023031047 A1 3/2023
WO 2023031069 A1 3/2023
WO 2023034934 A1 3/2023
WO 2023043908 A1 3/2023
WO 2023049711 A1 3/2023
WO 2023059374 A1 4/2023
WO 2023097765 A1 6/2023
WO 2023107107 A1 6/2023
WO 2023137008 A1 7/2023
WO 2023152411 A1 8/2023
WO 2023156516 A1 8/2023
WO 2023197039 A1 10/2023
WO 2023199322 A1 10/2023
WO 2023205274 A1 10/2023
WO 2023247956 A1 12/2023
WO 2024019968 A1 1/2024
WO 2024020000 A1 1/2024
WO 2024022733 A1 2/2024

OTHER PUBLICATIONS

Lyu et al., Solid-contact ion-selective electrodes: response mechanisms, transducer materials and wearable sensors, Membrane, 2020, 10, 128 (Year: 2020).*

Komaba et al., All-solid-state ion-selective electrodes with redox-active lithium, sodium, and potassium insertion materials as the inner solid-contact layers, Analyst, 2017, 142, 3857 (Year: 2017).*

Huang et al., Highly sensing and transducing materials for potentiometric ion sensors with versatile applicability, Progress in Materials Science, 2022, 125, 100885 (Year: 2022).*

Joon et al., PVC-based ion-selective electrodes with a silicone rubber outer coating with improved analytical performance, Analytical Chemistry, 2019, 91, 10524-10531 (Year: 2019).*

Kwon et al., An all-solid-state reference electrode based on the layer-by-layer polymer coating, Analyst, 2007, 132, 906-912 (Year: 2007).*

Li et al., Microneedle-Based Potentiometric Sensing System for Continuous Monitoring of Multiple Electrolytes in Skin Interstitial Fluids, ACS sensors, 2021, 6, 2181-2190 (Year: 2021).*

Li et al., Supporting Information of Microneedle-Based Potentiometric Sensing System for Continuous Monitoring of Multiple Electrolytes in Skin Interstitial Fluids, ACS sensors, 2021, 6, 2181-2190 (Year: 2021).*

Pansodtee et al., The multi-channel potentiostat: Development and evaluation of a scalable mini-potentiostat array for investigating electrochemical reaction mechanisms, Plos One, 2021, 16(9), e0257167 (Year: 2021).*

Canovas R., et al., "Cytotoxicity Study of Ionophore-Based Membranes: Toward On-Body and in Vivo Ion Sensing," ACS Sensors, Aug. 26, 2019, vol. 04, No. 09, pp. 2524-2535.

Chen X.V., et al., "Ion-Selective Potentiometric Sensors with Silicone Sensing Membranes: A Review," Current Opinion in Electrochemistry, Apr. 2022, vol. 32, 61 pages.

International Search Report and Written Opinion for Application No. PCT/US2023/03190, mailed Jan. 23, 2024, 23 pages.

Lyu Y., et al., "Solid-contact Ion-selective Electrodes: Response Mechanisms, Transducer Materials and Wearable Sensors", Membranes, vol. 10(6), Jun. 23, 2020, 24 pages, XP055777944, DOI: 10.3390/membranes10060128.

Qi L., et al.,"Polymeric Membrane Ion-selective Electrodes with Anti-biofouling Properties by Surface Modification of Silver Nanoparticles", Sensors and Actuators B: Chemical, vol. 328, Oct. 7, 2020, XP086398046, ISSN: 0925-4005, DOI: 10.1016/J.SNB.2020.129014.

Wang C., et al., "Integrated Multi-ISE Arrays with Improved Sensitivity, Accuracy and Precision," Scientific Reports, Mar. 17, 2017, vol. 07, 10 pages.

* cited by examiner

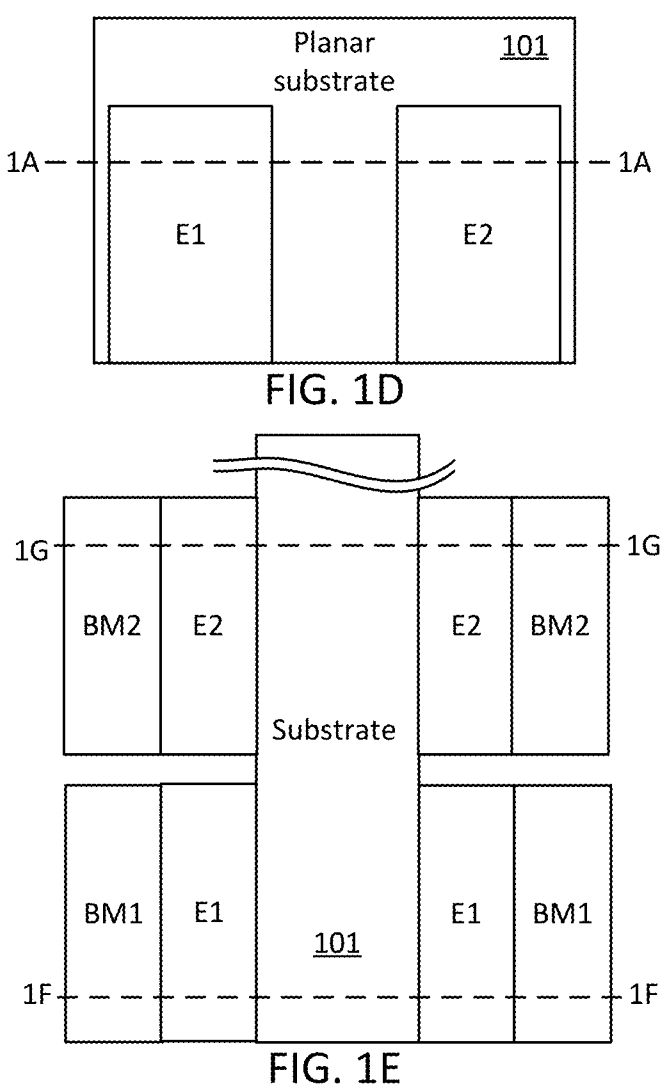
FIG. 1D
FIG. 1E
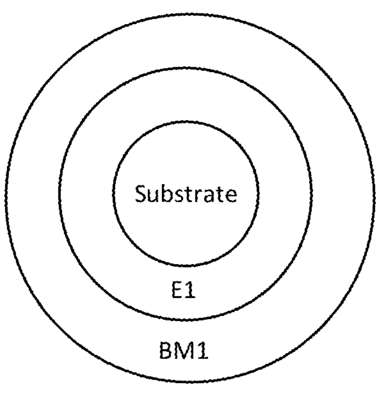
FIG. 1F
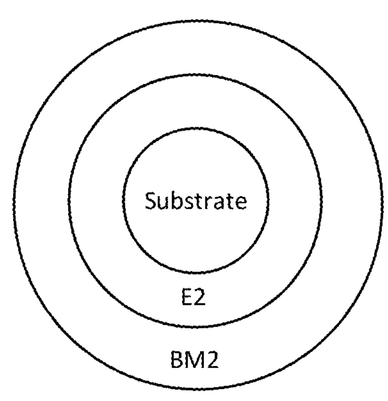
FIG. 1G

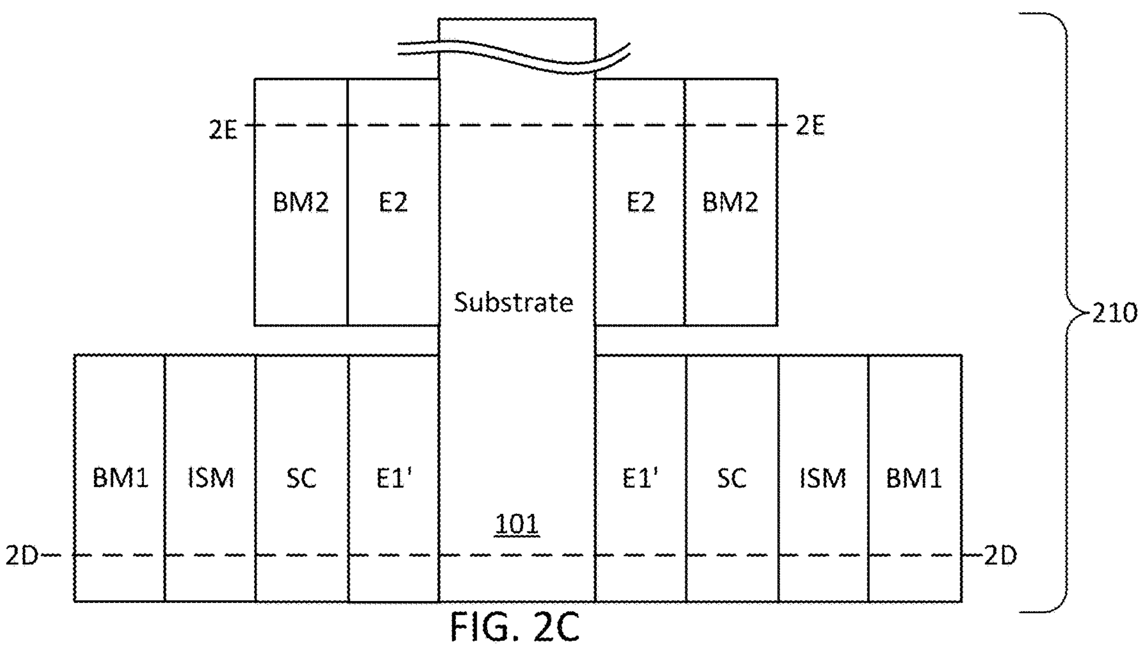
FIG. 2C
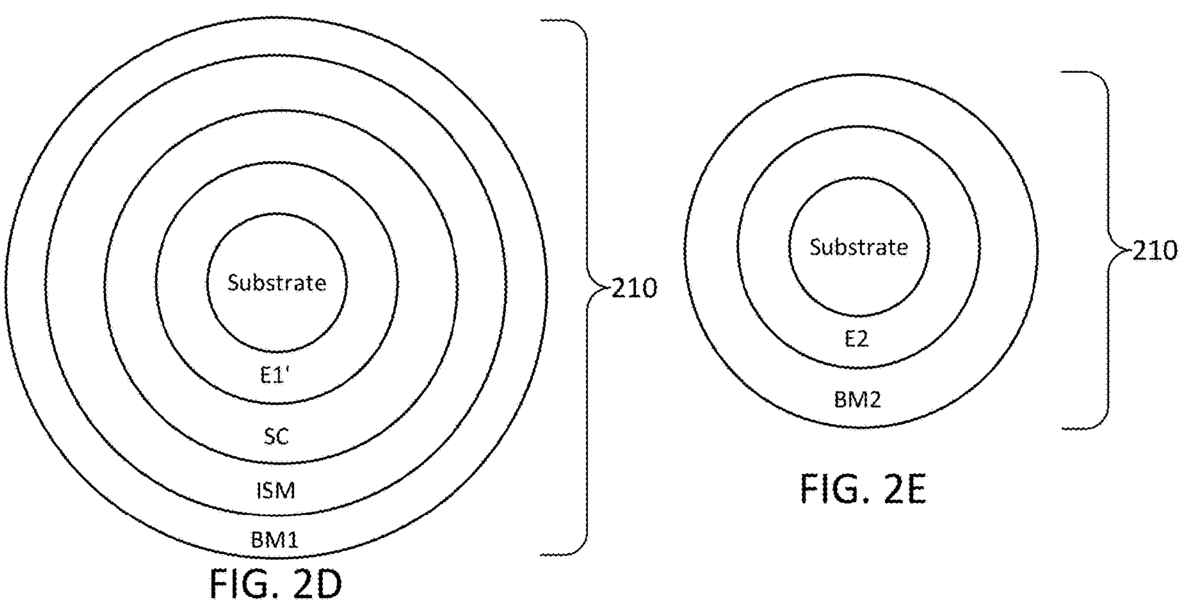
FIG. 2D
FIG. 2E

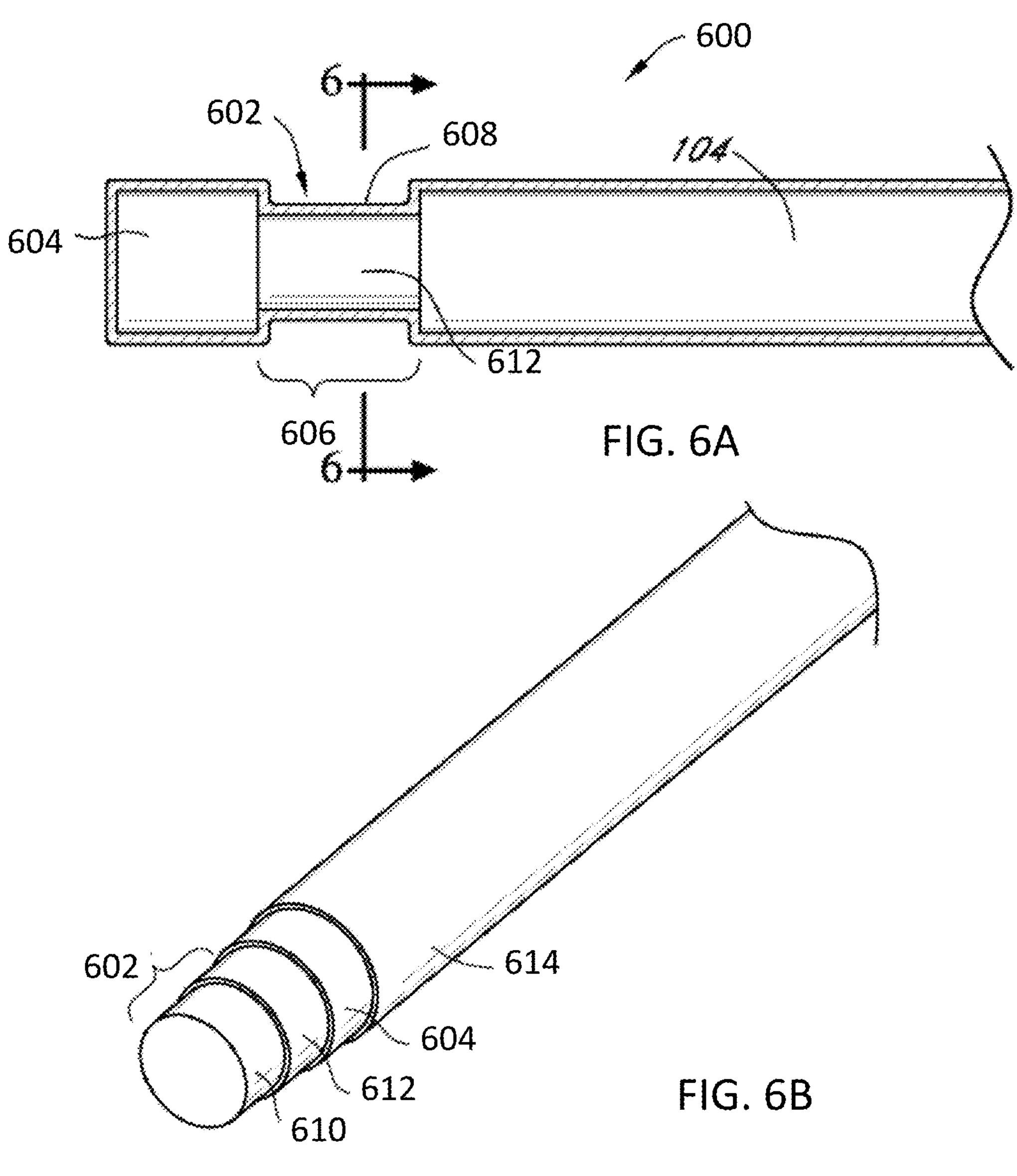
FIG. 6A
FIG. 6B
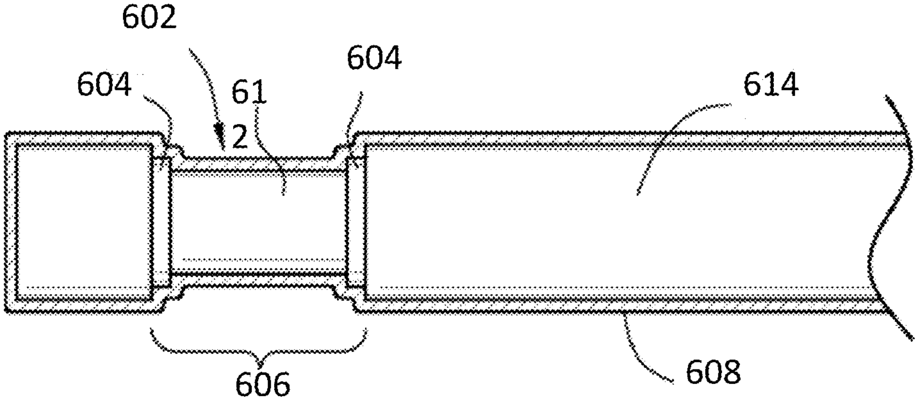
FIG. 6C

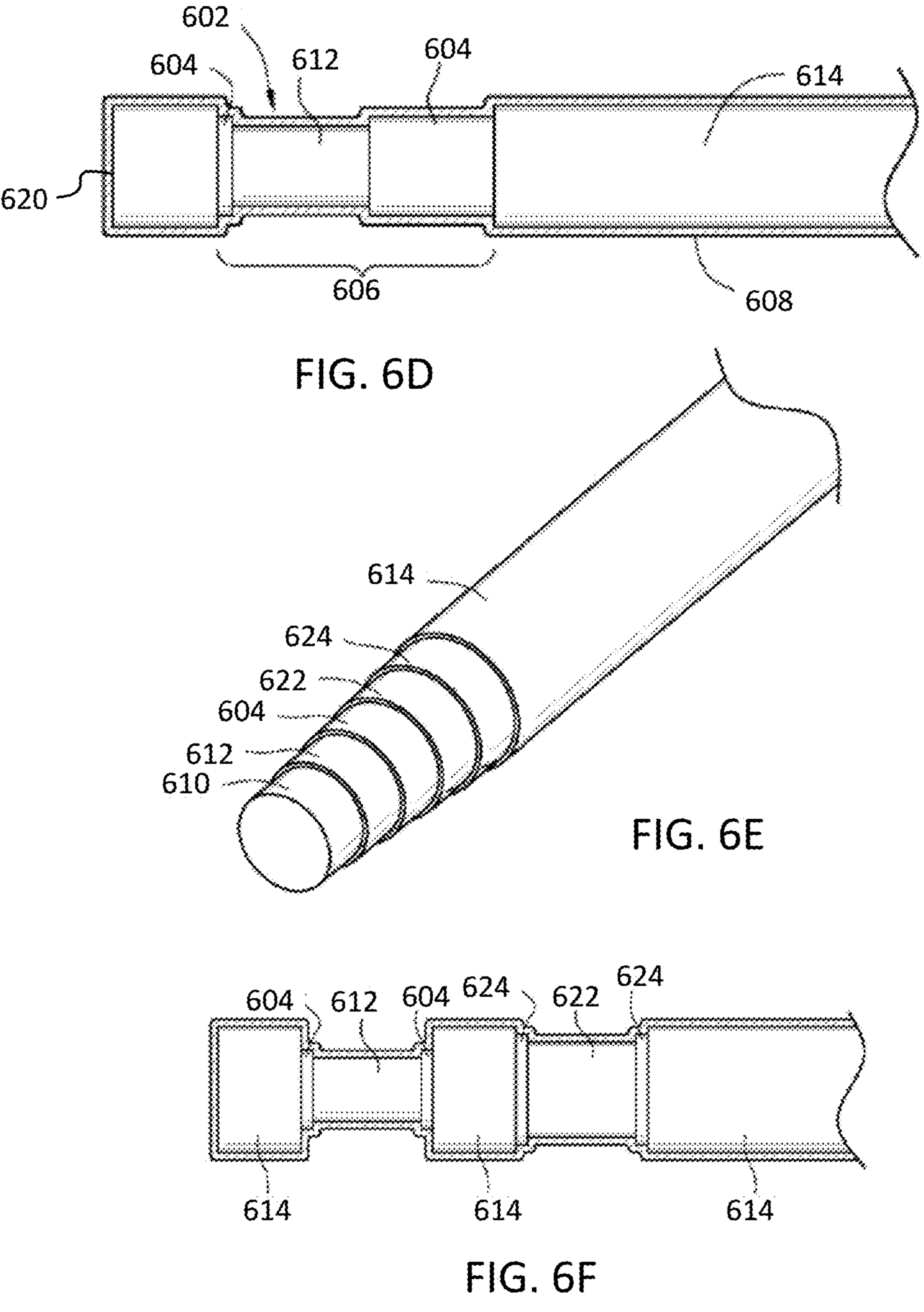
FIG. 6D
FIG. 6E
FIG. 6F
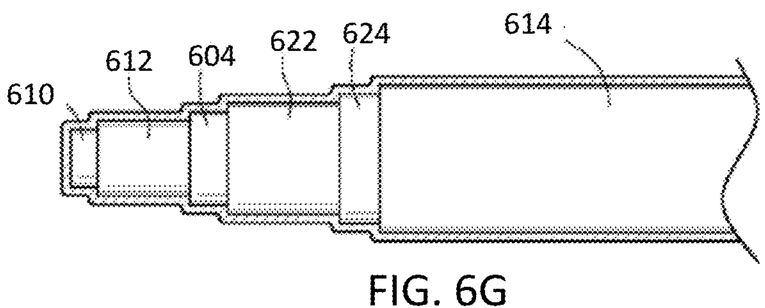
FIG. 6G

DEVICES AND METHODS FOR MEASURING A CONCENTRATION OF A TARGET ANALYTE IN A BIOLOGICAL FLUID IN VIVO

CROSS-REFERENCE TO RELATED APPLICATIONS

This application claims the benefit of U.S. Provisional Application No. 63/403,582 filed on Sep. 2, 2022, and U.S. Provisional Application No. 63/403,568 filed on Sep. 2, 2022, the entirety of each of which is incorporated herein by reference.

TECHNICAL FIELD

This application generally relates to measuring concentration of an analyte in a biological fluid. This also application generally relates to measuring an electrophysiological signal.

BACKGROUND

The concentration of an ion, such as sodium, potassium, magnesium, calcium, or ammonium, in a host's biological fluid can provide important information about that host's health status. Illustratively, the potassium ion ($K^+$) is a biomarker of cardiovascular disease. In another example, the potassium ion ($K^+$) is a biomarker of kidney disease. Indeed, in the US, about 14.8M individuals with diabetes are diagnosed with kidney disease, for example, impaired renal function; these patients may benefit from frequent measurement of blood potassium to assess kidney function and guide therapies, which may include oral medications, at one end of the spectrum, to dialysis on the other. In yet another example, the potassium ion ($K^+$) is a biomarker of both cardiovascular disease and kidney disease.

Further, about 9M individuals in the US have both diabetes and cardiac arrythmia. Cardiac arrythmia is largely caused by improper potentiation of the myocardium; potassium helps to control and moderate the electrical signals of the myocardium. Untreated, cardiac arrythmia can progress into ventricular fibrillation and sudden cardiac death. Accordingly, it would be useful to have a rapid, robust, and convenient way to monitor the concentration of an ion in the host's biological fluid.

Electrophysiological signals, such as heartbeat, can provide important information about a host's health status. Accordingly, it would be useful to have a rapid, robust, and convenient way to monitor one or more of such electrophysiological signals.

SUMMARY

Devices and methods for measuring an electrophysiological signal and/or a concentration of a target analyte in a biological fluid in vivo are provided herein.

Some examples herein provide a device for continuously measuring a concentration of a target ion in a biological fluid in vivo. The device may include an indwelling analyte sensor, including a substrate; a first electrode disposed on the substrate; an ionophore disposed on the substrate and configured to selectively transport the target ion to or within the first electrode; and a second electrode disposed on the substrate. The device may include sensor electronics configured to generate a signal corresponding to an electromotive force, the electromotive force being at least partially based on a potential difference that is generated between the first electrode and the second electrode responsive to the ionophore transporting the target ion to the first electrode.

In some examples, the sensor electronics further is configured to use the signal to generate an output corresponding to a measurement of the concentration of the target ion in the biological fluid.

In some examples, the sensor electronics further is configured to transmit the signal to an external device configured to use the signal to generate an output corresponding to a measurement of the concentration of the target ion in the biological fluid.

In some examples, the first electrode includes a polymer having the ionophore therein. In some examples, the first electrode includes a conductive polymer having the ionophore therein. In some examples, the first electrode substantially excludes any plasticizer. In some examples, the first electrode consists essentially of the conductive polymer and the ionophore. In some examples, the first electrode consists essentially of the conductive polymer, the ionophore, and an additive with ion exchanger capability. In some examples, the additive includes a lipophilic salt. In some examples, the lipophilic salt is selected from the group consisting of sodium tetrakis[3,5-bis(trifluoromethyl)phenyl]borate (NaTPFB), sodium tetraphenylborate (NaTPB), potassium tetrakis [3,5-bis(trifluoromethyl)phenyl]borate (KTFPB), and potassium tetrakis(4-chlorophenyl)borate (KTClPB). In some examples, the lipophilic salt additive is present in an amount of about 0.01 to about 1 weight percent in the polymer.

In some examples, the conductive polymer is present in an amount of about 90 to about 99.5 weight percent. In some examples, the conductive polymer is selected from the group consisting of: poly(3,4-ethylenedioxythiophene) (PEDOT), poly(3,4-ethylenedioxythiophene) polystyrene sulfonate (PEDOT:PSS), polyaniline (PANI), poly(pyrrole) (PPy), or poly(3-octylthiophene) (POT). In some examples, the ionophore is present in an amount of about 0.01 to about 10 weight percent, about 0.2 to about 10 weight percent, or about 0.5 to about 10 weight percent in the conductive polymer.

In some examples, the ion-selective membrane (ISM) is a polymer. In one example, the ion-selective membrane is a fluorosilicone rubber, a polydimethylsiloxane polymer, a silicone rubber, a polyurethane with a polysiloxane soft segment, a polyurethane with a hard segment and a soft segment, e.g., polyether or polycarbonate or polydimethylsiloxane soft segment, a water-based polyurethane, polyvinyl butyral, polymethylmethacrylate, polyvinyl acrylate, or blends or graft polymers thereof.

In some examples, the ionophore is within an ion-selective membrane disposed on the first electrode. In some examples, the ion-selective membrane substantially excludes any phthalate, sebacate, nitrophenyl ether and fluorophenyl nitrophenyl ether plasticizers plasticizer. In some examples, the ion-selective membrane substantially excludes any plasticizer. In some examples, the ion-selective membrane consists essentially of a biocompatible polymer and an ionophore configured to selectively bind the target ion.

In some examples, the ion-selective membrane consists essentially of a biocompatible polymer, an ionophore configured to selectively bind the target ion, and an additive with ion exchanger capability, e.g., the ability to exchange ions. In some examples, the additive includes a lipophilic salt. In some examples, the lipophilic salt is selected from the group consisting of sodium tetrakis[3,5-bis(trifluoromethyl)phenyl]borate (NaTPFB), sodium tetraphenylborate (NaTPB), potassium tetrakis [3,5-bis(trifluoromethyl)phenyl]borate (KTFPB), and potassium tetrakis(4-chlorophenyl)borate (KTClPB). In some examples, the additive is present in an amount of about 0.01 to about 1 weight percent in the ion-selective membrane.

In some examples, the biocompatible polymer is present in an amount of about 90 to about 99.5 weight percent in the ion-selective membrane. In some examples, the biocompatible polymer includes a hydrophobic polymer. In some examples, the hydrophobic polymer is selected from the group consisting of silicone, fluorosilicone (FS), polyurethane, fluoropolymer, poly(vinyl chloride) (PVC), polyacrylate, and polymethacrylate. In some examples, the biocompatible polymer includes a block copolymer. In some examples, the block copolymer includes a hydrophilic block selected from the group consisting of polycarbonate (PC) and polybutadiene (PBD). In some examples, the block copolymer includes a hydrophobic group selected from the group consisting of polydimethylsiloxane (PDMS), methylene diphenyl diisocyanate (MDI), polysulfone (PSF), and methyl methacrylate (MMA). In some examples, the ionophore is present in an amount of about 0.5 to about 10 weight percent in the ion-selective membrane.

In some examples, the first electrode includes a metal, a metal alloy, a transition metal oxide, a transparent conductive oxide, a carbon material, a doped semiconductor, a binary semiconductor, a ternary semiconductor, or a conductive polymer. In some examples, the metal is selected from the group consisting of: gold, platinum, silver, iridium, rhodium, ruthenium, nickel, chromium, and titanium. In some examples, the metal is oxidized or in the form of a metal salt. In some examples, the carbon material is selected from the group consisting of: carbon paste, graphene oxide, reduced graphene oxide, carbon nanotubes, C60, porous carbon nanomaterial, mesoporous carbon, glassy carbon, hybrid carbon nanomaterial, graphite, and doped diamond. In some examples, the doped semiconductor, binary semiconductor, or ternary semiconductor is selected from the group consisting of: p- or n-doped silicon, germanium, silicon-germanium, zinc oxide, gallium arsenide, indium phosphide, gallium nitride, cadmium telluride, indium gallium arsenide, and aluminum arsenide. In some examples, the conductive polymer is selected from the group consisting of: poly(3,4-ethylenedioxythiophene) (PEDOT), poly(3,4-ethylenedioxythiophene) polystyrene sulfonate (PEDOT:PSS), polyaniline (PANI), poly(pyrrole) (PPy), or poly(3-octylthiophene) (POT).

In some examples, the ion-selective membrane is in direct contact with at least a portion of the first electrode. In some examples, the ion-selective membrane is in direct contact with at least a majority of a surface area of the first electrode.

In some examples, the ion-selective membrane is in indirect contact with at least a portion of the first electrode, for example, a solid contact layer is disposed between the first electrode and the ion-selective membrane. In some examples, at least a portion of the solid contact layer is electrically coupled to the first electrode and/or in direct electrical communication with the first electrode. In some examples, the solid contact layer includes a metal, a carbon material, a doped semiconductor, or a conductive polymer. In some examples, the metal is selected from the group consisting of: gold, platinum, silver, iridium, rhodium, ruthenium, nickel, chromium, and titanium. In some examples, the metal is oxidized or in the form of a metal salt. In some examples, the metal displays a nanostructured surface. In some examples, the carbon material is selected from the group consisting of: carbon paste, graphene oxide, reduced graphene oxide, carbon nanotubes, C60, porous carbon nanomaterial, mesoporous carbon, glassy carbon, hybrid carbon nanomaterial, graphite, and doped diamond. In some examples, the doped semiconductor is selected from the group consisting of: p- or n-doped silicon, germanium, silicon-germanium, zinc oxide, gallium arsenide, indium phosphide, gallium nitride, cadmium telluride, indium gallium arsenide, and aluminum arsenide. In some examples, the conductive polymer is selected from the group consisting of: poly(3,4-ethylenedioxythiophene) (PEDOT), poly(3,4-ethylenedioxythiophene) polystyrene sulfonate (PEDOT:PSS), polyaniline (PANI), poly(pyrrole) (PPy), or poly(3-octylthiophene) (POT). In some examples, the solid contact layer includes a redox couple. In some examples, the redox couple includes two or more metallic centers (e.g., metal cations) with different oxidation states. In some examples, the two or more metallic centers are both transition metals. In some examples, the metallic centers are selected from the group consisting of Co(II) and Co(III); Ir(II) and Ir(III); and Os(II) and Os(III). In some examples, the solid contact layer includes a mixed conductor, or mixed ion-electron conductor. In some examples, the solid contact layer includes a compound selected from the group consisting of strontium titanate ($SrTiO_3$), titanium dioxide ($TiO_2$), (La,Ba,Sr)(Mn,Fe,Co)$O_{3-d}$,$La_2CuO_{4+d}$, cerium(IV) oxide ($CeO_2$), lithium iron phosphate ($LiFePO_4$), and $LiMnPO_4$. In some examples, the solid contact layer inhibits transport of water from the biological fluid to the first electrode. In some examples, the solid contact layer is configured to enhance electrical stability of the first electrode.

In some examples, the target ion is selected from the group consisting of sodium, potassium, hydrogen, lithium, magnesium, calcium, chloride, sulfite, sulfate, phosphate and ammonium. In some examples, the target ion is sodium, and the ionophore is 4-tert-butylcalix[4]arene-tetraacetic acid tetraethyl ester (sodium ionophore X) or calix[4]arene-25,26,27,28-tetrol (calix[4]arene). In some examples, the target ion is potassium, and the ionophore is potassium ionophore I (valinomycin), potassium ionophore II: bis[(benzo-15-crown-5)-4'-ylmethyl] pimelate (BB15C5); potassium ionophore III: or 2-dodecyl-2-methyl-1,3-propanediyl bis[N-[5'-nitro(benzo-15-crown-5)-4'-yl]carbamate] (BME44). In some examples, the target ion is magnesium, and the ionophore is 4,5-bis(benzoylthio)-1,3-dithiole-2-thione (Bz2dmit) or 1,3,5-Tris[10-(1-adamantyl)-7,9-dioxo-6,10-diazaundecyl]benzene (magnesium ionophore VI). In some examples, the target ion is calcium, and the ionophore is calcium ionophore I (ETH 1001) or calcium ionophore II (ETH129). In some examples, the target ion is chloride, and the ionophore is tridodecylmethylammonium chloride (TDMAC). In some examples, the target ion is ammonium, and the ionophore is nonactin.

In one example, the ionophore is covalently coupled to the ISM, for example, using a functionalized ISM and/or ionophore and suitable coupling chemistry such as carbodiimide or polycarbodiimide coupling/crosslinking agents. Other coupling/crosslinking agents can be used to couple the ionophore to the ISM or another membrane of the presently disclosed sensors.

In some examples, the substrate includes a material selected from the group consisting of: metal, glass, semiconductor, dielectric, transparent conductive oxide, ceramic, and polymer. In some examples, the substrate is rigid, semi-rigid, or flexible.

In some examples, the second electrode includes a metal, a metal alloy, a transition metal oxide, a transparent conductive oxide, a carbon material, a doped semiconductor, a binary semiconductor, a ternary semiconductor, or a conductive polymer. In some examples, the metal is selected from the group consisting of: gold, platinum, silver, iridium, rhodium, ruthenium, nickel, chromium, and titanium. In some examples, the metal is oxidized or in the form of a metal salt. In some examples, the carbon material is selected from the group consisting of: carbon paste, graphene oxide, reduced graphene oxide, carbon nanotubes, C60, porous carbon nanomaterial, mesoporous carbon, glassy carbon, hybrid carbon nanomaterial, graphite, and doped diamond. In some examples, the doped semiconductor is selected from the group consisting of: p- or n-doped silicon, germanium, silicon-germanium, zinc oxide, gallium arsenide, indium phosphide, gallium nitride, cadmium telluride, indium gallium arsenide, and aluminum arsenide. In some examples, the conductive polymer is selected from the group consisting of: poly(3,4-ethylenedioxythiophene) (PEDOT), poly(3,4-ethylenedioxythiophene) polystyrene sulfonate (PEDOT:PSS), polyaniline (PANI), poly(pyrrole) (PPy), or poly(3-octylthiophene) (POT).

In some examples, the first electrode is disposed directly on the substrate.

In some examples, the first and the second electrode are disposed directly on the substrate. In some examples, at least a portion of the first and the second electrodes are directly disposed on at least a portion of the substrate. In some examples, at least a portion of the first and the second electrodes are indirectly coupled to at least a portion of the substrate, for example, with an adhesive or other material that bonds a portion of the substrate with at least a portion of the electrodes.

In some examples, the device further includes a biointerface membrane disposed on the ionophore and the first electrode. In some examples, the device includes a biointerface membrane disposed on the ionophore and the first electrode as well as the second electrode, where the biointerface membrane is the same. In some examples, the biointerface membrane is configured to inhibit biofouling of the ionophore or the first electrode. In some examples, the biointerface membrane is configured to inhibit disintegration of the second electrode. In some examples, the biointerface membrane, or at least a portion of a separate drug releasing membrane, is configured to release a therapeutic compound into the biological fluid. In some examples, the biointerface membrane includes a plurality of layers. In some examples, the biointerface membrane is two or more chemically distinct or chemically identical biointerface membranes or layers of two or more chemically distinct biointerface membranes layered in an alternating or random configuration, or a combination of alternating and random configurations.

In some examples, the device includes a second biointerface membrane disposed on the second electrode. In some examples the second biointerface membrane is the same or chemically different from the biointerface membrane. In some examples, the second biointerface membrane includes a plurality of layers. In some examples, the second biointerface membrane is two or more chemically distinct biointerface membranes or layers of two or more chemically distinct or chemically identical biointerface membranes layered in an alternating or random configuration, or a combination of alternating and random configurations. In some examples, the second biointerface membrane includes a biocompatible polymer and a salt. In some examples, the second biointerface membrane consists essentially of a biocompatible polymer and a salt. In some examples, the biocompatible polymer is present in an amount of about 40 to about 70 weight percent in the second biointerface membrane. In some examples, the salt is present in an amount of about 30 to about 60 weight percent in the biointerface membrane. In some examples, the biocompatible polymer is selected from the group consisting of: polyvinyl butyral (PVB), polyurethane, and silicone. In some examples, the salt is selected from the group consisting of: potassium chloride (KCl), sodium chloride (NaCl), magnesium chloride ($MgCl_2$), calcium chloride ($CaCl_2$), and ammonium sulfate $(NH_4)_2SO_4$). In some examples, the second biointerface membrane includes a plurality of layers.

In some examples, the substrate is substantially elongated. In some examples, the substrate is an elongated shape that is planar or cylindrical.

In some examples, the substrate is planar. In some examples, the substrate is a wire.

In some examples, the device comprises sensor electronics configured to measure an electromotive force on a continuous basis.

In some examples, the sensor electronics is configured to measure the electromotive force with a dynamically configurable frequency.

In some examples, the sensor electronics includes a galvanostat.

In some examples, the sensor electronics includes a high-input impedance analog front end coupled to the first electrode and the second electrode. In some examples, the high-impedance analog front end includes at least one of an instrumentation amplifier, differential amplifier, voltage follower, unity gain amplifier, isolation amplifier, or buffer. In some examples, the high-impedance analog front end has an input impedance greater than about 100 giga-ohms.

In some examples, the sensor electronics is configured to maintain the second electrode at a substantially constant potential.

In some examples, the sensor electronics further includes an analog-to-digital converter (ADC) that digitizes the signal corresponding to the measured electromotive force.

In some examples, the sensor electronics includes a non-volatile computer-readable memory configured to store the signal.

In some examples, the sensor electronics includes a transmitter configured to wirelessly transmit the signal.

In some examples, the sensor electronics includes a non-volatile computer-readable memory configured to store correlations between control ion concentrations and control signals corresponding to electromotive forces for those control ion concentrations. The sensor electronics is configured to (a) compare the signal corresponding to the electromotive force to the control signals, (b) select the control signal which most closely matches the signal corresponding to the electromotive force, and (c) generate as the output the control ion concentration which corresponds to the selected control signal.

In some examples, the electromotive force further is at least partially based on a potential difference that is generated between the first electrode and the second electrode responsive to the biological fluid conducting an electrophysiological signal to the first electrode. In some examples, a first contribution to the electromotive force from the electrophysiological signal varies rapidly relative to a second contribution to the electromotive force from the concentration of the ion in the physiological fluid. In some examples, the sensor electronics is configured to deconvolve the first contribution from the second contribution. In some examples, the sensor electronics includes: a fast Fourier transform (FFT) circuit configured to transform the signal corresponding to the electromotive force from a time domain to the frequency domain; a spectral analysis circuit configured to separate the transformed signal into a high frequency portion corresponding to the first contribution and a low frequency portion corresponding to the second contribution; and at least one inverse FFT (iFFT) circuit configured to transform the high frequency portion into a time domain output corresponding to the electrophysiological signal and to transform the low frequency portion into a time domain output corresponding to the concentration of the ion in the physiological fluid. In some examples, the low frequency portion is approximately centered at zero frequency. In some examples, the high frequency portion includes features at the frequency of a human heartbeat or some harmonic thereof. In some examples, the high frequency portion includes features at frequencies corresponding to features of individual human heartbeats. In some examples, the high frequency portion includes features at about 100 Hz to about 1000 kHz. In some examples, the high frequency portion includes features at about 200 Hz to about 400 kHz.

In some examples, the sensor electronics includes: an analog-to-digital converter (ADC) that digitizes the signal corresponding to the electromotive force; a first filter configured to receive the digitized signal from the ADC, to remove the second contribution therefrom, and to generate an output corresponding to the first contribution with the second contribution removed; and a second filter configured to receive the digitized signal from the ADC, to remove the first contribution therefrom, and to generate an output corresponding to the second contribution with the first contribution removed.

In some examples, the sensor electronics includes: a first filter configured to remove the second contribution from the signal corresponding to the electromotive force, and to generate a first output corresponding to the first contribution with the second contribution removed; and a second filter configured to remove the first contribution from the first output or from the signal corresponding to the electromotive force, and to generate a second output corresponding to the second contribution with the first contribution removed. In some examples, the first filter includes a high-pass filter, band-block filter, or band-pass filter. In some examples, the first filter passes a frequency corresponding to a human heartbeat or heartbeat waveform. In some examples, the second filter includes a low-pass filter, band-block filter, or band-pass filter. In some examples, the second filter passes zero frequency.

In some examples, the device comprises sensor electronics configured to receive an electrophysiological signal, for example, a cardiac electrical signal.

Some examples herein provide a device for measuring an electrophysiological signal that is conducted via a biological fluid in vivo. The device may include an indwelling sensor, including: a substrate; a first electrode disposed on the substrate; and a second electrode disposed on the substrate. The device may include sensor electronics configured to generate a signal corresponding to an electromotive force, the electromotive force being at least partially based on a potential difference that is generated between the first electrode and the second electrode responsive to the biological fluid conducting the electrophysiological signal to the first electrode.

In some examples, the sensor electronics further of the device is configured to use the signal to generate an output corresponding to a measurement of the electrophysiological signal.

In some examples, the sensor electronics of the device further is configured to transmit the signal to an external device configured to use the signal to generate an output corresponding to a measurement of the concentration of the target ion in the biological fluid.

In some examples, the sensor electronics of the device includes: a fast Fourier transform (FFT) circuit configured to transform the signal corresponding to the electromotive force from a time domain to the frequency domain; a spectral analysis circuit configured to separate the transformed signal into a high frequency portion corresponding to the electrophysiological signal and a low frequency portion not corresponding to the electrophysiological signal; and at least one inverse FFT (iFFT) circuit configured to transform the high frequency portion into a time domain output corresponding to the electrophysiological signal.

In some examples, the high frequency portion includes features at the frequency of a human heartbeat or some harmonic thereof. In some examples, the high frequency portion includes features at frequencies corresponding to features of individual human heartbeats. In some examples, the high frequency portion includes features at about 100 Hz to about 1000 Hz. In some examples, the high frequency portion includes features at about 200 Hz to about 400 Hz.

In some examples, the sensor electronics of the device includes: an analog-to-digital converter (ADC) that digitizes the signal corresponding to the electromotive force; and a filter configured to receive the digitized signal from the ADC, to remove a contribution therefrom not corresponding to the electrophysiological signal, and to generate an output corresponding to the electrophysiological signal with the contribution removed.

In some examples, the sensor electronics of the device includes a filter configured to remove a contribution from the signal corresponding to the electromotive force that does not correspond to the electrophysiological signal, and to generate an output corresponding to the electrophysiological signal with the contribution removed. In some examples, the filter includes a high-pass filter, band-block filter, or band-pass filter. In some examples, the filter passes a frequency corresponding to a human heartbeat or heartbeat waveform.

In some examples, the electrophysiological signal includes a cardiac electrical signal.

In some examples, the first electrode or the second electrode of the device includes a metal, a metal alloy, a transition metal oxide, a transparent conductive oxide, a carbon material, a doped semiconductor, a binary semiconductor, a ternary semiconductor, or a conductive polymer. In some examples, the metal is selected from the group consisting of: gold, platinum, silver, iridium, rhodium, ruthenium, nickel, chromium, and titanium. In some examples, the metal is oxidized or in the form of a metal salt. In some examples, the metal displays a nanostructured surface. In some examples, the carbon material is selected from the group consisting of: carbon paste, graphene oxide, reduced graphene oxide, carbon nanotubes, C60, porous carbon nanomaterial, mesoporous carbon, glassy carbon, hybrid carbon nanomaterial, graphite, and doped diamond. In some examples, the doped semiconductor is selected from the group consisting of: p- or n-doped silicon, germanium, silicon-germanium, zinc oxide, gallium arsenide, indium phosphide, gallium nitride, cadmium telluride, indium gallium arsenide, and aluminum arsenide. In some examples, the conductive polymer is selected from the group consisting of: poly(3,4-ethylenedioxythiophene) (PEDOT), poly(3,4- ethylenedioxythiophene) polystyrene sulfonate (PEDOT:PSS), polyaniline (PANI), poly(pyrrole) (PPy), or poly(3-octylthiophene) (POT).

In some examples, the device includes a solid contact layer disposed on the first electrode. In some examples, the solid contact layer includes a metal, a carbon material, a doped semiconductor, or a conductive polymer. In some examples, the metal is selected from the group consisting of: gold, platinum, silver, iridium, rhodium, ruthenium, nickel, chromium, and titanium. In some examples, the metal is oxidized or in the form of a metal salt. In some examples, the carbon material is selected from the group consisting of: carbon paste, graphene oxide, reduced graphene oxide, carbon nanotubes, C60, porous carbon nanomaterial, mesoporous carbon, glassy carbon, hybrid carbon nanomaterial, graphite, and doped diamond. In some examples, the doped semiconductor is selected from the group consisting of: p- or n-doped silicon, germanium, silicon-germanium, zinc oxide, gallium arsenide, indium phosphide, gallium nitride, cadmium telluride, indium gallium arsenide, and aluminum arsenide. In some examples, the conductive polymer is selected from the group consisting of: poly(3,4-ethylenedioxythiophene) (PEDOT), poly(3,4-ethylenedioxythiophene) polystyrene sulfonate (PEDOT:PSS), Polyaniline (PANI), poly(pyrrole) (PPy), or poly(3-octylthiophene) (POT).

In some examples, the solid contact layer of the device includes a redox couple. In some examples, the redox couple includes metallic centers (cations) with different oxidation states. In some examples, the metallic centers are selected from the group consisting of Co(II) and Co(III); Ir(II) and Ir(III); and Os(II) and Os(III).

In some examples, the solid contact layer of the device includes a mixed conductor, or mixed ion-electron conductor. In some examples, the solid contact layer includes a compound selected from the group consisting of strontium titanate ($SrTiO_3$), titanium dioxide ($TiO_2$), (La,Ba,Sr)(Mn,Fe,Co)$O_{3-d}$,$La_2CuO_{4+d}$, cerium(IV) oxide ($CeO_2$), lithium iron phosphate ($LiFePO_4$), and $LiMnPO_4$.

In some examples, the solid contact layer of the device inhibits transport of water from the biological fluid to the first electrode.

In some examples, the solid contact layer of the device is configured to enhance electrical stability of the first electrode.

In some examples, the substrate of the device includes a material selected from the group consisting of: metal, glass, semiconductor, transparent conductive oxide, dielectric, ceramic, and polymer.

In some examples, the first electrode of the device is disposed directly on the substrate.

In some examples, the second electrode of the device is disposed directly on the substrate.

In some examples, the device further includes a biointerface membrane disposed on the first electrode. In some examples, the biointerface membrane is configured to inhibit biofouling of the first electrode. In some examples, the biointerface membrane is configured to release a therapeutic compound into the biological fluid. In some examples, the biointerface membrane includes a plurality of layers that can be arranged in a sequential or random pattern or a combination thereof.

In some examples, the device includes a second biointerface membrane disposed on the second electrode. In some examples the second biointerface membrane is the same or chemically different from the biointerface membrane. In some examples, the second biointerface membrane includes a biocompatible polymer and a salt. In some examples, the biointerface membrane consists essentially of a biocompatible polymer and a salt. In some examples, the biocompatible polymer is present in an amount of about 40 to about 70 weight percent in the second biointerface membrane. In some examples, the salt is present in an amount of about 30 to about 60 weight percent in the second biointerface membrane. In some examples, the biocompatible polymer is selected from the group consisting of: polyurethane segments or polyurea segments. In some examples, the biocompatible polymer includes: polycarbonate, polydimethylsiloxane (PDMS), methylene diphenyl diisocyanate (MDI), polysulfone (PSF), methyl methacrylate (MMA), poly(ε-caprolactone) (PCL), or 1,4-butanediol (BD). In some examples, the biocompatible polymer does not include polyvinylpyrrolidone (PVP). In some examples, the salt is selected from the group consisting of: potassium chloride (KCl), sodium chloride (NaCl), magnesium chloride ($MgCl_2$), and calcium chloride ($CaCl_2$). In some examples, the biointerface membrane includes a plurality of layers.

In some examples, the substrate of the device is elongated. In some examples, the substrate is an elongated shape that is planar or cylindrical. In some examples, the substrate of the device is elongated. In some examples, the substrate is an elongated shape that is planar or cylindrical. In some examples, the substrate of the device is planar. In some examples, the substrate is a wire.

In some examples, the sensor electronics of the device is configured to measure the electromotive force on a continuous basis.

In some examples, the sensor electronics of the device is configured to measure the electromotive force with a dynamically configurable frequency.

In some examples, the sensor electronics of the device includes a galvanostat.

In some examples, the sensor electronics of the device includes a high-impedance analog front end coupled to the first electrode and the second electrode.

In some examples, the sensor electronics of the device includes at least one of an instrumentation amplifier, differential amplifier, voltage follower, unity gain amplifier, isolation amplifier, or buffer.

In some examples, the sensor electronics of the device has an input impedance greater than about 100 giga-ohms.

In some examples, the sensor electronics of the device is configured to maintain the second electrode at a substantially constant potential.

In some examples, the sensor electronics of the device includes a non-volatile computer-readable memory configured to store the signal.

In some examples, the sensor electronics of the device includes a transmitter configured to wirelessly transmit the signal.

Some examples herein provide a method for measuring a concentration of a target ion in a biological fluid in vivo. The method may include implanting an indwelling sensor. The sensor may include a substrate; a first electrode disposed on the substrate; an ionophore disposed on the substrate and configured to selectively transport the target ion to or within the first electrode; and a second electrode disposed on the substrate. The method further may include generating a signal corresponding to an electromotive force, the electromotive force being at least partially based on a potential difference that is generated between the first electrode and the second electrode responsive to the ionophore transporting the target ion from to the first electrode. It should be apparent that any options which are described herein as pertaining to such an indwelling sensor, and operations that is performed using such a sensor, will also pertain to such a method.

Some examples herein provide a method for measuring an electrophysiological signal that is conducted via a biological fluid in vivo. The method may include implanting an indwelling sensor. The sensor may include a substrate; a first electrode disposed on the substrate; and a second electrode disposed on the substrate. The method may include generating a signal corresponding to an electromotive force, the electromotive force being at least partially based on a potential difference that is generated between the first electrode and the second electrode responsive to the biological fluid conducting the electrophysiological signal to the first electrode. It should be apparent that any options which are described herein as pertaining to such an indwelling sensor, and operations that is performed using such a sensor, will also pertain to such a method.

Some examples herein provide a device for continuously measuring a concentration of a target analyte in a biological fluid in vivo. The device may include an indwelling sensor, including: a substrate; a first electrode disposed on the substrate; an ionophore disposed on the substrate and configured to selectively transport a target ion to or within the first electrode; an enzyme configured to generate the target ion responsive to acting upon the target analyte; and a second electrode disposed on the substrate. The sensor electronics is configured to: generate a signal corresponding to an electromotive force, the electromotive force being at least partially based on a potential difference that is generated between the first electrode and the second electrode responsive to the ionophore transporting the target ion to the first electrode. It should be apparent that any options which are described herein as pertaining to other sensors and devices, and operations performed using such sensors and devices, will also pertain to such a device.

Some examples herein provide a method for continuously measuring a concentration of a target analyte in a biological fluid in vivo. The method may include implanting an indwelling sensor. The indwelling sensor may include a substrate; a first electrode disposed on the substrate; an ionophore disposed on the substrate and configured to selectively transport a target ion to or within the first electrode; an enzyme configured to generate the target ion responsive to acting upon the target analyte; and a second electrode disposed on the substrate. The method may include generating a signal corresponding to an electromotive force, the electromotive force being at least partially based on a potential difference that is generated between the first electrode and the second electrode responsive to the ionophore transporting the target ion to the first electrode. It should be apparent that any options which are described herein as pertaining to other sensors and devices, and operations performed using such sensors and devices, will also pertain to such a method.

In one example, a device for continuously measuring a concentration of at least one target analyte in a biological fluid in vivo is provided, the device comprising an indwelling analyte sensor, comprising a substrate, a first electrode disposed on the substrate, an ion-selective membrane comprising an ionophore, the ion-selective membrane disposed on the substrate and configured to selectively transport the at least one target analyte to or within the first electrode, and a second electrode disposed on the substrate. In one aspect, the device further comprises sensor electronics, the sensor electronics configured to generate a signal corresponding to an electromotive force, the electromotive force being at least partially based on a potential difference that is generated between the first electrode and the second electrode responsive to the ionophore transporting the at least one target analyte to the first electrode.

In another aspect, alone or in combination with any of the previous aspects, the ion-selective membrane is a fluorosilicone rubber, a polydimethylsiloxane polymer, a silicone rubber, a polyurethane with a polysiloxane soft segment, a polyurethane with a hard and soft segment, a water-based polyurethane, polyvinyl butyral, polymethylmethacrylate, polyvinyl acrylate, or blends or graft polymers thereof.

In another aspect, alone or in combination with any of the previous aspects, the first or second electrode, independently, is a metal, metal alloy, or conductive polymer selected from the group consisting of poly(3,4-ethylenedioxythiophene) (PEDOT), poly(3,4-ethylenedioxythiophene) polystyrene sulfonate (PEDOT:PSS), polyaniline (PANI), poly(pyrrole) (PPy), or poly(3-octylthiophene) (POT).

In another aspect, alone or in combination with any of the previous aspects, the ionophore is selected from the group consisting of: 4-tert-butylcalix[4]arene-tetraacetic acid tetraethyl ester (sodium ionophore X); calix[4]arene-25,26,27,28-tetrol (calix[4]arene); potassium ionophore I (valinomycin), potassium ionophore II: bis[(benzo-15-crown-5)-4'-ylmethyl] pimelate (BB15C5); potassium ionophore III: 2-dodecyl-2-methyl-1,3-propanediyl bis[N-[5'-nitro(benzo-15-crown-5)-4'-yl]carbamate] (BME44); 4,5-bis(benzoylthio)-1,3-dithiole-2-thione (Bz2dmit); 1,3,5-Tris[10-(1-adamantyl)-7,9-dioxo-6,10-diazaundecyl]benzene (magnesium ionophore VI); calcium ionophore I (ETH 1001); calcium ionophore II (ETH129); tridodecylmethylammonium chloride (TDMAC); and nonactin.

In another aspect, alone or in combination with any of the previous aspects, the ion-selective membrane further comprising a lipophilic salt selected from the group consisting of sodium tetrakis[3,5-bis(trifluoromethyl)phenyl]borate (NaTPFB), sodium tetraphenylborate (NaTPB), potassium tetrakis [3,5-bis(trifluoromethyl)phenyl]borate (KTFPB), and potassium tetrakis(4-chlorophenyl)borate (KTClPB).

In another aspect, alone or in combination with any of the previous aspects, the ion-selective membrane is in direct contact with the first electrode.

In another aspect, alone or in combination with any of the previous aspects, the device further comprises a solid contact layer disposed between the first electrode and the ion-selective membrane. In another aspect, alone or in combination with any of the previous aspects, the solid contact layer comprises a metal, a carbon material, a carbon ink, a carbon paste, a doped semiconductor, or a conductive polymer. In another aspect, alone or in combination with any of the previous aspects, the solid contact layer comprises a redox couple selected from the group consisting of Co(II) and Co(III); Ir(II) and Ir(III); and Os(II) and Os(III). In another aspect, alone or in combination with any of the previous aspects, the solid contact layer comprises a mixed conductor, or mixed ion-electron conductor selected from the group consisting of strontium titanate ($SrTiO_3$), titanium dioxide ($TiO_2$), $(La,Ba,Sr)(Mn,Fe,Co)O_{3-d}$,$La_2CuO_{4+d}$, cerium(IV) oxide ($CeO_2$), lithium iron phosphate ($LiFePO_4$), and $LiMnPO_4$.

In another aspect, alone or in combination with any of the previous aspects, the at least one target analyte is selected from the group consisting of sodium ion, potassium ion, hydrogen ion, lithium ion, magnesium ion, calcium ion, chloride ion, sulfite ion, sulfate ion, phosphate ion, ammonium ion, uric acid, urea, ketone, and glucose.

In another aspect, alone or in combination with any of the previous aspects, the device further comprises a biointerface membrane disposed on the ionophore and the first electrode, wherein the biocompatible polymer is selected from the group consisting of polyvinyl butyral (PVB), polyurethane, and silicone. In another aspect, alone or in combination with any of the previous aspects, the biointerface membrane is configured to release a therapeutic compound into the biological fluid.

In another aspect, alone or in combination with any of the previous aspects, the sensor electronics comprises a galvanostat. In another aspect, alone or in combination with any of the previous aspects, the sensor electronics is configured to: (a) measure the electromotive force with a dynamically configurable frequency; (b) maintain the second electrode at a substantially constant potential; or (c) combinations thereof.

In another aspect, alone or in combination with any of the previous aspects, the electromotive force is further at least partially based on a potential difference that is generated between the first electrode and the second electrode responsive to the biological fluid conducting an electrophysiological signal to the first electrode, wherein a first contribution to the electromotive force from the electrophysiological signal varies rapidly relative to a second contribution to the electromotive force from the concentration of the ion in the physiological fluid, and wherein the sensor electronics is configured to deconvolve the first contribution from the second contribution.

In another aspect, alone or in combination with any of the previous aspects, the electrophysiological signal comprises a cardiac electrical signal.

In another aspect, alone or in combination with any of the previous aspects, the device further comprises an enzyme configured to generate the at least one target analyte, wherein the enzyme is selected from an oxidase.

In one example, a method for continuously measuring a concentration of a target analyte in a biological fluid in vivo, is provided, the method comprising an indwelling sensor comprising a substrate, a first electrode disposed on the substrate, an ionophore disposed on the substrate and configured to selectively transport a target ion to or within the first electrode, a second electrode disposed on the substrate, and generating a signal corresponding to an electromotive force, the electromotive force being at least partially based on a potential difference that is generated between the first electrode and the second electrode responsive to the ionophore transporting the target ion to the first electrode.

In another aspect, the method further comprises an enzyme configured to generate the target analyte.

BRIEF DESCRIPTION OF DRAWINGS

FIGS. 1A-1I schematically illustrate example configurations and components of a device for measuring an electrophysiological signal and/or concentration of a target ion in a biological fluid in vivo.

FIGS. 2A-2G schematically illustrate additional example configurations and components of a device for measuring an electrophysiological signal and/or a concentration of a target ion in a biological fluid in vivo.

FIGS. 6A-6G schematically illustrate various additional examples of sensor configurations.

DETAILED DESCRIPTION

Figures 1A, 1B, 1C:
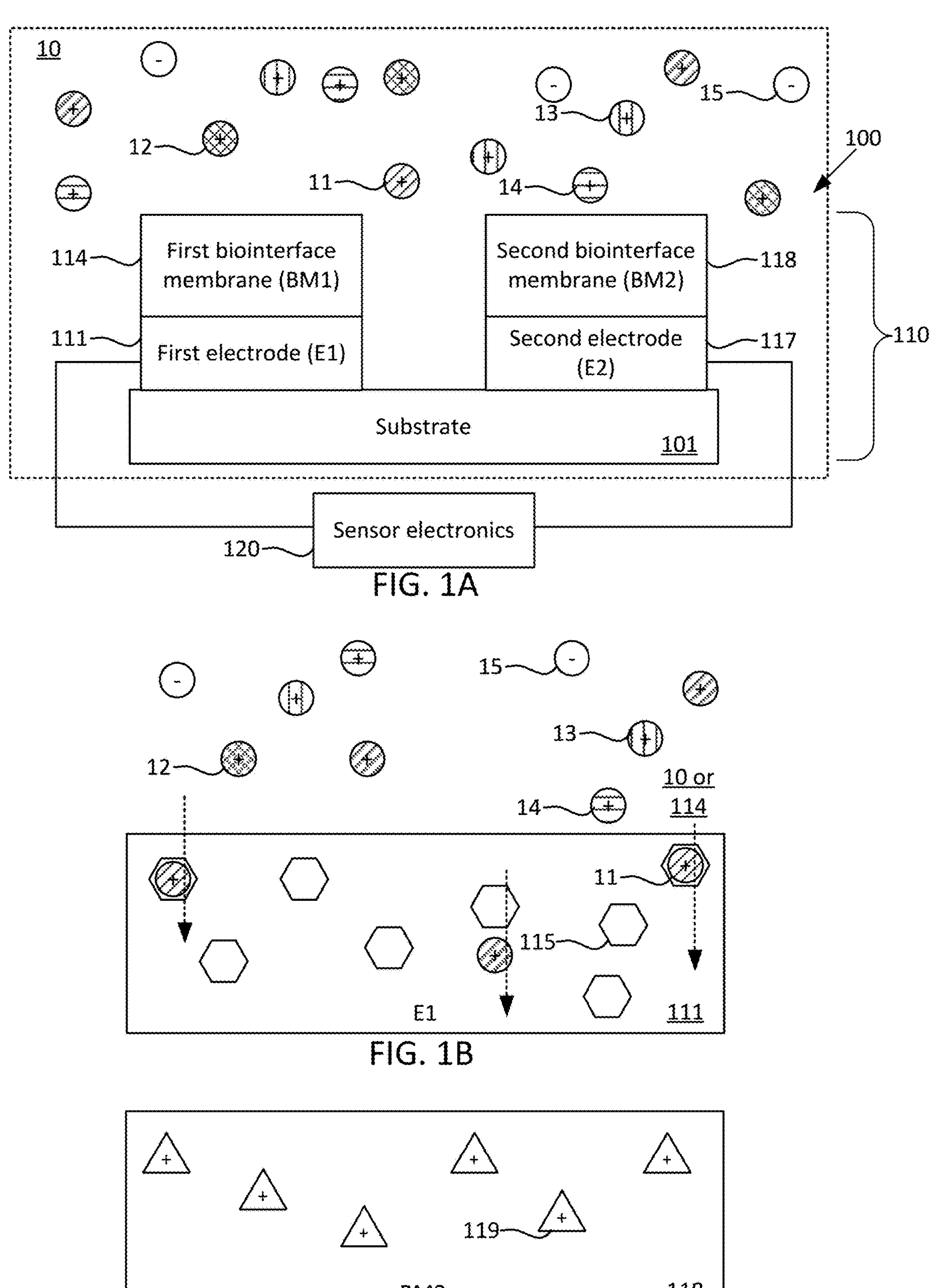
Figure 1H:
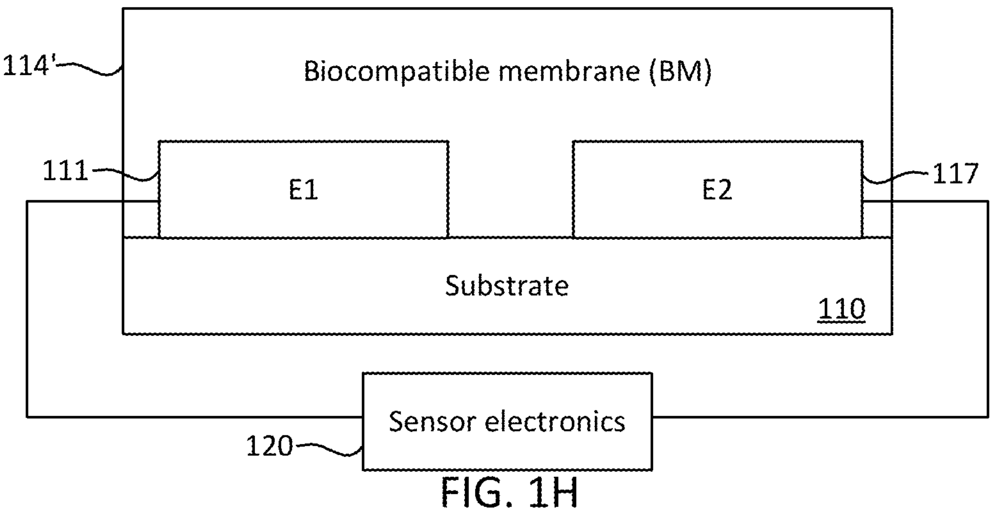

Devices and methods for measuring an electrophysiological signal and/or a concentration of a target ion in a biological fluid in vivo are provided herein.

The ability to continuously measure the concentrations of ions, in real time, may facilitate improved outcomes for those with acute and chronic disease in disparate fields such as nephrology, hepatology, and cardiology. Although bedside and point-of-care instrumentation for the assessment of electrolytes in whole blood samples have been commercially available for the past five decades, these measures provide only single snapshot in time measurement, which has limited clinical utility.

Additionally, electrophysiological recording is widely employed in the diagnosis and management of a number of diseases, such as atrial fibrillation and epilepsy. Previously known electrophysiological measurements utilize electrodes (often applied to the surface of the skin) to quantify fluctuations in electrical potential on a wide variety of scales from single ion channel proteins to whole organs like the heart. In cardiology, it enables the assessment of the heart rate and rhythm (via ECG/EKG), including variability thereof, and cardiovascular output.

A body-adorned (in vivo) platform enabling potentiometric readout of an electrophysiological signal and/or concentration of an ion in a biological fluid is provided herein. For example, the present device may include a pair of electrodes which is configured to be inserted into a host's dermis or subcutaneous tissue to potentiometrically monitor the electrophysiological signal and/or the concentration of a selected ion in the host's interstitial fluid (which concentration correlates to the concentration of that ion in the host's blood).

In another example, the present device may include a single electrode configured to be inserted into a host's dermis or subcutaneous tissue to potentiometrically monitor the electrophysiological signal and/or the concentration of a selected ion in the host's interstitial fluid (which concentration correlates to the concentration of that ion in the host's blood).

In yet another example, the present device may include two electrodes, one electrode being configured to be inserted into a host's dermis or subcutaneous tissue to potentiometrically monitor the electrophysiological signal and/or the concentration of a selected ion in the host's interstitial fluid and the other electrode being configured to be external to the host.

For example, the interstitial fluid may have an ion concentration which correlates to the ion concentration of the whole blood and can be measured on a continuous basis. The continuous basis for measurement is over a period of 3 days to 15 days or more. The measurements discussed herein is taken periodically in intervals of seconds, minutes, hours, or other time periods or combinations of time periods.

The present devices and methods may allow a host to continuously monitor the concentration of any suitable ion in the blood from anywhere (e.g., at home, work, while traveling, or other locations), which may provide the host with an improved outcome. For example, the host may have a reduced need to visit a clinic for monitoring of the concentration of the ion, is able to receive any needed treatment with reduced time lag, and ultimately may have a reduced likelihood of suffering from severe ionic imbalance, such as severe hyperkalemia (≥6.5 mM $K^+$, or any other clinically-relevant threshold, in the blood). Additionally, or alternatively, the present devices and methods may allow the host to continuously monitor his or her cardiac electrical signals, which may provide the host with an improved outcome. For example, the host may have a reduced need to visit a clinic or to use cumbersome home-based equipment for periodic monitoring of the cardiac electrical signal, is able to receive any needed treatment with reduced time lag, and ultimately may have a reduced likelihood of suffering from cardiac arrhythmia, ventricular fibrillation, or sudden cardiac death. Some examples herein provide devices and methods for the continuous and simultaneous or interleaved measurement of both ion concentration and an electrophysiological signal, using a single body-adorned sensor. However, it will be appreciated that the present devices and methods is used to continuously make just one of such measurements, e.g., to measure either an ion concentration or an electrophysiological signal, but not both.

In some examples, the presently disclosed devices are used for example in the treatment of chronic kidney disease such as in disease diagnosis, management, and treatment. Additionally, the devices is used in dialysis to provide treatment guidance, and alerts. In some examples, the presently disclosed devices are used in heart failure treatment and management, for management of medications such as RAASi medications, diuretics, insulin therapy, and other uses. In some examples, the presently disclosed devices are additionally or alternatively, used to guide other complications arising from ion imbalances for ions that can be measured using the techniques described herein. Other conditions where the presently disclosed devices are used include diabetic ketoacidosis, hyper/hypovolemia, ascities, asthma, genetic disorders and asthma. Additionally, or alternatively, the presently disclosed devices are used during hospital stay and in surgery to monitor conditions of the patient.

First, some example terms used in the present application will be explained. Then, example devices for measuring an electrophysiological signal and/or the concentration of a target ion in vivo, components thereof, and methods of making and using such devices will be provided.

Terms

In order to facilitate an understanding of the disclosed examples, a number of terms are defined below.

The phrases "analyte-measuring device," "analyte-monitoring device," "analyte-sensing device," and/or "multi-analyte sensor device" as used herein are broad phrases, and are to be given their ordinary and customary meaning to a person of ordinary skill in the art (and are not to be limited to a special or customized meaning), and refer without limitation to an apparatus and/or system responsible for the detection of, or transduction of a signal associated with, a particular analyte or combination of analytes. For example, these phrases may refer without limitation to an instrument responsible for detection of a particular analyte or combination of analytes. In one example, the instrument includes a sensor coupled to circuitry disposed within a housing, and configure to process signals associated with analyte concentrations into information. In one example, such apparatuses and/or systems are capable of providing specific quantitative, semi-quantitative, qualitative, and/or semi qualitative analytical information using a biological recognition element combined with a transducing (detecting) element.

The terms "biosensor" and/or "sensor" as used herein are broad terms and are to be given their ordinary and customary meaning to a person of ordinary skill in the art (and are not to be limited to a special or customized meaning), and refer without limitation to a part of an analyte measuring device, analyte-monitoring device, analyte sensing device, and/or multi-analyte sensor device responsible for the detection of, or transduction of a signal associated with, a particular analyte or combination of analytes. In one example, the biosensor or sensor generally comprises a body, a working electrode, a reference electrode, and/or a counter electrode coupled to body and forming surfaces configured to provide signals during electrochemical reactions. One or more membranes can be affixed to the body and cover electrochemically reactive surfaces. In one example, such biosensors and/or sensors are capable of providing specific quantitative, semi-quantitative, qualitative, semi qualitative analytical signals using a biological recognition element combined with a transducing (detecting) element.

The phrases "sensing portion," "sensing membrane," and/or "sensing mechanism" as used herein are broad phrases, and are to be given their ordinary and customary meaning to a person of ordinary skill in the art (and are not to be limited to a special or customized meaning), and refer without limitation to the part of a biosensor and/or a sensor responsible for the detection of, or transduction of a signal associated with, a particular analyte or combination of analytes. In one example, the sensing portion, sensing membrane, and/or sensing mechanism generally comprise an electrode configured to provide signals during electrochemical reactions with one or more membranes covering electrochemically reactive surface. In one example, such sensing portions, sensing membranes, and/or sensing mechanisms can provide specific quantitative, semi-quantitative, qualitative, semi qualitative analytical signals using a biological recognition element combined with a transducing (detecting) element.

The term "about" as used herein is a broad term, and is to be given its ordinary and customary meaning to a person of ordinary skill in the art (and is not to be limited to a special or customized meaning), and refers without limitation to allowing for a degree of variability in a value or range, for example, within 10%, within 5%, or within 1% of a stated value or of a stated limit of a range, and includes the exact stated value or range. The term "substantially" as used herein refers to a majority of, or mostly, as in at least about 50%, 60%, 70%, 80%, 90%, 95%, 96%, 97%, 98%, 99%, 99.5%, 99.9%, 99.99%, or at least about 99.999% or more, or 100%. The phrase "substantially free of" as used herein can mean having none or having a trivial amount of, such that the amount of material present does not affect the material properties of the composition including the material, such that about 0 wt. % to about 5 wt. % of the composition is the material, or about 0 wt. % to about 1 wt. %, or about 5 wt. % or less, or less than or equal to about 4.5 wt. %, 4, 3.5, 3, 2.5, 2, 1.5, 1, 0.9, 0.8, 0.7, 0.6, 0.5, 0.4, 0.3, 0.2, 0.1, 0.01, or about 0.001 wt. % or less, or about 0 wt. %.

The terms "adhere" and "attach" as used herein are broad terms and are to be given their ordinary and customary meaning to a person of ordinary skill in the art (and are not to be limited to a special or customized meaning), and refer without limitation to hold, bind, or stick, for example, by gluing, bonding, grasping, interpenetrating, or fusing.

The term "analyte" as used herein is a broad term and is to be given its ordinary and customary meaning to a person of ordinary skill in the art (and is not to be limited to a special or customized meaning), and refers without limitation to a substance or chemical constituent in a biological fluid (e.g., blood, interstitial fluid, cerebral spinal fluid, lymph fluid, urine, sweat, saliva, etc.) that can be analyzed. Analytes can include naturally occurring substances, artificial substances, metabolites, electrolytes, ions, gasses, hormones, proteins, enzymes, neurotransmitters, infectious agents, and/or reaction products. In some examples, the analyte measured by the sensing regions, devices, and methods is glucose. However, other analytes are contemplated as well, including but not limited to acarboxyprothrombin; acylcarnitine; adenine phosphoribosyl transferase; adenosine deaminase; albumin; alpha-fetoprotein; amino acid profiles (arginine (Krebs cycle), histidine/urocanic acid, homocysteine, phenylalanine/tyrosine, tryptophan); andrenostenedione; antipyrine; arabinitol enantiomers; arginase; benzoylecgonine (cocaine); bilirubin, biotinidase; biopterin; c-reactive protein; carnitine; carnosinase; CD4; ceruloplasmin; chenodeoxycholic acid; chloroquine; cholesterol; cholinesterase; conjugated 1-β hydroxycholic acid; cortisol; creatine; creatine kinase; creatine kinase MM isoenzyme; creatinine; cyclosporin A; d-penicillamine; de-ethylchloroquine; dehydroepiandrosterone sulfate; DNA (acetylator polymorphism, alcohol dehydrogenase, alpha 1-antitrypsin, cystic fibrosis, Duchenne/Becker muscular dystrophy, glucose-6-phosphate dehydrogenase, hemoglobin A, hemoglobin S, hemoglobin C, hemoglobin D, hemoglobin E, hemoglobin F, D-Punjab, beta-thalassemia, hepatitis B virus, HCMV, HIV-1, HTLV-1, Leber hereditary optic neuropathy, MCAD, RNA, PKU, *Plasmodium vivax,* 21-deoxycortisol); desbutylhalofantrine; dihydropteridine reductase; diptheria/tetanus antitoxin; erythrocyte arginase; erythrocyte protoporphyrin; esterase D; fatty acids/acylglycines; free β-human chorionic gonadotropin; free erythrocyte porphyrin; free thyroxine (FT4); free tri-iodothyronine (FT3); fumarylacetoacetase; galactose/gal-1-phosphate; galactose-1-phosphate uridyltransferase; gentamicin; glucose-6-phosphate dehydrogenase; glutathione; glutathione perioxidase; glycerol; glycocholic acid; glycosylated hemoglobin; halofantrine; hemoglobin variants; hexosaminidase A; human erythrocyte carbonic anhydrase I; 17-alpha-hydroxyprogesterone; hypoxanthine phosphoribosyl transferase; immunoreactive trypsin; beta-hydroxybutyrate; ketones; lactate; lead; lipoproteins ((a), B/A-1, β); lysozyme; mefloquine; netilmicin; oxygen; phenobarbitone; phenytoin; phytanic/pristanic acid; potassium, sodium, and/or other blood electrolytes; progesterone; prolactin; prolidase; purine nucleoside phosphorylase; quinine; reverse tri-iodothyronine (rT3); selenium; serum pancreatic lipase; sissomicin; somatomedin C; specific antibodies (adenovirus, anti-nuclear antibody, anti-zeta antibody, arbovirus, Aujeszky's disease virus, dengue virus, *Dracunculus medinensis, Echinococcus granulosus, Entamoeba histolytica*, enterovirus, *Giardia duodenalisa, Helicobacter pylori*, hepatitis B virus, herpes virus, HIV-1, IgE (atopic disease), influenza virus, *Leishmania donovani*, leptospira, measles/mumps/rubella, *Mycobacterium leprae, Mycoplasma pneumoniae*, Myoglobin, *Onchocerca volvulus*, parainfluenza virus, *Plasmodium falciparum*, poliovirus, *Pseudomonas aeruginosa*, respiratory syncytial virus, *rickettsia* (scrub typhus), *Schistosoma mansoni, Toxoplasma gondii, Trepenoma pallidium, Trypanosoma cruzi*/rangeli, vesicular *stomatis* virus, *Wuchereria bancrofti*, yellow fever virus); specific antigens (hepatitis B virus, HIV-1); succinylacetone; sulfadoxine; theophylline; thyrotropin (TSH); thyroxine (T4); thyroxine-binding globulin; trace elements; transferrin; UDP-galactose-4-epimerase; urea; uric acid; uroporphyrinogen I synthase; vitamin A; white blood cells; and zinc protoporphyrin. Salts, sugar, protein, fat, vitamins, and hormones naturally occurring in blood or interstitial fluids can also constitute analytes in certain examples. The analyte can be naturally present in the biological fluid, or endogenous, for example, a metabolic product, a hormone, an antigen, an antibody, and the like. Alternately, the analyte can be introduced into the body, or exogenous, for example, a contrast agent for imaging, a radioisotope, a chemical agent, a fluorocarbon-based synthetic blood, or a drug or pharmaceutical composition, including but not limited to insulin; ethanol; *cannabis* (marijuana, tetrahydrocannabinol, hashish); inhalants (nitrous oxide, amyl nitrite, butyl nitrite, chlorohydrocarbons, hydrocarbons); cocaine (crack cocaine); stimulants (amphetamines, methamphetamines, Ritalin, Cylert, Preludin, Didrex, PreState, Voranil, Sandrex, Plegine); depressants (barbiturates, methaqualone, tranquilizers such as Valium, Librium, Miltown, Serax, Equanil, Tranxene); hallucinogens (phencyclidine, lysergic acid, mescaline, peyote, psilocybin); narcotics (heroin, codeine, morphine, opium, meperidine, Percocet, Percodan, Tussionex, Fentanyl, Darvon, Talwin, Lomotil); designer drugs (analogs of fentanyl, meperidine, amphetamines, methamphetamines, and phencyclidine, for example, Ecstasy); anabolic steroids; and nicotine. The metabolic products of drugs and pharmaceutical compositions are also contemplated analytes. Analytes such as neurochemicals and other chemicals generated within the body can also be analyzed, such as, for example, ascorbic acid, uric acid, dopamine, noradrenaline, 3-methoxytyramine (3MT), 3,4-dihydroxyphenylacetic acid (DOPAC), homovanillic acid (HVA), 5-hydroxytryptamine (5HT), 5-hydroxyindoleacetic acid (FHIAA), and histamine.

The term “ion” as used herein is a broad term, and is to be given its ordinary and customary meaning to a person of ordinary skill in the art (and is not to be limited to a special or customized meaning), and refers without limitation to an atom or molecule with a net electric charge due to the loss or gain of one or more electrons. Ions in a biological fluid is referred to as “electrolytes.” Nonlimiting examples of ions in biological fluids include sodium ($Na^+$), potassium ($K^+$), magnesium ($Mg^{2+}$), calcium ($Ca^{2+}$), hydrogen (H), lithium ($Li^+$), chloride ($Cl^-$), sulfide ($S^{2-}$), sulfite ($SO_3^{2-}$), sulfate ($SO_4^{2-}$), phosphate ($PO_4^{3-}$), and ammonium ($NH_4^+$). An ion is an example of an analyte.

The phrases “biointerface membrane” and “biointerface layer” as used interchangeably herein are broad phrases, and are to be given their ordinary and customary meaning to a person of ordinary skill in the art (and are not to be limited to a special or customized meaning), and refer without limitation to a permeable membrane (which can include multiple domains) or layer that functions as a bioprotective interface between host tissue and an implantable device. The terms “biointerface” and “bioprotective” are used interchangeably herein.

The phrase “barrier cell layer” as used herein is a broad phrase, and is to be given its ordinary and customary meaning to a person of ordinary skill in the art (and is not to be limited to a special or customized meaning), and refers without limitation to a part of a foreign body response that forms a cohesive monolayer of cells (for example, macrophages and foreign body giant cells) that substantially block the transport of molecules and other substances to the implantable device.

The term “baseline” and “background” as used herein is a broad term, and is to be given its ordinary and customary meaning to a person of ordinary skill in the art (and is not to be limited to a special or customized meaning), and refers without limitation to an amount of signal (e.g., in the form of electrical current and/or voltage) produced by a sensor that is irrespective of the concentration of the measured analyte.

The term “biostable” as used herein is a broad term, and is to be given its ordinary and customary meaning to a person of ordinary skill in the art (and is not to be limited to a special or customized meaning), and refers without limitation to materials that are relatively resistant to degradation by processes that are encountered in vivo.

The term “coaxial” as used herein is to be construed broadly to include sensor architectures having elements aligned along a shared axis around a core that can be configured to have a circular, elliptical, triangular, polygonal, or other cross-sections, such elements can include electrodes, insulating layers, or other elements that can be positioned circumferentially around the core layer, such as a core electrode or core polymer wire.

The term “continuous” as used herein is a broad term, and is to be given its ordinary and customary meaning to a person of ordinary skill in the art (and is not to be limited to a special or customized meaning), and refers without limitation to an uninterrupted or unbroken portion, domain, coating, or layer of sensor systems as discussed herein.

The term “discontinuous” as used herein is a broad term, and is to be given its ordinary and customary meaning to a person of ordinary skill in the art (and is not to be limited to a special or customized meaning), and refers without limitation to disconnected, interrupted, or separated portions, layers, coatings, or domains of system systems as discussed herein.

The term “semi-continuous” as used herein is a broad term, and is to be given its ordinary and customary meaning to a person of ordinary skill in the art (and is not to be limited to a special or customized meaning), and refers without limitation to a portion, coating, domain, or layer that includes one or more continuous and noncontinuous portions, coatings, domains, or layers. For example, a coating disposed around a sensing region but not about the sensing region is “semi-continuous.”

The phrase “continuous analyte sensing” as used herein is a broad phrase, and is to be given its ordinary and customary meaning to a person of ordinary skill in the art (and is not to be limited to a special or customized meaning), and refers without limitation to the period in which monitoring of analyte concentration is continuously, continually, and/or intermittently (but regularly) performed, for example, from about every 5 seconds or less to about 10 minutes or more. In further examples, monitoring of analyte concentration is performed from about every 10, 15, 20, 25, 30, 35, 40, 45, 50, 55, or 60 seconds to about 1.25, 1.50, 1.75, 2.00, 2.25, 2.50, 2.75, 3.00, 3.25, 3.50, 3.75, 4.00, 4.25, 4.50, 4.75, 5.00, 5.25, 5.50, 5.75, 6.00, 6.25, 6.50, 6.75, 7.00, 7.25, 7.50, 7.75, 8.00, 8.25, 8.50, 8.75, 9.00, 9.25, 9.50 or 9.75 minutes. In some examples, monitoring of analyte concentration is performed about every 15 minutes, or about every 30 minutes, or about every 60 minutes; additionally, or alternatively, in some examples, monitoring of analyte concentration is performed about every 1.5 hours, about every 2 hours, about every 4 hours, about every 6 hours, or about every 8 hours.

The term “coupled” as used herein is a broad term, and is to be given its ordinary and customary meaning to a person of ordinary skill in the art (and is not to be limited to a special or customized meaning), and refers without limitation to two or more system elements or components that are configured to be at least one of electrically, mechanically, thermally, operably, chemically or otherwise attached. Similarly, the phrases “operably connected”, “operably linked”, and “operably coupled” as used herein may refer to one or more components linked to another component(s) in a manner that facilitates transmission of at least one signal between the components. In some examples, components are part of the same structure and/or integral with one another (i.e. “directly coupled”). In other examples, components are connected via remote means. For example, one or more electrodes can be used to detect an analyte in a sample and convert that information into a signal; the signal can then be transmitted to an electronic circuit. In this example, the electrode is "operably linked" to the electronic circuit. The phrase "removably coupled" as used herein may refer to two or more system elements or components that are configured to be or have been electrically, mechanically, thermally, operably, chemically, or otherwise attached and detached without damaging any of the coupled elements or components. The phrase "permanently coupled" as used herein may refer to two or more system elements or components that are configured to be or have been electrically, mechanically, thermally, operably, chemically, or otherwise attached but cannot be uncoupled without damaging at least one of the coupled elements or components.

The term "distal" as used herein is a broad term, and is to be given its ordinary and customary meaning to a person of ordinary skill in the art (and is not to be limited to a special or customized meaning), and refers without limitation to a region spaced relatively far from a point of reference, such as an origin or a point of attachment.

The term "domain" as used herein is a broad term, and is to be given its ordinary and customary meaning to a person of ordinary skill in the art (and is not to be limited to a special or customized meaning), and refers without limitation to a region of the membrane system that can be a layer, a uniform or non-uniform gradient (for example, an anisotropic region of a membrane), or a portion of a membrane that is capable of sensing one, two, or more analytes. The domains discussed herein can be formed as a single layer, as two or more layers, as pairs of bi-layers, or as combinations thereof.

The term "drift" as used herein is a broad term, and is to be given its ordinary and customary meaning to a person of ordinary skill in the art (and is not to be limited to a special or customized meaning), and refers without limitation to a progressive increase or decrease in signal over time that is unrelated to changes in host systemic analyte concentrations, for example, such as a host postprandial glucose concentrations. While not wishing to be bound by any particular theory or any particular analyte, it is believed that drift in association with glucose measurement is the result of a local decrease in glucose transport to the sensor, for example, due to a formation of a foreign body capsule (FBC). It may also be a consequence of a gradual decay in the activity or quantity of an enzyme, such as glucose oxidase, within a sensor. It is also believed that an insufficient amount of interstitial fluid surrounding the sensor may result in reduced oxygen and/or glucose transport to the sensor. In one example, an increase in local interstitial fluid may slow or reduce drift and thus improve sensor performance. Drift in signal may arise due to a changing baseline/background signal measured by the sensor and/or a change in sensitivity exhibited by the sensor. Drift may also be the result of sensor electronics, or algorithmic models used to compensate for noise or other anomalies that can occur with electrical signals in the picoamp range and nanoamp range in ranges including the microampere range, picoampere range, nanoampere range, and femtoampere range. As discussed herein, "sensor electronics" may include various combinations of hardware and/or software that is employed to detect, receive, process, store, and/or analyze the signal(s) generated by the devices and systems discussed herein, including circuitry.

The phrases "drug releasing membrane" and "drug releasing layer" as used interchangeably herein are each a broad phrase, and each are to be given its ordinary and customary meaning to a person of ordinary skill in the art (and is not to be limited to a special or customized meaning), and refers without limitation to a permeable or semi-permeable membrane which is permeable to one or more bioactive agents. In one example, the "drug releasing membrane" and "drug releasing layer" can include two or more domains and may be, in some examples, a few microns thickness or more. In one example, the drug releasing layer and/or drug releasing membrane are substantially the same as the biointerface layer and/or biointerface membrane. In another example, the drug releasing layer and/or drug releasing membrane are distinct from the biointerface layer and/or biointerface membrane. Further examples of drug releasing layers and membranes is found in pending U.S. patent application Ser. No. 17/697,701, titled, "DRUG RELEASING MEMBRANE FOR ANALYTE SENSOR," filed Mar. 17, 2022, incorporated by reference in its entirety herein, and U.S. Provisional Application No. 63/318,901, titled "DRUG RELEASING MEMBRANE FOR ANALYTE SENSOR," filed Mar. 11, 2022, incorporated by reference in its entirety herein, and U.S. Provisional Patent Application No. 63/244,644. titled, "DRUG RELEASING MEMBRANE FOR ANALYTE SENSOR," filed Sep. 16, 2021, incorporated by reference in its entirety herein.

The term "electrochemically reactive surface" as used herein is a broad term, and is to be given its ordinary and customary meaning to a person of ordinary skill in the art (and is not to be limited to a special or customized meaning), and refers without limitation to the surface of an electrode where an electrochemical reaction takes place. In various examples, a byproduct of a reaction of an analyte being detected includes at least one measurable species. The at least one measurable species can react with an electrochemically active surface, such as a working electrode.

The phrase "hard segment" as used herein is a broad phrase, and is to be given its ordinary and customary meaning to a person of ordinary skill in the art (and is not to be limited to a special or customized meaning), and refers without limitation to an element of a copolymer, for example, a polyurethane, a polycarbonate polyurethane, or a polyurethane urea copolymer, which imparts resistance properties, e.g., resistance to bending or twisting. The phrase "hard segment" can be further characterized as a crystalline, semi-crystalline, or glassy material with a glass transition temperature determined by dynamic scanning calorimetry ("Tg") typically above ambient temperature. Exemplary hard segment elements used to prepare a polycarbonate polyurethane, or a polyurethane urea hard segment include norbornane diisocyanate (NBDI), isophorone diisocynate (IPDI), tolylene diisocyanate (TDI), 1,3-phenylene diisocyanate (MPDI), trans-1,3-bis(isocynatomethyl) cyclohexane (1,3-H6XDI), bicyclohexylmethane-4,4'-diisocynate (HMDI), 4,4'-Diphenylmethane diisocyanate (MDI), trans-1, 4-bis(isocynatomethyl) cyclohexane (1,4-H6XDI), 1,4-cyclohexyl diisocyanate (CHDI), 1,4-phenylene diisocynate (PPDI), 3,3'-Dimethyl-4,4'-biphenyldiisocyanate (TODI), 1,6-hexamethylene diisocyanate (HDI), or combinations thereof.

The term "host" as used herein is a broad term, and is to be given its ordinary and customary meaning to a person of ordinary skill in the art (and is not to be limited to a special or customized meaning), and refers without limitation to mammals, for example humans.

The terms "indwelling," "in dwelling," "implanted," or "implantable" as used herein are broad terms, and are to be given their ordinary and customary meaning to a person of ordinary skill in the art (and are not to be limited to a special or customized meaning), and refer without limitation to objects including sensors that are inserted, or configured to be inserted, subcutaneously (i.e. in the layer of fat between the skin and the muscle), intracutaneously (i.e. penetrating the stratum corneum and positioning within the epidermal or dermal strata of the skin), or transcutaneously (i.e. penetrating, entering, or passing through intact skin), which may result in a sensor that has an in vivo portion and an ex vivo portion. The term "indwelling" also encompasses an object which is configured to be inserted subcutaneously, intracutaneously, or transcutaneously, whether or not it has been inserted as such.

The phrase "insertable volume" as used herein is a broad phrase, and is to be given its ordinary and customary meaning to a person of ordinary skill in the art (and is not to be limited to a special or customized meaning), and refers without limitation to a volume ahead of and alongside a path of insertion of an insertable portion of an analyte sensor, as described herein, as well as an incision made in the skin to insert the insertable portion of the analyte sensor. The insertable volume also includes up to 5 mm radially or perpendicular to the volume ahead of and alongside the path of insertion.

The terms "interferants," and "interfering species" as used herein are broad terms, and are to be given their ordinary and customary meaning to a person of ordinary skill in the art (and are not to be limited to a special or customized meaning), and refer without limitation to effects and/or species, including ions, electroactive substances, endogenous circulating species, exogenous circulating species, pharmacologic agents, and/or electromagnetic waves (such as from a magnetic resonance imaging (MRI) system or medical device) that interfere with the measurement of an analyte of interest in a sensor to produce a signal that does not accurately represent the analyte measurement.

The term "in vivo" as used herein is a broad term, and is to be given its ordinary and customary meaning to a person of ordinary skill in the art (and is not to be limited to a special or customized meaning), and without limitation is inclusive of the portion of a device (for example, a sensor) adapted for insertion into and/or existence within a living body of a host.

The term "ex vivo" as used herein is a broad term, and is to be given its ordinary and customary meaning to a person of ordinary skill in the art (and is not to be limited to a special or customized meaning), and without limitation is inclusive of a portion of a device (for example, a sensor) adapted to remain and/or exist outside of a living body of a host.

The term "membrane" as used herein is a broad term, and is to be given its ordinary and customary meaning to a person of ordinary skill in the art (and is not to be limited to a special or customized meaning), and refers without limitation to a structure configured to perform functions including, but not limited to, protection of the exposed electrode surface from the biological environment, diffusion resistance (limitation) of the analyte, service as a matrix for a catalyst for enabling an enzymatic reaction, limitation or blocking of interfering species, provision of hydrophilicity at the electrochemically reactive surfaces of the sensor interface, service as an interface between host tissue and the implantable device, modulation of host tissue response via drug (or other substance) release, and combinations thereof. When used herein, the terms "membrane" and "matrix" are meant to be interchangeable.

The phrase "membrane system" as used herein is a broad phrase, and is to be given its ordinary and customary meaning to a person of ordinary skill in the art (and is not to be limited to a special or customized meaning), and refers without limitation to a permeable or semi-permeable membrane that can be comprised of two or more domains, layers, or layers within a domain, and is constructed of materials of a few microns thickness or more, which is permeable to at least the ion the concentration of which is to be measured.

The term "micro," as used herein is a broad term, and is to be given its ordinary and customary meaning to a person of ordinary skill in the art (and is not to be limited to a special or customized meaning), and refers without limitation to a small object or scale of approximately 10-6 m that is not visible without magnification. The term "micro" is in contrast to the term "macro," which refers to a large object that is visible without magnification. Similarly, the term "nano" refers to a small object or scale of approximately 10-9 m.

The term "molecular physiological measures" (MPM) as used herein is a broad term used in its ordinary sense including, without limitation, a signal that can be monitored in vivo or ex vivo, or via a combination of both, using the systems and methods discussed herein, and may include heart rate, waveform(s) of heart rate, tissue oxygenation, bioelectrical impedance, galvanic response, respiration, core body temperature, and blood pressure which can be measured and analyzed as discussed herein.

The term "noise," as used herein, is a broad term and is used in its ordinary sense, including, without limitation, a signal detected by the sensor or sensor electronics that is unrelated to analyte concentration and can result in reduced sensor performance. Noise may originate, for example, from physiologic sources (such as the protein adsorption, the foreign body response), pharmacologic sources (such as a medication), external perturbations (e.g., pressure-induced sensor attenuations, triboelectric effects, motion artifacts, electromagnetic waves (e.g., MRI system or medical device)), and/or from the sensor electronics (e.g., Johnson-Nyquist noise, shot noise). One type of noise has been observed during the few hours (e.g., about 2 to about 24 hours) after sensor insertion. After the first 24 hours, the noise may disappear or diminish, but in some hosts, the noise may last for about three to four days. In some cases, noise can be reduced using predictive modeling, artificial intelligence, and/or algorithmic means. In other cases, noise can be reduced by addressing immune response factors associated with the presence of the implanted sensor, such as using a drug releasing layer with at least one bioactive agent. For example, noise of one or more exemplary biosensors as presently disclosed can be determined and then compared qualitatively or quantitatively. By way of example, by obtaining a raw signal timeseries with a fixed sampling interval (in units of microvolts (μV)), a smoothed version of the raw signal timeseries can be obtained, e.g., by applying a 3rd order lowpass digital Chebyshev Type II filter. Others smoothing algorithms can be used. At each sampling interval, an absolute difference, in units of μV, can be calculated to provide a smoothed timeseries. This smoothed timeseries can be converted into units of mM, (the unit of "noise"), using a glucose sensitivity timeseries, in units of μV/mM, where the ion sensitivity timeseries is derived by using a mathematical model between the raw signal and reference blood ion measurements (e.g., obtained from Blood Electrolyte Analyzer). Optionally, the timeseries can be aggregated as desired, e.g., by hour or day. Comparison of corresponding timeseries between different exemplary biosensors with the presently disclosed drug releasing layer and one or more bioactive agents provides for qualitative or quantitative determination of improvement of noise.

The term "optional" or "optionally" as used herein is a broad term, and is to be given its ordinary and customary meaning to a person of ordinary skill in the art (and is not to be limited to a special or customized meaning), and, without limitation, means that the subsequently described event or circumstance can or cannot occur, and that the description includes instances where the event or circumstance occurs and instances where it does not.

The term "planar" as used herein is to be interpreted broadly to describe sensor architecture having a substrate including a first side and a second side, and a plurality of elements arranged on one or more sides of the substrate, the elements may or may not be electrically or otherwise coupled, where the elements can include conductive or insulating layers or elements configured to operate as a circuit.

The term "proximal" as used herein is a broad term, and is to be given its ordinary and customary meaning to a person of ordinary skill in the art (and is not to be limited to a special or customized meaning), and refers without limitation to the spatial relationship between various elements in comparison to a particular point of reference. For example, some examples of a device include a membrane system having a biointerface membrane and a layer including an ionophore. If an electrode is deemed to be the point of reference and the ionophore-containing layer is positioned nearer to the electrode than the biointerface membrane, then the ionophore-containing layer is more proximal to the sensor than the biointerface membrane.

The phrase and term "processor module" and "microprocessor" as used herein are each a broad phrase and term, and are to be given their ordinary and customary meaning to a person of ordinary skill in the art (and are not to be limited to a special or customized meaning), and refer without limitation to a computer system, state machine, processor, or the like designed to perform arithmetic or logic operations using logic circuitry that responds to and processes the basic instructions that drive a computer.

The phrase "sensing membrane" as used herein is a broad phrase, and is to be given its ordinary and customary meaning to a person of ordinary skill in the art (and is not to be limited to a special or customized meaning), and refers without limitation to a permeable or semi-permeable membrane that can comprise one or more domains, layers, or layers within domains and that is constructed of materials having a thickness of a few microns or more, and that are permeable to reactants and/or co-reactants employed in determining the analyte of interest. As an example, a sensing membrane can comprise an immobilized ionophore, which selectively binds an ion to permit measurement of a concentration of that ion.

During general operation of the analyte measuring device, biosensor, sensor, sensing region, sensing portion, or sensing mechanism, a biological sample, for example, blood or interstitial fluid, or a component thereof contacts, either directly, or after passage through one or more membranes, an ionophore capable of specifically and reversibly binding to at least one ion. The interaction of the biological sample or component thereof with the analyte measuring device, biosensor, sensor, sensing region, sensing portion, or sensing mechanism results in transduction of a signal that permits a qualitative, semi-qualitative, quantitative, or semi-qualitative determination of the ion in the biological sample.

Various examples of sensor architectures is found in pending U.S. Application No. 63/321,538, titled, "CONTINUOUS ANALYTE SENSOR SYSTEMS," filed Mar. 17, 2022, incorporated by reference in its entirety herein, as well as U.S. Pat. No. 8,133,178 to Brauker et al., which is incorporated herein by reference in its entirety, as well as U.S. Pat. No. 8,828,201, Simpson, et al.; U.S. Pat. No. 9,131,885 Simpson, et al.; U.S. Pat. No. 9,237,864, Simpson, et al.; and 9,763,608, Simpson, et al., each of which is incorporated by reference in its entirety herein. Examples of methods of forming the sensors (sensor electrode layouts and membrane) and sensor systems discussed herein is found in currently pending U.S. Patent Pub. 2019/0307371 to Boock et al., incorporated by reference in its entirety herein.

In one example, the sensing region determines the selectivity among one or more analytes, so that only the analyte which has to be measured leads to (transduces) a detectable signal. The selection is based on any chemical or physical recognition of the analyte by the sensing region, where the chemical composition of the analyte is unchanged, or in which the sensing region causes or catalyzes a reaction of the analyte that changes the chemical composition of the analyte.

The sensing region transduces the recognition of analytes into a semi-quantitative or quantitative signal. Thus, "transducing" or "transduction" and their grammatical equivalents as are used herein encompasses electrochemical technologies and methods. Electrochemical properties include current and/or voltage, capacitance, and potential.

The phrases and terms "small diameter sensor," "small structured sensor," and "micro-sensor" as used herein are broad phrases and terms, and are to be given their ordinary and customary meaning to a person of ordinary skill in the art (and are not to be limited to a special or customized meaning), and refer without limitation to sensing mechanisms that are less than about 2 mm in at least one dimension. In further examples, the sensing mechanisms are less than about 1 mm in at least one dimension. In some examples, the sensing mechanism (sensor) is less than about 0.95, 0.9, 0.85, 0.8, 0.75, 0.7, 0.65, 0.6, 0.5, 0.4, 0.3, 0.2, or 0.1 mm. In some examples, the maximum dimension of an independently measured length, width, diameter, thickness, or circumference of the sensing mechanism does not exceed about 2 mm. In some examples, the sensing mechanism is a coaxial or wire-type sensor, wherein the diameter is less than about 1 mm, see, for example, U.S. Pat. No. 6,613,379 to Ward et al. and U.S. Pat. No. 7,497,827 to Brister et al., both of which are incorporated herein by reference in their entirety. In some alternate examples, the sensing mechanism includes electrodes deposited on a planar or substantially planar substrate, wherein the thickness of the implantable portion is less than about 1 mm, see, for example, U.S. Pat. No. 6,175,752 to Say et al. and U.S. Pat. No. 5,779,665 to Mastrototaro et. al., both of which are incorporated herein by reference in their entirety. Examples of methods of forming sensors (sensor electrode layouts and membrane) and sensor systems which is used to prepare the present sensors is found in US Patent Pub 2019/0307371 to Boock et al., incorporated by reference in its entirety herein.

The term "sensitivity" as used herein is a broad term, and is to be given its ordinary and customary meaning to a person of ordinary skill in the art (and is not to be limited to a special or customized meaning), and refers without limitation to an amount of signal (e.g., in the form of electrical current and/or voltage) produced by a predetermined amount (unit) of the measured analyte. For example, in one example, a sensor has a sensitivity (or slope) of from about 1 to about 100 picoamps of current for every 1 mg/dL of glucose analyte. In another example, a sensor has a sensitivity (or slope) of from about 10 to 100 millivolts of potential for every order of magnitude (in base 10 order of magnitude) change of potassium ion, and in some examples around 59 millivolts of potential for every order of magnitude (in base 10 order of magnitude) change of potassium ion with essentially zero current (less than 0.1 picoamps).

The phrase "soft segment" as used herein is a broad phrase, and is to be given its ordinary and customary meaning to a person of ordinary skill in the art (and is not to be limited to a special or customized meaning), and refers without limitation to an element of a copolymer, for example, a polyurethane, a polycarbonate-polyurethane, or a polyurethane urea copolymer, which imparts flexibility to the chain. The phrase "soft segment" can be further characterized as an amorphous material with a low Tg, e.g., a Tg not typically higher than ambient temperature or normal mammalian body temperature.

The term and phrase "zwitterion" and "zwitterionic compound" as used herein are each a broad term and phrase, and are to be given their ordinary and customary meaning to a person of ordinary skill in the art (and is not to be limited to a special or customized meaning), and refer without limitation to compounds in which a neutral molecule of the compound has a unit positive and unit negative electrical charge at different locations within the molecule. Such compounds are a type of dipolar compound, and are also sometimes referred to as "inner salts."

Devices and methods for measuring an electrophysiological signal and/or concentration of a target analyte in vivo are provided.

Nonlimiting examples of devices and methods for measuring a physiological signal and/or concentration of a target analyte in vivo now will be described with reference to FIGS. 1A-1I, 2A-2G, 3, 4A-4B, 5A-5B, 6A-6G, 7A-7C, and 8.

FIGS. 1A-1I schematically illustrate example configurations and components of a device 100 for measuring an electrophysiological signal and/or concentration of a target analyte such as a target ion 11 in a biological fluid 10 in vivo. Turning first to FIG. 1A, device 100 includes indwelling sensor 110 and sensor electronics 120. Sensor 110 includes substrate 101, first electrode (E1) 111 disposed on the substrate, and a second electrode (E2) 117 disposed on the substrate. First electrode 111 is referred to as a working electrode (WE), while second electrode 117 is referred to as a reference electrode (RE). In one example, the sensor electronics 120 is configured to generate a signal corresponding to an electromotive force (EMF). In some examples, the EMF is at least partially based on a potential difference that is generated between the first electrode 111 and the second electrode 117 responsive to biological fluid 10 conducting the electrophysiological signal to first electrode 111. In some examples, the EMF is at least partially based on a potential difference that is generated between the first electrode 111 and the second electrode 117, that being the electrical potential of the first electrode 111 responsive to the concentration of the target analyte present in the biological fluid 10. In one example, sensor electronics 120 is configured to use the signal to generate an output corresponding to a measurement of the signal. In various examples, the EMF is at least partially based on a potential difference between (i) either the first electrode 111 or the second electrode 117 and (ii) another electrode which is spaced apart from the first electrode or second electrode.

Additionally, or alternatively, in some examples, device 100 may include an ionophore 115 disposed on the substrate 101 and configured to selectively transport the target ion 11 to or within the first electrode 111. In one example, the EMF is at least partially based on a potential difference is generated between the first electrode 111 and the second electrode 117 responsive to the ionophore 115 transporting the target ion to or through the first electrode 111. In one example, the sensor electronics 120 (and/or an external device that receives the signal via a suitable wired or wireless connection) is configured to use the signal to generate an output corresponding to a measurement of the concentration of the target ion in the biological fluid. Further details regarding the configuration and use of sensor electronics 120 are provided further below.

Optionally, the first electrode 111 is used to measure an electrophysiological signal in addition to ion concentration. In other examples, such as when device 100 is configured to detect an electrophysiological signal but not an ion concentration, first electrode 111 need not include an ionophore such as the ionophore 115. In other examples, the first electrode 111 may include an ionophore that is inactive such that it does not interfere with the measurement of the electrophysiological signal.

In a manner such as illustrated in FIG. 1A, biological fluid 10 may include a plurality of ions 11, 12, 13, 14, and 15. In one example, device 100 is configured to measure the concentration of ion 11, and accordingly such ion is referred to as a "target" ion. In one example, target ion 11 is any suitable ion, and in nonlimiting examples is selected from the group consisting of sodium ($Na^+$), potassium ($K^+$), magnesium ($Mg^{2+}$), calcium ($Ca^{2+}$), hydrogen ($H^+$), lithium ($Li^+$), chloride ($Cl^-$), sulfite ($SO_3^{2-}$), sulfate ($SO_4^{2-}$), phosphate ($PO_4^{3-}$), and ammonium ($NH_4^+$). In one example, ions 12, 13, 14, and 15 is of the group consisting of sodium ($Na^+$), potassium ($K^+$), magnesium ($Mg^{2+}$), calcium ($Ca^{2+}$), hydrogen (H), lithium ($Li^+$), chloride ($Cl^-$), sulfide ($S^{2-}$), sulfite ($SO_3^{2-}$), sulfate ($SO_4^{2-}$), phosphate ($PO_4^{3-}$), and ammonium ($NH_4^+$). In one example, ions 12, 13, 14, and 15 is considered interferants to the measurement of target ion 11 because they have the potential interfere with the measurement of target ion 11 by sensor to produce a signal that does not accurately represent the concentration of target ion 11. In one example, ionophore 115 is selected so as to selectively transport target ion 11 to or within first electrode 111 and to inhibit, fully, partially and/or substantially, the transport of one or more of ions 12, 13, 14, or 15 to or within first electrode 111. For example, as illustrated in FIG. 1B, ionophore 115 may selectively transport, or selectively bind, target ions 11 from biological fluid 10 or from biointerface membrane 114 (if provided, e.g., as described below) to and within first electrode 111, while ions 12, 13, 14, and 15 may substantially remain within biological fluid 10 or biointerface membrane 114. Accordingly, contributions to the potential difference between first electrode 111 and second electrode 117 responsive to the transport of ions to or within first electrode 111 substantially are primarily caused by target ion 11 instead of by one or more of ions 12, 13, 14, or 15.

A wide variety of ionophores 115 can be used to selectively transport corresponding ions in a manner such as described with reference to FIGS. 1A-1B. In one example, where the target ion 11 is hydrogen (via peroxide), the ionophore 115 is tridodecylamine, 4-nonadecylpyridine, N,N-dioctadecylmethylamine, octadecyl isonicotinate, calix [4]-aza-crown. In another example, where the target ion 11 is lithium, the ionophore 115 is ETH 149, N,N,N',N',N",N"-hexacyclohexyl-4,4',4"-propylidynetris(3-oxabutyramide), or 6,6-Dibenzyl-1,4,8-11-tetraoxacyclotetradecane. In another example, where the target ion 11 is sulfite, the ionophore 115 is octadecyl 4-formylbenzoate. In another example, where the target ion 11 is sulfate, the ionophore 115 is 1,3-[bis(3-phenylthioureidomethyl)]benzene or zinc phthalocyanine. In another example, where the target ion 11 is phosphate, the ionophore 115 is 9-decyl-1,4,7-triazacyclodecane-8,10-dione. In another example, where the target ion 11 is sodium, the ionophore 115 is 4-tert-butylcalix[4]arene-tetraacetic acid tetraethyl ester (sodium ionophore X) or calix[4]arene-25,26,27,28-tetrol (calix[4]arene). In another example, where the target ion 11 is potassium, the ionophore 115 is potassium ionophore I (valinomycin), potassium ionophore II (BB15C5) or potassium ionophore III (BME44). In another example, where the target ion is magnesium, the ionophore 115 is 4,5-bis(benzoylthio)-1,3-dithiole-2-thione (Bz2dmit) or 1,3,5-Tris[10-(1-adamantyl)-7,9-dioxo-6,10-diazaundecyl]benzene (magnesium ionophore VI). In another example, where the target ion is calcium, the ionophore 115 is calcium ionophore I (ETH 1001) or calcium ionophore II (ETH129). In another example, where the target ion is chloride, the ionophore 115 is tridodecylmethylammonium chloride (TDMAC). In yet another example, where the target ion is ammonium, the ionophore 115 is nonactin.

In the nonlimiting example illustrated in FIG. 1A, ionophore 115 is provided within first electrode 111, and in such example the first electrode is referred to as an ion-selective electrode (ISE), since the ionophore 115 selectively transports the target ion 11. In some examples, first electrode 111 includes a conductive polymer optionally having ionophore 115 therein. Illustratively, the conductive polymer is present in an amount of about 90 to about 99.5 weight percent in the first electrode 111. In one example, the ionophore 115 is present in an amount of about 0.5 to about 10 weight percent in the first electrode. In some examples, the conductive polymer is selected from the group consisting of: poly(3,4-ethylenedioxythiophene) (PEDOT), poly(3,4-ethylenedioxythiophene) polystyrene sulfonate (PEDOT:PSS), polyaniline (PANI), poly(pyrrole) (PPy), or poly(3-octylthiophene) (POT).

While conductive polymers (such as listed above) suitably can be used in a first electrode 111 that excludes ionophore 115, other materials alternatively can be used, some nonlimiting examples of which are described below with reference to FIGS. 2A-2G. Optionally, ionophore 115 is provided in a membrane which is disposed on a first electrode 111 (which electrode may exclude ionophore 115), e.g., such as will be described below with reference to FIGS. 2A-2G.

In one example, first electrode 111 is configured in such a manner as to enhance its biocompatibility. For example, first electrode 111 may substantially exclude any plasticizer, which otherwise may leach into the biological fluid 10, potentially causing toxicity and/or a degradation in device performance. As used herein, the "substantial" exclusion of materials such as plasticizers (e.g., phthalate, sebacate, nitrophenyl ether and fluorophenyl nitrophenyl ether plasticizers) is intended to mean that the first electrode 111 or other aspects discussed herein do not contain detectable quantities of the "substantially" excluded material. In some examples, the first electrode 111 may consist essentially of the conductive polymer, optionally in addition to the ionophore 115. In some examples, the first electrode 111 may consist essentially of the conductive polymer, the ionophore 115, and an additive with ion exchanger capability, e.g., an additive that forms a complex with the ionophore and results in improved selectivity towards the target ion. In one example, the additive contributes to the ion selectivity. In another example, the additive may not provide ion selectivity. For example, the additive may help to provide a substantially even (modulate and/or attenuate) concentration of the ion in the membrane. Additionally, or alternatively, the additive may help any change in ion concentration in the biofluid to cause an ion exchange within the membrane that may induce a non-selective potential difference. Additionally, or alternatively, the ionophore and the ion exchanger may form a complex which improves the ionophore's selectivity towards the target ion as compared to the selectivity of the ionophore alone.

Optionally, the additive may include a lipophilic salt. In nonlimiting examples, the lipophilic salt is selected from the group consisting of sodium tetrakis[3,5-bis(trifluoromethyl)phenyl]borate (NaTPFB), sodium tetraphenylborate (NaTPB), potassium tetrakis [3,5-bis(trifluoromethyl)phenyl]borate (KTFPB), and potassium tetrakis(4-chlorophenyl)borate (KTClPB). In one example, the additive is present in an amount of about 0.01 to about 1 weight percent in the first electrode, or other suitable amount.

Other materials within sensor 110 is selected. In one example, substrate 101 includes a material selected from the group consisting of: metal, glass, transparent conductive oxide, semiconductor, dielectric, ceramic, and polymer (such as biopolymer or synthetic polymer). In some examples, second electrode 117 includes a metal, a metal alloy, a transition metal oxide, a transparent conductive oxide, a carbon material, a doped semiconductor, a binary semiconductor, a ternary semiconductor, or a conductive polymer. In one example, the binary semiconductor includes any two elements suitable for use in a semiconductor. In one example, the ternary semiconductor includes two or more binary semiconductors. In one example, where a metal or a metal alloy is used, the metal or metals used can be selected from the group consisting of: gold, platinum, silver, iridium, rhodium, ruthenium, nickel, chromium, and titanium. In one example, the metal optionally is oxidized or optionally is in the form of a metal salt. A nonlimiting example of an oxidized metal used in second electrode 117 is iridium oxide. In one example, the metal optionally is disposed in the form of a nanostructured surface. In one example, the carbon material is selected from the group consisting of: carbon paste, graphene oxide, carbon nanotubes, C60, porous carbon nanomaterial, mesoporous carbon, glassy carbon, hybrid carbon nanomaterial, graphite, and doped diamond. In one example, the doped semiconductor is selected from the group consisting of: silicon, germanium, silicon-germanium, zinc oxide, gallium arsenide, indium phosphide, gallium nitride, cadmium telluride, indium gallium arsenide, and aluminum arsenide. In one example, the transition metal oxide is selected from the group of: titanium dioxide ($TiO_2$), iridium dioxide ($IrO_2$), platinum dioxide ($PtO_2$), zinc oxide (ZnO), copper oxide (CuO), cerium dioxide ($CeO_2$), ruthenium(IV) oxide ($RuO_2$), tantalum pentoxide ($Ta_2O_5$), titanium dioxide ($TiO_2$), molybdenum dioxide ($MoO_2$), and manganese dioxide ($MnO_2$). In one example, the metal alloy is selected from the group consisting of: platinum-iridium (Pt—Ir), platinum-silver (Pt—Ag), platinum-gold (Pt—Au), gold-iridium (Au—Ir), gold-copper (Au—Cu), gold-silver (Au—Ag), and cobalt-iron (Co—Fe).

In one example, the conductive polymer that is used for the sensor 110 is selected from the group consisting of: poly(3,4-ethylenedioxythiophene) (PEDOT), poly(3,4-ethylenedioxythiophene) polystyrene sulfonate (PEDOT:PSS), polyaniline (PANI), poly(pyrrole) (PPy), or poly(3-octylthiophene) (POT). That is, first electrode 111 and second electrode 117 optionally is formed of the same material as one another, or is formed using different materials than one another. In the nonlimiting example illustrated in FIG. 1A, first electrode 111 and second electrode 117 is disposed directly on substrate 101, or alternatively is disposed on substrate 101 via one or more intervening layers (not illustrated).

In one example, the biocompatibility of sensor 110 optionally is further enhanced by providing a biointerface membrane over one or more component(s) of sensor 110. For example, in the nonlimiting configuration illustrated in FIG. 1A, a first biointerface membrane (BM1) 114 is disposed on the ionophore 115 and the first electrode 111. In another example, the first biointerface membrane 114 is disposed on the ionophore 115 and the first electrode 111, and a second biointerface membrane (BM2) 118 is disposed on the second electrode 117. Alternatively, in the nonlimiting configuration illustrated in FIG. 1H, a biointerface membrane (BM) 114' is disposed on both the first electrode 111 and the second electrode 117. Although FIGS. 1A and 1H may suggest that the biointerface membrane(s) have a rectangular shape for simplicity of illustration, it should be apparent that the membrane(s) may conform to the shape of any underlying layers. In some examples, the biointerface membrane(s) is configured to inhibit biofouling of the ionophore 115, the first electrode 111, and/or the second electrode 117. Nonlimiting examples of materials which are included in the biointerface membrane(s) include hard segments and/or soft segments. Examples of hard and soft segments used for the biointerface membrane 114/114'/118 or other biointerface membranes as discussed herein include aromatic polyurethane hard segments with Si groups, aliphatic hard segments, polycarbonate soft segments or any combination thereof. In other examples of biointerface membrane(s) such as 114/114'/118 or other biointerface membranes discussed herein, PVP may not be included. In this example where no PVP is included, the biointerface membrane (118, 114, 114', or other biointerface membranes as discussed herein) may include polyurethane and PDMS. In some examples, which is combined with other examples herein, the biointerface membranes discussed herein may include one or more zwitterionic compounds.

Additionally, or alternatively, the biointerface membrane (s) is configured to release a therapeutic compound into the biological fluid. Therapeutic compounds suitable for release using the biointerface membrane(s) or other membranes as discussed herein may include one or more of anti-inflammatory agents, anti-infective agents, necrosing agents, and anesthetics. Generally, anti-inflammatory agents reduce acute and/or chronic inflammation adjacent to the implant, in order to decrease the formation of a FBC capsule to reduce or prevent barrier cell layer formation. Suitable anti-inflammatory agents include but are not limited to, for example, nonsteroidal anti-inflammatory drugs (NSAIDs) such as acetaminophen, aminosalicylic acid, aspirin, celecoxib, choline magnesium trisalicylate, diclofenac potassium, diclofenac sodium, diflunisal, etodolac, fenoprofen, flurbiprofen, ibuprofen, indomethacin, interleukin (IL)-10, IL-6 mutein, anti-IL-6 iNOS inhibitors (for example, L-NAME or L-NMDA), interferon, ketoprofen, ketorolac, leflunomide, melenamic acid, mycophenolic acid, mizoribine, nabumetone, naproxen, naproxen sodium, oxaprozin, piroxicam, rofecoxib, salsalate, sulindac, and tolmetin; and corticosteroids such as cortisone, hydrocortisone, methylprednisolone, prednisone, prednisolone, betamethesone, beclomethasone dipropionate, budesonide, dexamethasone sodium phosphate, flunisolide, fluticasone propionate, paclitaxel, tacrolimus, tranilast, triamcinolone acetonide, betamethasone, fluocinolone, fluocinonide, betamethasone dipropionate, betamethasone valerate, desonide, desoximetasone, fluocinolone, triamcinolone, triamcinolone acetonide, clobetasol propionate, dexamethasone, and dexamethasone acetate.

Generally, immunosuppressive and/or immunomodulatory agents interfere directly with several key mechanisms necessary for involvement of different cellular elements in the inflammatory response. Suitable immunosuppressive and/or immunomodulatory agents include anti-proliferative, cell-cycle inhibitors, (for example, paclitaxol (e.g., Sirolimus), cytochalasin D, infiximab), taxol, actinomycin, mitomycin, thospromote VEGF, estradiols, NO donors, QP-2, tacrolimus, tranilast, actinomycin, everolimus, methothrexate, mycophenolic acid, angiopeptin, vincristing, mitomycine, statins, C MYC antisense, sirolimus (and analogs), RestenASE, 2-chloro-deoxyadenosine, PCNA Ribozyme, batimstat, prolyl hydroxylase inhibitors, PPARγ ligands (for example troglitazone, rosiglitazone, pioglitazone), halofuginone, C-proteinase inhibitors, probucol, BCP671, EPC antibodies, catchins, glycating agents, endothelin inhibitors (for example, Ambrisentan, Tesosentan, Bosentan), Statins (for example, Cerivasttin), *E. coli* heat-labile enterotoxin, NLRP3 inflammasome inhibitors, and advanced coatings.

Generally, anti-infective agents are substances capable of acting against infection by inhibiting the spread of an infectious agent or by killing the infectious agent outright, which can serve to reduce immuno-response without inflammatory response at the implant site. Anti-infective agents include, but are not limited to, anthelmintics (mebendazole), antibiotics including aminoglycosides (gentamicin, neomycin, tobramycin), antifungal antibiotics (amphotericin b, fluconazole, griseofulvin, itraconazole, ketoconazole, nystatin, micatin, tolnaftate), cephalosporins (cefaclor, cefazolin, cefotaxime, ceftazidime, ceftriaxone, cefuroxime, cephalexin), beta-lactam antibiotics (cefotetan, meropenem), chloramphenicol, macrolides (azithromycin, clarithromycin, erythromycin), penicillins (penicillin G sodium salt, amoxicillin, ampicillin, dicloxacillin, nafcillin, piperacillin, ticarcillin), tetracyclines (doxycycline, minocycline, tetracycline), bacitracin; clindamycin; colistimethate sodium; polymyxin b sulfate; vancomycin; antivirals including acyclovir, amantadine, didanosine, efavirenz, foscarnet, ganciclovir, indinavir, lamivudine, nelfinavir, ritonavir, saquinavir, silver, stavudine, valacyclovir, valganciclovir, zidovudine; quinolones (ciprofloxacin, levofloxacin); sulfonamides (sulfadiazine, sulfisoxazole); sulfones (dapsone); furazolidone; metronidazole; pentamidine; sulfanilamidum crystallinum; gatifloxacin; and sulfamethoxazole/trimethoprim.

Generally, necrosing agents are any drug that causes tissue necrosis or cell death. Necrosing agents include cisplatin, BCNU, taxol or taxol derivatives, and the like.

Generally, vascularization agents include substances with direct or indirect angiogenic properties. In some cases, vascularization agents may additionally affect formation of barrier cells in vivo. By indirect angiogenesis, it is meant that the angiogenesis can be mediated through inflammatory or immune stimulatory pathways. It is not fully known how agents that induce local vascularization indirectly inhibit barrier-cell formation; however it is believed that some barrier-cell effects can result indirectly from the effects of vascularization agents.

Vascularization agents include mechanisms that promote neovascularization around the membrane and/or reduce or minimize periods of ischemia by increasing vascularization close to the device-tissue interface. Sphingosine-1-Phosphate (S1P), which is a phospholipid possessing potent angiogenic activity, is incorporated into a biointerface membrane of a nonlimiting example. Monobutyrin, which is a potent vasodilator and angiogenic lipid product of adipocytes, is incorporated into a biointerface membrane of another nonlimiting example. In another nonlimiting example, an anti-sense molecule (for example, thrombospondin-2 anti-sense), which increases vascularization, is incorporated into a biointerface membrane.

Vascularization agents can include mechanisms that promote inflammation, which is believed to cause accelerated neovascularization in vivo. In one nonlimiting example, a xenogenic carrier, for example, bovine collagen, which by its foreign nature invokes an immune response, stimulates neovascularization, and is incorporated into a biointerface membrane of the present disclosure. In another nonlimiting example, Lipopolysaccharide, which is a potent immunostimulant, is incorporated into a biointerface membrane. In another nonlimiting example, a protein, for example, a bone morphogenetic protein (BMP), which is known to modulate bone healing in tissue, is incorporated into a biointerface membrane.

Generally, angiogenic agents are substances capable of stimulating neovascularization, which can accelerate and sustain the development of a vascularized tissue bed at the device-tissue interface. Angiogenic agents include, but are not limited to, copper ions, iron ions, tridodecylmethylammonium chloride, Basic Fibroblast Growth Factor (bFGF), (also known as Heparin Binding Growth Factor-II and Fibroblast Growth Factor II), Acidic Fibroblast Growth Factor (aFGF), (also known as Heparin Binding Growth Factor-I and Fibroblast Growth Factor-I), Vascular Endothelial Growth Factor (VEGF), Platelet Derived Endothelial Cell Growth Factor BB (PDEGF-BB), Angiopoietin-1, Transforming Growth Factor Beta (TGF-Beta), Transforming Growth Factor Alpha (TGF-Alpha), Hepatocyte Growth Factor, Tumor Necrosis Factor-Alpha (TNF-Alpha), Placental Growth Factor (PLGF), Angiogenin, Interleukin-8 (IL-8), Hypoxia Inducible Factor-I (HIF-1), Angiotensin-Converting Enzyme (ACE) Inhibitor Quinaprilat, Angiotropin, Thrombospondin, Peptide KGHK, Low Oxygen Tension, Lactic Acid, Insulin, Copper Sulphate, Estradiol, prostaglandins, cox inhibitors, endothelial cell binding agents (for example, decorin or vimentin), glenipin, hydrogen peroxide, nicotine, and Growth Hormone.

Generally, pro-inflammatory agents are substances capable of stimulating an immune response in host tissue, which can accelerate or sustain formation of a mature vascularized tissue bed. For example, pro-inflammatory agents are generally irritants or other substances that induce chronic inflammation and chronic granular response at the implantation-site. While not wishing to be bound by theory, it is believed that formation of high tissue granulation induces blood vessels, which supply an adequate or rich supply of analytes to the device-tissue interface. Pro-inflammatory agents include, but are not limited to, xenogenic carriers, Lipopolysaccharides, *S. aureus* peptidoglycan, and proteins.

Other substances that can be incorporated into one or more membranes of the present disclosure include various pharmacological agents, excipients, and other substances well known in the art of pharmaceutical formulations.

Additionally, or alternatively, in some examples, the biointerface membrane(s) (e.g., BM1 114, BM2 118, and/or BM 114') may include a biocompatible polymer and a salt. For example, as illustrated in FIG. 1C, salt 119 is distributed throughout biointerface membrane 118. In one nonlimiting example, the biointerface membrane(s) (e.g., 114, 114', 118) may consist essentially of a biocompatible polymer and a salt. In one example, the biocompatible polymer optionally is present in an amount of about 40 to about 70 weight percent in the biointerface membrane(s). In one example, the salt optionally is present in an amount of about 30 to about 60 weight percent in the biointerface membrane(s). In some examples, the biocompatible polymer is selected from the group consisting of: polyvinyl butyral (PVB) or polyurethane. In certain examples, the biocompatible polymer can be a segmented block copolymer. In one example, the segmented block copolymer may include hard segments and soft segments. In this example, the hard segments may include aromatic or aliphatic diisocyanates are used to prepare hard segments of segmented block copolymer. In one example, the aliphatic or aromatic diisocyanate used to provide hard segment of polymer includes one or more of norbornane diisocyanate (NBDI), isophorone diisocyanate (IPDI), tolylene diisocyanate (TDI), 1,3-phenylene diisocyanate (MPDI), trans-1,3-bis(isocyanatomethyl) cyclohexane (1,3-H6XDI), bicyclohexylmethane-4,4'-diisocyanate (HMDI), 4,4'-diphenylmethane diisocyanate (MDI), trans-1,4-bis(isocyanatomethyl) cyclohexane (1,4-H6XDI), 1,4-cyclohexyl diisocyanate (CHDI), 1,4-phenylene diisocyanate (PPDI), 3,3'-dimethyl-4,4'-biphenyldiisocyanate (TODI), 1,6-hexamethylene diisocyanate (HDI), or combinations thereof.

In one example, the hard segment content is from about 5 wt. % to about 90 wt. % of the segmented block copolymer of the biointerface membrane (e.g., BM1 114, BM2 118, and/or BM 114'). In another example, the hard segments is from about 15 wt. % to about 75 wt. %. In yet another example, the hard segments is from about 25 wt. % to about 55 wt. %. Additionally, or alternatively, the salt optionally is selected from the group consisting of: potassium chloride (KCl), sodium chloride (NaCl), magnesium chloride ($MgCl_2$), calcium chloride ($CaCl_2$), and ammonium sulfate ($(NH_4)_2SO_4$).

It will be appreciated that the biointerface membrane(s) (e.g., BM1 114, BM2 118, and/or BM 114') may include a plurality of layers.

Figure 1I:
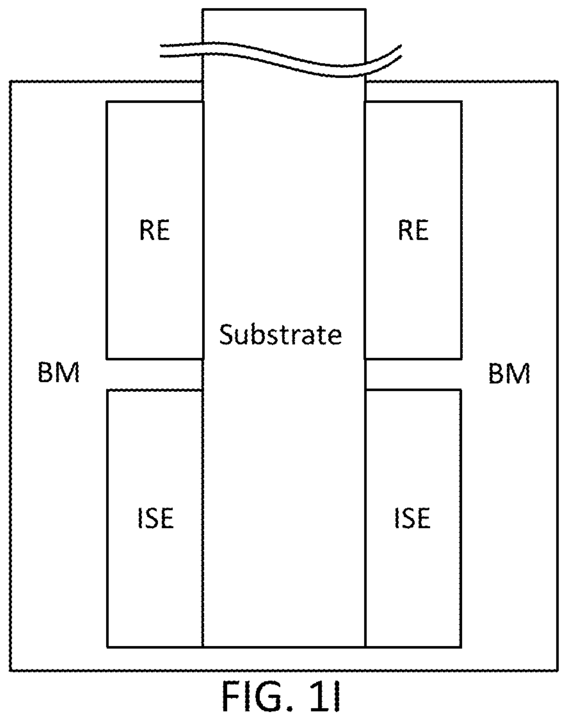

It will further be appreciated that sensor 110 may have any suitable configuration. In the nonlimiting example illustrated in FIG. 1A, substrate 101 is depicted as a planar or substantially planar sensor. FIG. 1D shows a partial plan view of example sensor 110 having a planar substrate 101, the cross-section of which sensor along dotted line 1A-1A corresponds to the view illustrated in FIG. 1A. In other examples, substrate 101 is substantially coaxially shaped and is referred to as a "wire." FIG. 1E shows a partial plan view of example sensor 110 having coaxial substrate 101, the cross-section of which sensor along line 1F-1F corresponds to the view illustrated in FIG. 1F, and the cross-section of which sensor along line 1G-1G corresponds to the view illustrated in FIG. 1G. As noted above, FIG. 1H illustrates an example in which biointerface membrane 114' is disposed over first electrode 111 and second electrode 117. FIG. 1I illustrates a similar example in which biointerface membrane 114' is disposed over first electrode 111 and second electrode 117, and the substrate is wire-shaped.

Figure 2A:
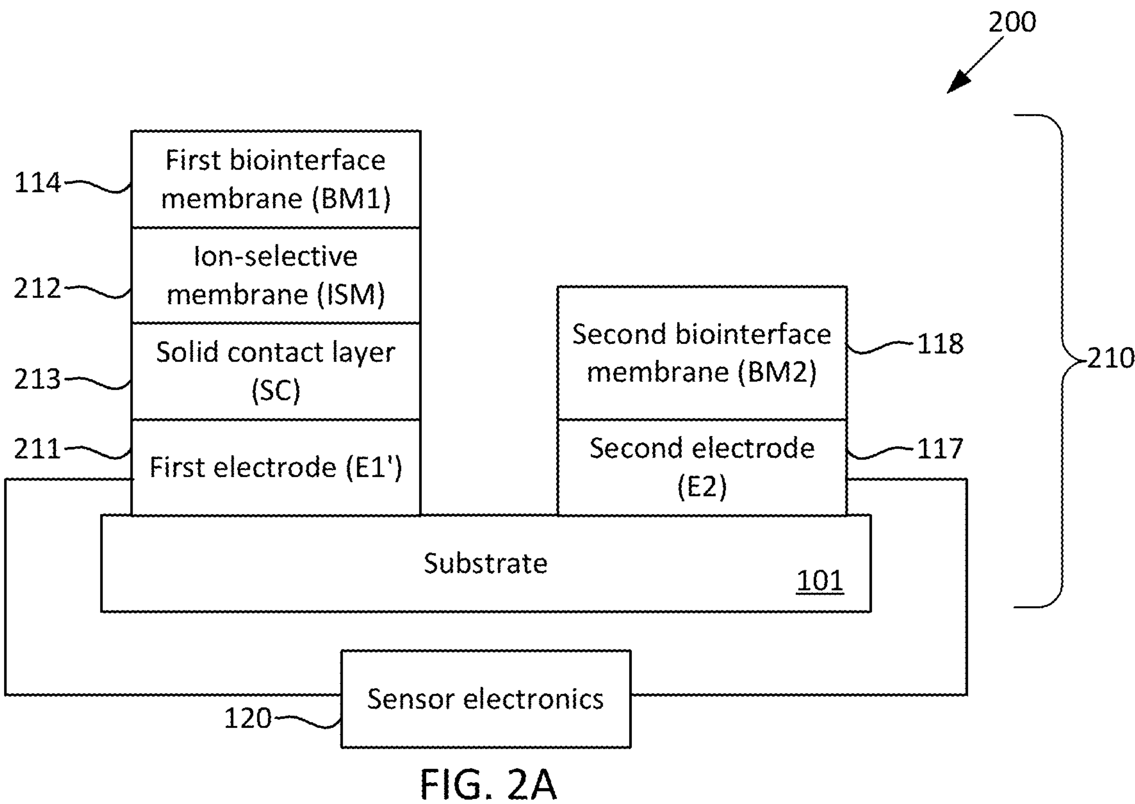

Additionally, the present sensors may include any other suitable number and type of layers. For example, in a manner such as described above with reference to FIGS. 1A and 1B, the ionophore 115 optionally is omitted from first electrode 111. Additionally or alternatively, the ionophore 115 is included in another layer disposed on first electrode 111. For example, FIGS. 2A-2G schematically illustrate additional example configurations and components of a potentiometric sensor. Referring now to FIG. 2A, device 200 includes indwelling sensor 210 and sensor electronics 120. Sensor 210 includes substrate 101 which is configured similarly as described with reference to FIG. 1A, first electrode (E1') 211 disposed on the substrate 101, and a second electrode (E2) 117 disposed on the substrate and which is configured similarly as described with reference to FIG. 1A. First electrode 211 is referred to as a working electrode (WE), while second electrode 117 is referred to as a reference electrode (RE). In one example, the sensor electronics 120 may include circuitry configured to generate a signal corresponding to an electromotive force (EMF). In some examples, the EMF is at least partially based on a potential difference that is generated between the first electrode 211 and the second electrode 117 responsive to biological fluid 10 conducting the signal to first electrode 111, and sensor electronics 120 is configured to use the signal to generate an output corresponding to a measurement of the signal. Additionally, or alternatively, in some examples, device 200 may include an ionophore 115 disposed on the substrate 101 and configured to selectively transport the target ion 11 to the first electrode 211. In one example, the EMF is at least partially based on a potential difference is generated between the first electrode 211 and the second electrode 117 responsive to the ionophore 115 transporting the target ion 11 to the first electrode 211. In one example, the sensor electronics 120 (or an external device to which sensor electronics 120 is configured to transmit the signal via a suitable wired or wireless connection). In one example, the sensor electronics 120 is configured to use the signal to generate an output corresponding to a measurement of the concentration of the target ion in the biological fluid. Further details regarding the configuration and use of sensor electronics 120 are provided further below.

Whereas ionophore 115 is included within first electrode 111 in the example described with reference to FIG. 1A, in the example illustrated in FIG. 2A first electrode 211 does not include ionophore 115 (and thus is referred to as E1' rather than E1). Instead, ionophore 115 is within an ion-selective membrane (ISM) 212 disposed on the first electrode 211. Ionophores 115 may selectively transport target ion 11 to first electrode 211 in a manner similar to that described with reference to FIGS. 1A-1B, and such transport may cause a potential difference between the first electrode 211 and second electrode 117 based upon which sensor electronics 120 may generate an output corresponding to a measurement of the concentration of target ion 11 in biological fluid 10. It will be appreciated that in examples in which device 200 is used to measure an electrophysiological signal and is not used to measure an ion concentration, ISM 212 is omitted.

In a manner similar to that described with reference to first electrode 111, ion-selective membrane 212 substantially excludes any plasticizer, in one example. In some examples, ion-selective membrane 212 may consist essentially of a biocompatible polymer and ionophore 115 configured to selectively bind the target ion. Alternatively, in some examples, the ion-selective membrane 212 consists essentially of a biocompatible polymer, an ionophore 115 configured to selectively bind the target ion 11, and an additive with ion exchanger capability, such as a lipophilic salt. Nonlimiting examples of lipophilic salts, and nonlimiting amounts of additives, biocompatible polymers, and ionophores are provided above with reference to FIGS. 1A-1B.

Whereas first electrode 111 includes a conductive polymer so as to be able to provide ionophore 115 therein while retaining the electrical conductivity of an electrode, additional types of materials is used in ion-selective membrane 212 because the ion-selective membrane 212 need not be used as an electrode. For example, the biocompatible polymer of the ion-selective membrane 212 may include a hydrophobic polymer. Illustratively, the hydrophobic polymer is selected from the group consisting of silicone, fluorosilicone (FS), polyurethane, polyurethaneurea, polyurea. In one example, the biocompatible polymer of the ISM 212 (or other ion-selective membranes or other membranes discussed here) may include one or more block copolymers, which is segmented block copolymers. In one example, the hydrophobic polymer is a segmented block copolymer comprising polyurethane and/or polyurea segments, and/or polyester segments, and one or more of polycarbonate, polydimethylsiloxane (PDMS), methylene diphenyl diisocyanate (MDI), polysulfone (PSF), methyl methacrylate (MMA), poly(ε-caprolactone) (PCL), and 1,4-butanediol (BD). In other examples, the hydrophobic polymer may alternately or additionally include poly(vinyl chloride) (PVC), fluoropolymer, polyacrylate, and/or polymethacrylate.

In one example, the biocompatible polymer may include a hydrophilic block copolymer instead of or in addition to one or more hydrophobic copolymers. Illustratively, the hydrophilic block copolymer may include one or more hydrophilic blocks selected from the group consisting of polyethylene glycol (PEG) and cellulosic polymers. Additionally, or alternatively, the block copolymer may include one or more hydrophobic blocks selected from the group consisting of polydimethylsiloxane (PDMS) polytetrafluoroethylene, polyethylene-co-tetrafluoroethylene, polyolefin, polyester, polycarbonate, biostable polytetrafluoroethylene, homopolymers, copolymers, terpolymers of polyurethanes, polypropylene (PP), polyvinylchloride (PVC), polyvinylidene fluoride (PVDF), polybutylene terephthalate (PBT), polymethylmethacrylate (PMMA), polyether ether ketone (PEEK), polyurethanes, poly(propylene oxide) and copolymers and blends thereof. In one example, the ion-selective membrane 212 does not contain PVP, or other plasticizers.

In one example, the biocompatible polymer of the ion-selective membrane 212 includes from about 0.1 wt. % silicone to about 80 wt. % silicone. In one example, the ion-selective membrane 212, or other ion-selective membranes discussed herein, includes from about 5 wt. % silicone to about 25 wt. % silicone. In yet another example, the ion-selective membrane 212, or other ion-selective membranes discussed herein, includes from about 35 wt. % silicone to about 65 wt. % silicone. In yet another example, the ion-selective membrane 212, or other ion-selective membranes discussed herein, includes from about 30 wt. % silicone to about 50 wt. % silicone.

In certain examples, the ISM 212 or other ISMs discussed herein may include one or more block copolymers or segmented block copolymers. In one example, the segmented block copolymer may include hard segments and soft segments. In this example, the hard segments may include aromatic or aliphatic diisocyanates are used to prepare hard segments of segmented block copolymer. In one example, the aliphatic or aromatic diisocyanate used to provide hard segment of polymer includes one or more of norbornane diisocyanate (NBDI), isophorone diisocyanate (IPDI), tolylene diisocyanate (TDI), 1,3-phenylene diisocyanate (MPDI), trans-1,3-bis(isocyanatomethyl) cyclohexane (1,3-H6XDI), bicyclohexylmethane-4,4'-diisocyanate (HMDI), 4,4'-diphenylmethane diisocyanate (MDI), trans-1,4-bis(isocyanatomethyl) cyclohexane (1,4-H6XDI), 1,4-cyclohexyl diisocyanate (CHDI), 1,4-phenylene diisocyanate (PPDI), 3,3'-Dimethyl-4,4'-biphenyldiisocyanate (TODI), 1,6-hexamethylene diisocyanate (HDI), or combinations thereof. In one example, the hard segments is from about 5 wt. % to about 90 wt. % of the segmented block copolymer of the ISM 212. In another example, the hard segments is from about 15 wt. % to about 75 wt. %. In yet another example, the hard segments is from about 25 wt. % to about 55 wt. %. It will be appreciated that ion-selective membrane 212 and first electrode 111 is prepared in any suitable manner. Illustratively, the polymer, ionophore 115, and any additive is dispersed in appropriate amounts in a suitable organic solvent (e.g., tetrahydrofuran, isopropyl alcohol, acetone, or methyl ethyl ketone). In one example, the mixture is coated onto substrate 101 (or onto a layer thereon) using any suitable technique, such as dipping and drying, spray-coating, inkjet printing, aerosol jet dispensing, slot-coating, electrodeposition, electrospraying, electrospinning, chemical vapor deposition, plasma polymerization, physical vapor deposition, spin-coating, or the like. In one example, the organic solvent is removed so as to form a solid material corresponding to ion-selective membrane 212 or first electrode 111. Other layers in device 100 or device 200, such as electrodes, solid contact layers, and/or biological membranes, is formed using techniques described elsewhere herein or otherwise known in the art.

Whereas first electrode 111 includes a conductive polymer so as to be able to provide ionophore 115 therein while retaining the electrical conductivity of an electrode, additional types of materials is used in first electrode 211. In one example, first electrode can be configured without an ionophore when measuring an electrophysiological signal or with an inactive ionophore that does not electrically interfere with the electrophysiological signal. Nonlimiting example materials for use in first electrode 211 of device 200 are provided above with reference to second electrode 117, e.g., a metal, a metal alloy, a transition metal oxide, a transparent conductive oxide, a carbon material, a doped semiconductor, a binary semiconductor, a ternary semiconductor, or a conductive polymer such as described above with reference to FIG. 1A.

In some examples, the ion-selective membrane is in direct contact with the first electrode. In other examples, such as illustrated in FIG. 2A, sensor 210 further may include a solid contact layer 213 disposed between the first electrode 211 and the ion-selective membrane 212. Solid contact layer 213 may perform the function of enhancing the reproducibility and stability of the EMF by converting the signal into a measurable electrical potential signal. Additionally, or alternatively, solid contact layer 213 may inhibit transport of water from the biological fluid 10 to the first electrode 211 and/or accumulation of water at the first electrode 211. Solid contact layer 213 may include any suitable material or combination of materials. Nonlimiting example materials for use in solid contact layer 213 are provided above with reference to second electrode 117, e.g., a metal, a carbon material (e.g., carbon ink or carbon paste), a doped semiconductor, or a conductive polymer such as described above with reference to FIG. 1A. Alternatively, solid contact layer 213 may include a redox couple which has a well-controlled concentration ratio of oxidized/reduced species that is used to stabilize the interfacial electrical potential. In one example, the redox couple may include metallic centers with different oxidation states. Illustratively, the metallic centers is selected from the group consisting of Co(II) and Co(III); Ir(II) and Ir(III); and Os(II) and Os(III). In alternative examples, the solid contact layer 213 may include a mixed conductor, or mixed ion-electron conductor, such as strontium titanate ($SrTiO_3$), titanium dioxide ($TiO_2$), (La,Ba,Sr)(Mn,Fe,Co)$O_{3-d}$,$La_2CuO_{4+d}$, cerium(IV) oxide ($CeO_2$), lithium iron phosphate ($LiFePO_4$), and $LiMnPO_4$. In one example, the amount of solid contact material present in the solid contact layer is 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, 10 weight percent or more.

Figure 2B:
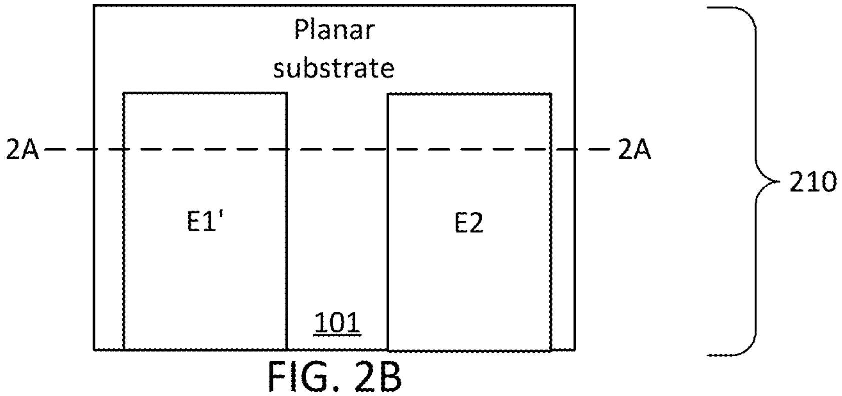
Figure 2F:
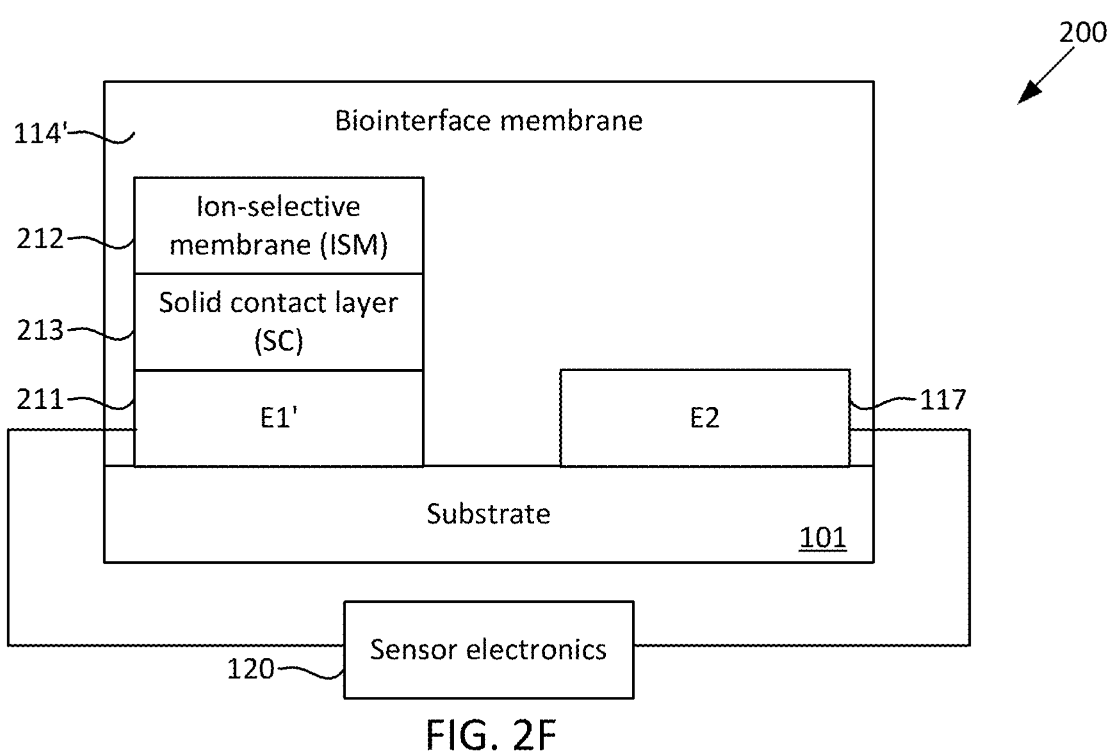
Figure 2G:
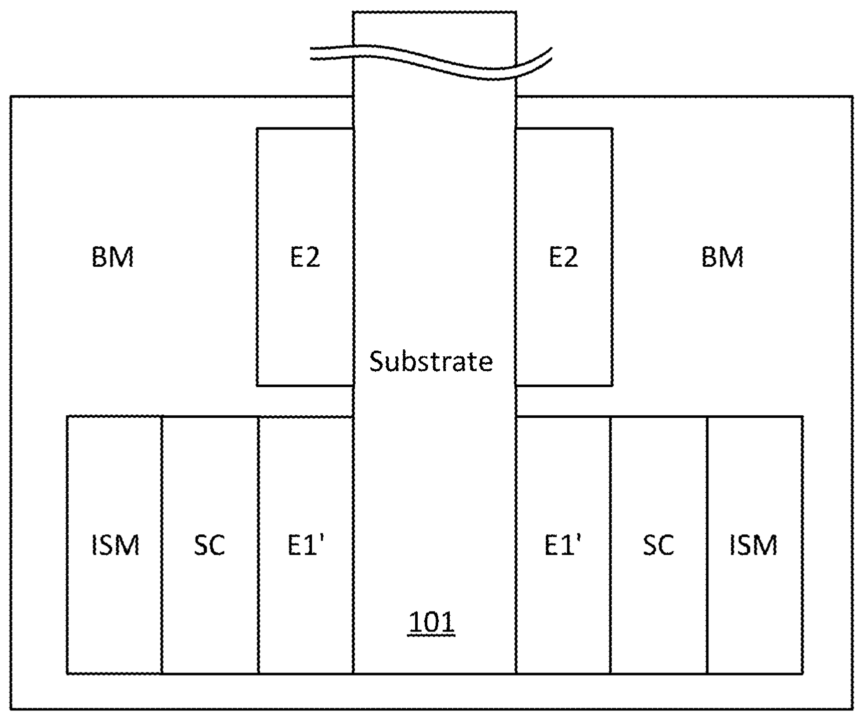

It will further be appreciated that sensor 210 may have any suitable configuration. In the nonlimiting example illustrated in FIG. 2A, substrate 101 is planar or substantially planar. FIG. 2B shows a partial plan view of example sensor 210 having a planar substrate 101, the cross-section of which sensor along dotted line 2A-2A corresponds to the view illustrated in FIG. 2A. In other examples, substrate 101 is substantially wire-shaped, having a coaxial architecture. FIG. 2C shows a partial plan view of example sensor 110 having coaxial substrate 101, the cross-section of which sensor along line 2D-2D corresponds to the view illustrated in FIG. 2D, and the cross-section of which sensor along line 2E-2E corresponds to the view illustrated in FIG. 2E. FIG. 2F illustrates an example in which biointerface membrane 114' is disposed over first electrode 211 and second electrode 117. FIG. 2G illustrates a similar example in which biointerface membrane 114' is disposed over first electrode 211 and second electrode 117, and the substrate is coaxially shaped.

Figure 5A:
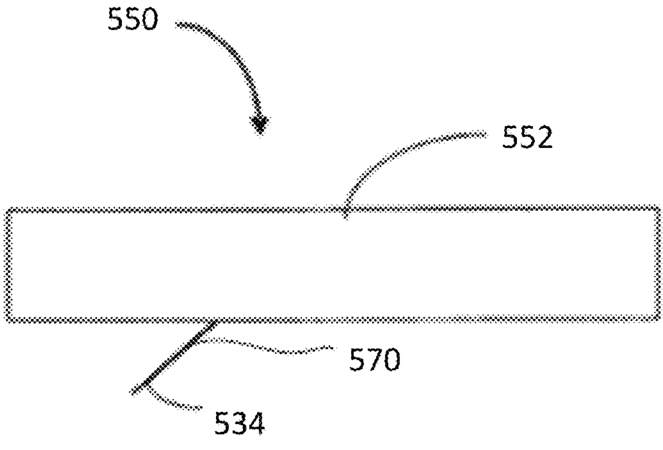
FIGS. 5A-5B schematically illustrate various examples of sensor configurations.

Still other nonlimiting configurations of sensor 110 are described below with reference to FIGS. 5A-5B and 6A-6G. With reference to FIG. 5A a side schematic view of an exemplary transcutaneous analyte sensor 550 is shown. The sensor 550 includes a mounting unit 552 adapted for mounting on the skin of a host, a small (diameter) structure sensor 534 (as defined herein) adapted for transdermal insertion through the skin of a host, and an electrical connection configured to provide secure electrical contact between the sensor and the electronics preferably housed within the mounting unit 552. In general, the mounting unit 552 is designed to maintain the integrity of the sensor in the host so as to reduce or eliminate translation of motion between the mounting unit, the host, and/or the sensor. See co-pending U.S. patent application Ser. No. 11/077,715 filed on Mar. 10, 2005 and entitled, "TRANSCUTANEOUS ANALYTE SENSOR," which is incorporated herein by reference in its entirety. In one example, a drug releasing membrane 570 is formed onto at least a part of the sensor 550.

Figure 5B:
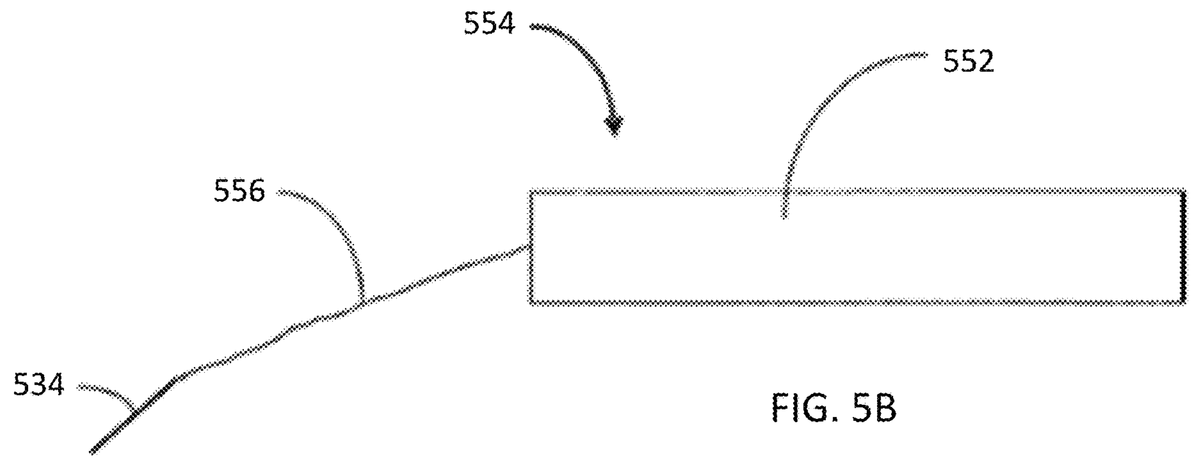

FIG. 5B is a side schematic view of a transcutaneous analyte sensor 554 in an alternative example. The transcutaneous analyte sensor 54 includes a mounting unit 552 wherein the sensing mechanism 536 comprises a small structure as defined herein and is tethered to the mounting unit 552 via a cable 556 (alternatively, a wireless connection can be utilized). The mounting unit is adapted for mounting on the skin of a host and is operably connected via a tether, or the like, to a small structured sensor 534 adapted for transdermal insertion through the skin of a host and measurement of the analyte therein; see, for example, U.S. Pat. No. 6,558,330 to Causey III et al., which is incorporated herein by reference in its entirety.

Sensor electronics 120 is configured to measure an electromotive force based on a potential difference that is generated between a first electrode (e.g., 111 or 211) and a second electrode (e.g., 117). As noted above, in some examples the potential difference is responsive to ionophore 115 transporting target ion 11 to or through first electrode 111 or to first electrode 211. In one example, the corresponding contribution to the electromotive force may substantially logarithmically correspond to the concentration of target ion 11 in biological fluid 10. For example, the EMF generated within sensor electronics 120 responsive to transport of target ion 11 is described using the generalized Nernst relation:

$$E = E^0 - \frac{RT}{zF}\ln\{[I_o]/[I_i]\}$$

where E refers to the electromotive force generated within sensor electronics 120, $E^0$ represents the formal potential of the device 100, R is the universal gas constant, T is the operating temperature (in K), z is the valency or stoichiometric number of electrons partaking in the reaction for each target ion 11 (e.g., 1 for $K^+$, $Na^+$, $NH_4^+$, or $Cl^-$; 2 for $Ca^{2+}$ or $Mg^{2+}$), F is Faraday's constant, $[I_o]$ is the concentration of the target ion 11 in biological fluid 10, and $[I_i]$ is the concentration of the ion within the first electrode 111 or ISM 212. At room temperature, the Nernst relation prescribes that there is a 59.13 mV change in EMF for every $\log_{10}$ (concentration change) (decade) of a target monovalent ion 11 (e.g. $K^+$), or a 29.58 mV change in EMF for every $\log_{10}$ (concentration change) of a target divalent ion 11 (e.g. $Mg^{2+}$).

Because ionophore 115 within first electrode 111, or ISM 212, is highly selective for target ion 11, e.g., in a manner such as described with reference to FIG. 1B, other ions 12, 13, 14, and 15 are expected substantially not to affect the value of the electromotive force which is measured using sensor electronics 120. Nonetheless, in some examples sensor electronics 120 is configured to apply a correction to the above Nernst relation in accordance with the Nicolsky-Shultz-Eisenman equation, which accounts for the effect imparted by the interfering ion $I^b$ on the target ion $I^a$, with $k_{ab}$ referred to as the selectivity coefficient (with lower value being used in some examples, e.g. 1E-2), and $z_b$ is the valency of the interfering ion:

$$E = E^0 - \frac{RT}{z_aF}\ln\left\{[I_0^a]/[I_i^a] + \sum_b\left[k_{ab}\left([I_0^b]/[I_i^b]\right)^{z_a/z_b}\right]\right\}$$

Sensor electronics 120 is configured to provide a high-fidelity measurement of the EMF, based upon which the concentration $[I_0]$ or $$[I_0^a]$$

is calculated using the corresponding equation above. For example, sensor electronics 120 is configured to calculate the selectivity coefficient $k_{ab}$ of a given sensor in the presence of interfering ion $I^b$. In one example, the value of $k_{ab}$ is determined using a fluid with known concentrations of $I^a$ and $I^b$ and measuring the values of E and $E^0$. This relation helps to quantitatively assess the signal generated in the presence of an interfering ion in proportion to the signal generated in the presence of a desired ion at equivalent concentration. For example, a potassium ion sensor with a selectivity coefficient of 0.01 in the presence of sodium would indicate that the sensor is 100× more sensitive to potassium than it is to sodium. Similarly, a physiological level of about 130 mM sodium would approximately equate to a baseline of 1.35 mM added to the potassium signal.

Alternatively, sensor electronics 120 may include circuitry such as a non-volatile computer-readable memory configured to store correlations between control ion concentrations and control signals corresponding to electromotive forces for those control ion concentrations. In one example, the sensor electronics 120 is configured to (a) compare the signal corresponding to the electromotive force to the control signals, (b) select the control signal which most closely matches the signal corresponding to the electromotive force, and (c) generate as the output the control ion concentration which corresponds to the selected control signal. In still other examples, a sensor baseline and sensitivity are characterized at the factory and those are implemented in sensor electronics 120 such that sensor electronics 120 is used to predict baseline and sensitivity over a period of time in vivo. In one example, the period of time during which the predictions are made by the sensor electronics 120 is from one day to 15 or more days.

In some examples, sensor electronics 120 includes a potentiostatic circuit which is configured to control the potential and measure the current as a function of time. In other example, sensor electronics 120 includes a galvanostatic circuit which is configured to control the current (e.g., at near 0 value) and measure the potential as a function of time. In some examples, sensor electronics 120 includes a potentiostatic circuit and a galvanostatic circuit.

In some examples, sensor electronics 120 is configured to sample the potentiometric signal at a sufficiently high sampling rate, e.g., of about 1 Hz or greater, or about 10 Hz or greater, or 100 Hz or greater, or of about 1 kHz or greater, to be able to both measure the concentration of target ion 11 in biological fluid 10 and to measure an electrophysiological waveform of the host. For example, although the DC component of a potentiometric signal is reflective of the concentration of an ion of interest, the AC component of the electrophysiological signal, if acquired with sufficient rapidity (e.g., greater than about 100 Hz, or greater than about 1 kHz), may measure an electrophysiological waveform, namely that associated with potentiation of the heart. As opposed to wet or dry skin-surface electrodes typically employed for electrophysiology, the measurement of electrophysiological signals by an indwelling sensor may produce waveforms of superior fidelity owing to the circumvention of the barrier function of the stratum corneum of the skin. This capability also is used to measure electrophysiological waveforms for extended durations.

For example, the present ion sensor is expected to be significantly more adept at quantifying weak electrophysiological signals with a high degree of fidelity (e.g., signal-to-noise-ratio) than skin-surface electrodes. This is primarily attributed to the high impedance the stratum corneum is known to impart between a skin-surface electrode and the organ/tissue of interest (e.g., heart, brain, muscle); this impedance is on the order of 10s of kilo-ohms. Indwelling sensors, on the other hand, are able to bypass the stratum corneum and, by merit of sensing interstitially, exhibit improved impedance matching characteristics with the organ/tissue of interest, for example on the order of about 10s-100s of ohms. The presence of hair, ointments, or medicaments can also influence signal fidelity of skin-surface electrodes and these electrodes are known to cause skin irritation, sensitization, and allergic response in a noteworthy segment of the population. Furthermore, the longevity of skin-surface electrodes is rather limited, as the gel tends to lose hydration (and chloride ions) over extended durations; these electrodes can also migrate over the skin surface. Although “wet”-type gel electrodes is used to minimize the impedance mismatch, these nevertheless exhibit difficulty approaching the low impedance values characteristic of indwelling sensors, not to mention gel electrodes give rise to undesired gel residue on the skin following removal.

As recognized by the present inventors, the construction and operation of the present solid-state ion-selective sensors share many similar characteristics with electrophysiology sensors. Namely, both utilize at least two electrodes/leads to measure a potential difference and operate under exceptionally low current regimes (oftentimes sub-nanoampere or sub-picoampere); both sensing modalities may use the measurement of an open circuit potential (electromotive force) to infer ion concentration (ion-selective sensors) or organ/tissue activity (electrophysiology sensors). Furthermore, both ion-selective and electrophysiological electrodes is interfaced with an analog front end that exhibits relatively high impedance (e.g., greater than about 1 giga-Ohm, greater than about 10 giga-Ohm, or greater than about 100 giga-Ohm), such as an instrumentation amplifier, differential amplifier, buffer amplifier, unity gain amplifier, or voltage follower. In one example, this front end exhibits low DC offset, low drift, low noise, very high open-loop gain ($G_{OL}$), and very high common-mode rejection ratio (CMRR). Both techniques measure potential changes to infer analyte concentration, as the case with ion-selective electrodes, or organ/tissue activity, as the case with electrophysiological electrodes.

In the case of ion-selective electrodes, an electromotive force (e.g., potential difference) will arise across a semi-permeable membrane (e.g., cell membrane, ion-selective membrane) in solution whenever there is a gradient in the concentration in electroactive species (e.g., ions) across the said membrane, in accordance with the classical Nernst Equation provided further above.

Figure 3:
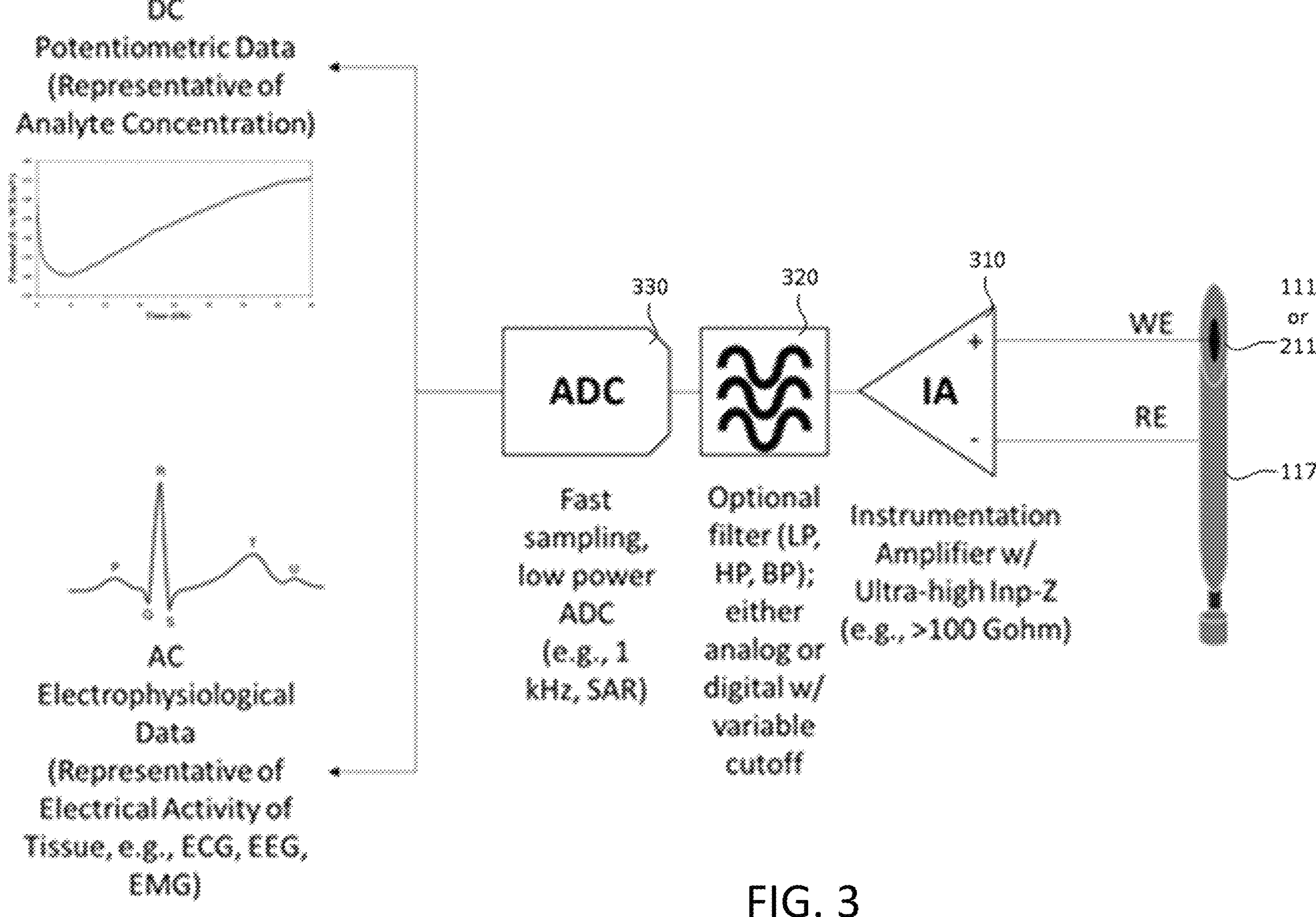
FIG. 3 schematically illustrates example operations and components for use in the present devices and methods to both measure concentration of a target ion in a biological fluid in vivo and measure an electrophysiological signal.

FIG. 3 schematically illustrates example operations and components for use in the present devices and methods to both measure concentration of a target ion in a biological fluid in vivo and measure an electrophysiological signal. As illustrated in FIG. 3, an indwelling, ion-selective sensor such as described with reference to FIG. 1A-1I or 2A-2G, which includes a first electrode (e.g., 111 or 211) and a second electrode (e.g., 117), is used to measure the concentration of an ion of interest while simultaneously recording an electrophysiological waveform. More specifically, whereas measurement of ions in biological matrices is expected to result in very slowly time-varying voltages under practical embodiments, hence giving rise to a “DC” voltage or offset, the measurement of electrophysiologic waveforms, in one example, uses comparatively rapid sampling to acquire the fast temporal dynamics of said “AC” waveforms. To achieve the simultaneous measurement of both signals, a high-impedance amplifier 310 such as mentioned above is used to amplify the potentiometric signal from the sensor. Amplifier 310 may have any suitable configuration, e.g., including an instrumentation amplifier with an ultrahigh input impedance (e.g., greater than about 10 giga-Ohm or greater than about 100 giga-Ohm) as is illustrated in FIG. 3, or include a unity gain amplifier. In one example, an analog-to-digital converter (ADC) 330 is used to quantize the analog, amplified voltage signal into a digital bitstream. To provide reconstruction of the original waveform with high fidelity, Nyquist sampling theory is employed; for example electrophysiological signals, the ADC samples the amplified potentiometric signal with a sampling rate of least about 1 Hz, or at least about 10 Hz, or at least about 100 Hz, e.g., on the order of about 1 kHz. In some examples, this sampling rate can be dynamically adjusted based on maximum frequency content of the waveform. Said ADC, due to rapid sampling, is operated in a power-constrained fashion, either by duty cycling measurement, operating at moderate resolution (e.g., 10- or 12-bit), or employing a low-power architecture (e.g., successive approximation register).

Optionally, a high-pass, low-pass, band-pass, or tunable electrical filter 320 (either analog or digital) is employed to attenuate out-of-band frequencies to isolate the electrophysiological signal(s) or other signals of interest. Optionally, potentiometric recording and electrophysiological recording can be time interleaved. In one half of a duty cycle, a potentiometric measurement is recorded. In the second half of a duty cycle, an electrophysiological measurement is recorded. The duty cycle (period) of this measurement can vary from 1 second to 6 hours. In another embodiment, a low-frequency ADC offering improved resolution (e.g., 14-, 16- or 24-bits) can be employed in parallel with a high-frequency ADC offering de-scaled resolution (e.g., 10- or 12-bits). By way of example a delta-sigma, successive-approximation register, integration, or flash ADC is used, each offering a prescribed effective number of bits (ENOB), signal-to-noise ratio (SNR), jitter, nonlinearity, accuracy, dither, and quantization error characteristic.

From the foregoing, it will be appreciated that a first contribution to the electromotive force from the electrophysiological signal varies rapidly relative to a second contribution to the electromotive force from the concentration of the ion in the physiological fluid. Such difference in time characteristics is used to facilitate deconvolving the first contribution from the second contribution. For example, sensor electronics 120 include a fast Fourier transform (FFT) circuit configured to transform the signal corresponding to the electromotive force from a time domain to the frequency domain. This can also be done in the digital domain, e.g., using an arithmetic logic unit (ALU) in a microprocessor without a dedicated FFT hardware implementation. In some examples, the sensor electronics 120 also include a spectral analysis circuit configured to separate the transformed signal into a high frequency portion corresponding to the first contribution and a low frequency portion corresponding to the second contribution. For example, because the first contribution (from the electrophysiological signal) varies rapidly relative to the second contribution (from the ion concentration), such contributions will occur at different locations in the frequency domain. For example, the low frequency portion is approximately centered at zero frequency, and the high frequency portion may include features at the frequency of a human heartbeat or some harmonic (or subharmonic) thereof, and/or at frequencies corresponding to the features of individual human heartbeats, e.g., about 100 Hz to about 1000 kHz, or about 200 Hz to about 400 Hz. In one example, the spectral analysis circuit or embedded algorithm is configured to separate the contributions in the frequency domain. In one example, the sensor electronics 120 in some examples may include at least one inverse FFT (iFFT) circuit configured to transform the high frequency portion into a time domain output corresponding to the electrophysiological signal and to transform the low frequency portion into a time domain output corresponding to the concentration of the ion in the physiological fluid. It will be apparent that even if only the ion concentration or the electrophysiological signal is measured, similar processing is performed in the frequency domain to isolate the desired signal, e.g., relative to noise, drift, or the like.

In another example, the components are separated from one another in the time domain. For example, sensor electronics 120 may include an analog-to-digital converter (ADC) that digitizes the signal corresponding to the electromotive force. In one example, the sensor electronics 120 also include a first filter configured to receive the digitized signal from the ADC, to remove the second contribution therefrom, and to generate an output corresponding to the first contribution with the second contribution removed. For example, the first filter includes a high-pass filter, band-block filter, or band-pass filter. In some examples, the first filter passes a frequency corresponding to a human heartbeat or heartbeat waveform. In some examples, the sensor electronics 120 also includes a second filter configured to receive the digitized signal from the ADC, to remove the first contribution therefrom, and to generate an output corresponding to the second contribution with the first contribution removed. For example, the second filter includes a low-pass filter, band-block filter, or band-pass filter. In some examples, the second filter passes zero frequency. Note that if the cardiac (AC) signal is basically riding on top of a DC component (the ion signal) it may not be necessary to remove the DC component in order to see and understand the AC component. The DC component would be equivalent to a fixed bias or offset. On the other hand, the DC component is isolated from the AC signal by low-pass filtering the aggregate waveform or performing an averaging of the acquired waveform, thereby smoothing out the AC oscillations. It will be apparent that even if only the ion concentration or the electrophysiological signal is measured, similar processing as provided herein is performed in the frequency domain to isolate the desired signal, e.g., relative to noise, drift, or the like. Additionally, it will be apparent that the processing is performed in the analog domain, e.g., without use of an ADC. For example, sensor electronics 120 includes a first filter configured to remove the second contribution from the signal corresponding to the electromotive force, and to generate a first output corresponding to the first contribution with the second contribution removed; and includes a second filter configured to remove the first contribution from the first output or from the signal corresponding to the electromotive force, and to generate a second output corresponding to the second contribution with the first contribution removed.

In one example, the output generated by sensor electronics 120 is used in any suitable manner. In some examples, sensor electronics 120 include a non-volatile computer-readable memory configured to store the output or a microprocessor or digital signal processor configured to run a signal processing algorithm. Additionally, or alternatively, in some examples, sensor electronics 120 includes a transmitter configured to wirelessly transmit the output, e.g., a near-field communication (NFC), Bluetooth, WiFi, or cellular transmitter. The output is used in any suitable manner, e.g., so as to continuously monitor one or more indicators of the host's heath, and to provide the host with treatment as is appropriate based on the value of the indicator(s).

Further detail regarding sensor electronics 120 now will be provided. The example sensor electronics 120, which is coupled to indwelling sensor 110, the voltage is measured between a first electrode (e.g., 111 or 211) and a second electrode (e.g., 117) using a high input impedance voltmeter or electrometer, otherwise referred to as the measurement system. In some examples, the impedance of potentiometric sensor systems is relatively high (e.g., greater than about 1 GΩ), which means the input impedance of the measurement system must be significantly higher. The error contribution ($E_R$) of the voltage measurement apparatus can be understood by the following equation:

$$E_R = \frac{-R_C}{R_M + R_C} \times 100$$

where $R_C$ is the resistance between the first and second electrodes through the conductive medium (e.g., interstitial fluid) and $R_M$ is the input impedance of the measurement system. For example, if the impedance of the cell and the voltmeter input impedance are equivalent, the error is −50%. However, if $R_M$ is, for example, about 100 times larger than $R_C$, the error decreases to less than about −1%. It is useful to measure impedance of the potentiometric sensor device to understand the instrumentation requirements for the measurement system. Furthermore, it is useful to understand impedance changes in vivo given the probable contributions of bleeding, edema, biofouling, and fibrosis.

Given that voltage is measured continuously as a function of time, analog-to-digital (A/D) conversion is used. An A/D converter digitizes the analog signal into a digital signal, also referred to as "counts" for processing. Accordingly, the resulting raw data stream in counts, also referred to as raw sensor data, is directly related to the voltage measured by the high input impedance voltmeter.

A processor module includes the central control unit that controls the processing of the sensor electronics. In some examples, the processor module includes a microprocessor, however a computer system other than a microprocessor can be used to process data as described herein, for example an application-specific integrated circuit (ASIC), field-programmable gate array (FPGA), or graphical processing unit (GPU) can be used for some or all of the sensor's central processing. In one example, the processor is coupled to a computer-readable memory via which the processor is configured to provide semi-permanent storage of data, for example, storing data such as sensor identifier (ID) and programming to process data streams (for example, programming for data smoothing and/or replacement of signal artifacts similar to that described in U.S. Pat. No. 8,20,174 to Goode et al., incorporated by reference in its entirety herein). The processor additionally can be used for the system's cache memory, for example for temporarily storing recent sensor data. In some examples, the processor module is coupled to one or more computer-readable memory storage components such as ROM, RAM, dynamic-RAM, static-RAM, non-static RAM, EEPROM, rewritable ROMs, flash memory, or the like.

In some examples, the processor module includes a digital filter, for example, an IIR or FIR filter, configured to smooth the raw data stream from the A/D converter. In some examples, digital filters are programmed to filter data sampled at a predetermined time interval (also referred to as a sample rate). In some examples, wherein the voltmeter is configured to measure the analyte at discrete time intervals, these time intervals determine the sample rate of the digital filter. In some alternative examples, wherein the voltmeter is configured to continuously measure the analyte, for example, using a voltage-to-frequency converter as described above, the processor module can be programmed to request a digital value from the A/D converter at a predetermined time interval, also referred to as the acquisition time. In these alternative examples, the values obtained by the processor are advantageously averaged over the acquisition time due the continuity of the voltage measurement. Accordingly, the acquisition time determines the sample rate of the digital filter. In one example, the processor module is configured with a programmable acquisition time, namely, the predetermined time interval for requesting the digital value from the A/D converter is programmable by a user within the digital circuitry of the processor module. An acquisition time of from about 2 seconds to about 512 seconds is used in some examples; however, any acquisition time can be programmed into the processor module. A programmable acquisition time is advantageous in optimizing noise filtration, time lag, and processing/battery power.

Additional signal quality considerations for potentiometric sensors are the contributions of inductive or capacitive electromotive force (EMF) or electromagnetic interference (EMI) and radiofrequency interference (RFI) which can potentially contaminate the voltage signal. For example, mains power line noise (e.g., 50 or 60 Hz and harmonics thereof) may contribute a periodic voltage perturbation, leading to inaccurate concentration reporting. It is expected that voltage amplitudes of these interferences will be small relative to the signal of interest, but it is largely based on the inductance of the sensor components and system, as well as the ambient EM/RF environment. Notably, the lack of coiled or long lengths of wire may reduce or minimize this effect. Another consideration for low voltage measurements is the contribution of thermoelectric or galvanic EMFs, which are largely driven by dissimilar materials in metallic or ionic contact, respectively. A final consideration is biological noise given that the potentiometric sensor also or alternatively used to acquire electrophysiological signals such as electrocardiograms (EKG). It is advantageous to acquire this signal, not only to compensate for its contribution to the potentiometric signal, but also as an additional signature of interest in systemic health monitoring. Further details regarding electrophysiological signals are provided elsewhere herein.

In some examples, the processor module is configured to build the data packet for transmission to an outside source, for example, wired or wireless transmission to a receiver. In some examples, the data packet may include a plurality of bits that can include a sensor ID code, raw data, filtered data, temperature, and/or error detection or correction. The processor module can be configured to transmit any combination of raw and/or filtered data using a wired or wireless connection to an outside source.

In some examples, the analog portion of the A/D converter is configured to continuously measure the voltage difference between the first electrode (e.g., 111 or 211) and second electrode (e.g., 117), and to convert the voltage measurement to digital values representative of the voltage. In one example, the reference electrode of the sensor is biased at or near the expected midpoint of the input voltage range of the A/D converter to maximize quantifiable dynamic range arising from variations in the EMF generated by said sensor.

A battery is operably connected to the sensor electronics and provides the power for the measurement apparatus, though no applied power need be used to drive the potentiometric sensor itself, e.g., the sensor operates galvanically (in contrast to amperometry sensors, which operate electrolytically). In one example, the battery is a lithium manganese dioxide battery; however, any appropriately sized and powered battery can be used (for example, AAA, nickel-cadmium, zinc-carbon, alkaline, lithium, nickel-metal hydride, lithium-ion, zinc-air, zinc-mercury oxide, silver-oxide, silver-zinc, and/or hermetically-sealed). In some examples, the battery is rechargeable, and/or a plurality of batteries can be used to power the system. The indwelling sensor can be powered via an inductive coupling, for example. In some examples, a quartz crystal is operably connected to the processor and maintains system time for the computer system as a whole, for example for the programmable acquisition time within the processor module.

In one example, a temperature probe is provided, where the temperature probe is located on the electronics assembly or the potentiometric sensor itself, as discussed herein. The temperature probe can be used to measure ambient temperature in the vicinity of the sensor. This temperature measurement can be used to add temperature compensation to the calculated concentration (activity) value.

In some examples, output signal (from the sensor electronics) is sent to a receiver (e.g., a computer or other communication station). In one example, the output signal may, in some examples, include a raw data stream that is used to provide a useful value of the measured analyte concentration to a patient or a doctor, for example. In some examples, the raw data stream can be continuously or periodically algorithmically smoothed or otherwise modified to diminish outlying points that do not accurately represent the analyte concentration, for example due to signal noise or other signal artifacts, in a manner such as described in U.S. Pat. No. 8,10,174 to Goode et al., which is incorporated herein by reference in its entirety.

When a sensor is first implanted into host tissue, the sensor and receiver are initialized. This can be referred to as start-up mode, and involves optionally resetting the sensor data and calibrating the sensor. In selected examples, mating the electronics unit to the mounting unit triggers a start-up mode. In other examples, the start-up mode is triggered by the receiver. In one example, the presently disclosed sensors are calibrated individually and sensitivities and $E_0$ of the individual sensors are used to predict in vivo performance and/or reduce data dispersion within lots.

In some examples, the sensor electronics are wirelessly connected to a receiver via one- or two-way RF transmissions or the like. However, a wired connection is also contemplated. The receiver provides much of the processing and display of the sensor data, and can be selectively worn and/or removed at the host's convenience. Thus, the sensor system can be discreetly worn, and the receiver, which provides much of the processing and display of the sensor data, can be selectively worn and/or removed at the host's convenience. Particularly, the receiver includes programming for retrospectively and/or prospectively initiating a calibration, converting sensor data, updating the calibration, evaluating received reference and sensor data, and evaluating the calibration for the analyte sensor, in a manner such as described in U.S. Pat. No. 7,778,680, which is incorporated herein by reference in its entirety.

FIGS. 6A through 6C illustrate one aspect (e.g., the in vivo portion) of a continuous analyte sensor 600, which includes an elongated conductive body 602 (which is referred to as a substrate). The elongated conductive body 602 includes a core 610 (see FIG. 6B) and a first layer 612 at least partially surrounding the core 610. The first layer 612 includes a working electrode (e.g., located in window 606) and a membrane 608 located over the working electrode configured and arranged for multi-axis bending. In some examples, the core 610 and first layer 612 can be of a single material (e.g., platinum). In some examples, the elongated conductive body 602 is a composite of at least two materials, such as a composite of two conductive materials, or a composite of at least one conductive material and at least one non-conductive material. In some examples, the elongated conductive body 602 includes a plurality of layers. In certain examples, there are at least two concentric (e.g., annular) layers, such as a core 610 formed of a first material and a first layer 612 formed of a second material. However, additional layers can be included in some examples. In some examples, the layers are coaxial.

In one example, the elongated conductive body 602 is long and thin, yet flexible and strong. In one example, the smallest dimension of the elongated conductive body 602 is less than about 0.1 inches, 0.75 inches, 0.5 inches, 0.25 inches, 0.1 inches, 0.075 inches, 0.01 inches, 0.004 inches, or 0.002 inches. While the elongated conductive body 602 is illustrated in FIGS. 6A through 6C as having a circular cross-section, in other examples the cross-section of the elongated conductive body 602 can be ovoid, rectangular, triangular, polyhedral, star-shaped, C-shaped, T-shaped, X-shaped, Y-Shaped, irregular, or the like. In one example, a conductive wire electrode is employed as the core 610. To such a clad electrode, two additional conducting layers is added (e.g., with intervening insulating layers provided for electrical isolation). In one example, the conductive layers may include any suitable material. In certain examples, it can be desirable to employ a conductive layer including conductive particles (i.e., particles of a conductive material) in a polymer or other binder.

In certain examples, the materials used to form the elongated conductive body 602 (e.g., stainless steel, titanium, tantalum, platinum, platinum-iridium, iridium, certain polymers, and/or the like) can be strong and hard, and therefore are resistant to breakage. In one example, the ultimate tensile strength of the elongated conductive body 602 is from about 80 kPsi to about 500 kPsi. In another example, in some examples, the Young's modulus of the elongated conductive body 602 is from about 660 GPa to about 220 GPa. In still another example, the yield strength of the elongated conductive body 602 is from about 60 kPsi to about 2200 MPa. Ultimate tensile strength, Young's modulus, and yield strength are discussed in greater detail elsewhere herein. In some examples, the sensor's small diameter provides (e.g., imparts, enables) flexibility to these materials, and therefore to the sensor as a whole. Thus, the sensor can withstand repeated forces applied to it by surrounding tissue. One measurement of the sensor's ability to withstand the implantation environment is fatigue life. In some examples, the fatigue life of the sensor is at least 1,000 cycles of flexing of from about 280 to about 110° at a bend radius of about 0.125-inches.

In addition to providing structural support, resiliency and flexibility, in some examples, the core 610 (or a component thereof) provides electrical conduction for an electrical signal from the working electrode to sensor electronics (not shown), which are described elsewhere herein.

In some examples, the core 610 includes a conductive material, such as stainless steel, titanium, tantalum, a conductive polymer, and/or the like. However, in other examples, the core 610 is formed from a non-conductive material, such as a non-conductive polymer. In yet other examples, the core 610 includes a plurality of layers of materials. For example, in one example the core 610 includes an inner core and an outer core (not shown here) that is arranged concentrically. In a further example, the inner core is formed of a first conductive material and the outer core is formed of a second conductive material. In one example, the first conductive material is stainless steel, titanium, tantalum, a conductive polymer, an alloy, and/or the like, and the second conductive material is conductive material selected to provide electrical conduction between the core 610 and the first layer 612, and/or to attach the first layer 612 to the core 610 (e.g., if the first layer 612 is formed of a material that does not attach well to the core material). In another example, the core 610 is formed of a non-conductive material (e.g., a non-conductive metal and/or a non-conductive polymer) and the first layer 612 is a conductive material, such as stainless steel, titanium, tantalum, a conductive polymer, and/or the like. The core 610 and the first layer 612 can be of a single (or same) material, e.g., platinum. One skilled in the art appreciates that additional configurations are possible.

Referring again to FIGS. 6A-6C, in some examples, the first layer 612 is formed of a conductive material. The working electrode is an exposed portion of the surface of the first layer 612. Accordingly, the first layer 612 is formed of a material configured to provide a suitable working electrode, a material such as but not limited to platinum, platinum-iridium, gold, palladium, iridium, graphite, carbon, a conductive polymer, an alloy and/or the like.

As shown in FIG. 6B-6C, a second layer 604 surrounds a least a portion of the first layer 612, thereby defining the boundaries of the working electrode. In some examples, the second layer 604 serves as an insulator and is formed of an insulating material, such as polyimide, polyurethane, parylene, or any other known insulating materials. For example, in one example the second layer is disposed on the first layer 612 and configured such that the working electrode is exposed via window 606. In another example, an elongated conductive body 602, including the core 610, the first layer 612 and the second layer, is provided, and the working electrode is exposed (i.e., formed) by removing a portion of the second layer, thereby forming the window 606 through which the working electrode (e.g., the exposed surface of the first layer 612) is exposed. In some examples, the working electrode is exposed by (e.g., window 606 is formed by) removing a portion of the second and (optionally) third layers. Removal of coating materials from one or more layers of elongated conductive body 602 (e.g., to expose the working electrode) can be performed by hand, excimer lasing, chemical etching, laser ablation, grit-blasting, or the like.

In some examples, the sensor further includes a third layer 614 including a conductive material. In further examples, the third layer may include a reference electrode, which in some examples is formed of a material that is applied onto the second layer (e.g., an insulator) or other material such as described elsewhere herein. The third layer can be processed using a pasting/dipping/coating step, for example, using a die-metered dip coating process, and then the body can be drawn through a die to meter the coating to a precise thickness. In some examples, multiple coating steps are used to build up the coating to a predetermined thickness. Such a drawing method can be utilized for forming one or more of the electrodes in the device depicted in FIG. 6B.

In some examples, the elongated conductive body 602 further includes one or more intermediate layers located between the core 610 and the first layer 612. In one example, the intermediate layer is an insulator, a conductor, a polymer, and/or an adhesive.

It is contemplated that the ratio between the thickness of the electrode layer and the thickness of an insulator (e.g., polyurethane or polyimide) layer can be controlled, so as to allow for a certain error margin (e.g., an error margin associated with the etching process) that would not result in a defective sensor (e.g., due to a defect resulting from an etching process that cuts into a depth more than intended, thereby unintentionally exposing a working electrode). This ratio is different depending on the type of etching process used, whether it is laser ablation, grit blasting, chemical etching, or some other etching method. In one nonlimiting example, the ratio of the thickness of the electrode layer and the thickness of the insulator layer can be from about 1:5 to about 1:1, or from about 1:3 to about 1:2.

In certain example, the core 610 includes a non-conductive polymer and the first layer 612 includes a conductive material. Such a sensor configuration can sometimes provide reduced material costs, in that it replaces a typically expensive material with an inexpensive material. In one example, the core 610 is formed of a non-conductive polymer, such as, a nylon or polyester filament, string or cord, which can be coated and/or plated with a conductive material, such as platinum, platinum-iridium, gold, palladium, iridium, graphite, carbon, a conductive polymer, and allows or combinations thereof.

As shown in FIGS. 6C and 6D, the sensor also includes a membrane 608 covering at least a portion of the working electrode. Membranes are discussed elsewhere herein.

FIG. 6B is a schematic illustrating an elongated conductive body 602 (also referred to as the "elongated body") in one example, wherein the elongated conductive body 602 is formed from at least two materials and/or layers of conductive material, as described in greater detail elsewhere herein. In some examples, the term "electrode" can be used herein to refer to the elongated conductive body 602, which includes the portion of the electrode that detects the analyte. In some examples, the elongated conductive body 602 provides an electrical connection between the working electrode and sensor electronics (not shown). In certain examples, each electrode (e.g., the elongated conductive body 602, on which the working electrode is located) is formed from a fine wire with a diameter of from about 0.001 inches or less to about 0.01 inches or more, for example, and is formed from, e.g., a plated insulator, a plated wire, or bulk electrically conductive material. For example, the wire and/or elongated conductive body 602 used to form a working electrode includes a diameter and/or a smallest dimension (e.g., width) of about 0.05, 0.08, 0.10, 1.27, 0.15, 0.18, 0.20, 0.23, 0.25, 0.38, 0.51, 0.64, 0.76, 0.89, 1.02 or 1.14 mm (0.002, 0.003, 0.004, 0.005, 0.006, 0.007, 0.008, 0.009, 0.01, 0.015, 0.02, 0.025, 0.03, 0.035, 0.04 or 0.045 inches).

In some examples, the first electrode includes a wire formed from a conductive material, such as platinum, platinum-iridium, palladium, graphite, gold, carbon, conductive polymer, alloys, or the like.

In some examples, the working electrode is formed of platinum-iridium or iridium wire. In general, platinum-iridium and iridium materials are generally stronger (e.g., more resilient and less likely to fail due to stress or strain fracture or fatigue). While not wishing to be bound by theory, it is believed that platinum-iridium and/or iridium materials can facilitate fabrication of a wire with a smaller diameter to further decrease the maximum diameter (size) of the sensor (e.g., in vivo portion). Advantageously, with respect to intravascularly-implanted sensors, a smaller sensor diameter both reduces the risk of clot or thrombus formation (or other foreign body response) and allows the use of smaller catheters.

Referring to FIG. 6B, in some examples, the elongated conductive body 602 includes at least two concentric layers (e.g., a composite structure). In a further example, the elongated conductive body 602 includes a core 610 and a first layer 612. The core 610 is formed from one of the at least two materials referred to above. For example, the core 610 can be formed of a polymer, a metal, an alloy and the like. In some examples, the core 610 is formed from a conductive polymer, such as but not limited to polyaniline and polypyrrole. In some examples, a conductive material is added to (e.g., mixed with and/or applied to) a non-conductive polymer, whereby the polymer core is rendered conductive. In one example, one or more conductive metals (e.g., carbon, gold, platinum, iridium, etc.), such as but not limited to particles, can be mixed with the uncured polymer, which can be formed into the core 610.

In other examples, the core 610 can include an inner core and an outer core, in some examples. For example, platinum, iridium or gold particles can be ion-implanted on the surface of a polymer inner core, such that the particles form an outer core. For example, a polymer filament fiber can be ion-implanted with gold, such that the treated filament fiber is conductive. In some examples, the core 610 is formed from a metal, such as but not limited to at least one of stainless steel, tantalum, titanium and/or an alloy thereof. For example, in one example, the core 610 is formed of an extruded stainless steel, tantalum, titanium and/or an extruded alloy. In some examples, the material of the core 610 is processed to provide the strength and flexibility necessary for multi-axis bending. Processing the metal changes its properties, such as but not limited to by compressing and/or rearranging the metal's crystalline lattice. For example, tempering can make a metal less brittle and more springy; hardening can make a metal hold its shape better. Accordingly, in certain examples, the core 610 is formed of a metal that has been processed to provide the requisite combination of strength and flexibility (e.g., an ultimate tensile strength of from about less than 80, 80, 90, 100, 110, 120, 130, 140 or 150 kPsi (551 MPa) to about 160, 170, 180, 190, 200, 210, 220 or 500 kPsi (3297 MPa)) or more. In one example, the core 610 is formed from a metal that has been annealed, tempered, normalized, hardened, work-hardened, full-processed, case hardened, draw air hardened, cold worked and/or the like, to render it more stiff. In one example, the core 610 is formed from full-processed platinum. In another example, the core 610 is formed from work-hardened platinum-iridium.

In some examples, the surface of the elongated conductive body 602 and/or the core 610 is treated to remove initiation sites (e.g., locations/points of irregularity, where sensor breaking tends to begin), to smooth and/or clean the surface, to prepare it for application of the next material, and/or the like. Suitable treatments include but are not limited to electro-polishing, etching, application of a tie layer, electro-deposition, and electrostatic deposition.

In some examples, the elongated conductive body 602 (and/or the core 610, and/or the sensor) is wire-shaped. However, the wire-shape can include one of a variety of cross-sectional shapes, such as but not limited to a circle, an oval, a rectangle, a triangle, a cross, a star, a cloverleaf, an X-shape, a C-shape, an irregular or other non-circular configuration, and the like. The elongated conductive body 602 includes a diameter and/or a smallest dimension (e.g., width) of about 0.05, 0.08, 0.10, 1.27, 0.15, 0.18, 0.20, 0.23, 0.25, 0.38, 0.51, 0.64, 0.76, 0.89, 1.02 or 1.14 mm (0.002, 0.003, 0.004, 0.005, 0.006, 0.007, 0.008, 0.009, 0.01, 0.015, 0.02, 0.025, 0.03, 0.035, 0.04 or 0.045 inches). The elongated conductive body 602 can be provided as a reel and/or extended lengths that are subsequently processed and/or singularized into individual sensor lengths.

In some examples, the elongated conductive body 602 includes a first layer 612 applied to a core 610. In some examples, the first layer 612 is applied to the core 610 such that they are electrically connected (e.g., in electrical contact, such that a current can pass therebetween). The first layer 612 can be formed of a variety of conductive materials, such as but not limited to at least one of platinum, platinum-iridium, gold, palladium, iridium, graphite, carbon, conductive polymers and an alloy. In certain examples, the first layer 612 is relatively thin, such as but not limited to a thickness of from about less than 50, 50, 55, 60, 65, 70, 75, 80, 85, 90, 95 or 100 micro-inches to about 125, 150, 175, 200, 225, 250, 275 or 300 micro-inches, or thicker. As is described elsewhere herein with greater detail, at least a portion of the surface of the first layer 612 provides the working electrode. For example, as described herein, in some examples, the working electrode is exposed through a window formed in the insulator. In some examples, the surface of the applied first layer 612 is treated prior to application of membrane materials, such as to optimize the surface for membrane attachment and for function as a working electrode. For example, the surface can be cleaned, smoothed, etched, and the like. Advantageously, forming the conductive core 610 of an inexpensive yet strong and flexible inner body with a thin layer of the potentially costlier working electrode material may provide for a substantial reduction in material costs.

In some examples, a conductive paste including a mixture of material (e.g., an ink) and one or more membrane components is applied to the layer surrounding the core 610, or applied directly to the core 610. In one example, the conductive paste may include, for example, an ionophore, additive, polymer, and/or enzyme. Use of the conductive the paste may reduce or eliminate the need for certain membrane layers (e.g., a separate electrode layer, a separate ionophore layer, and/or a separate enzyme layer).

The first layer 612 can be applied to the core 610 using a variety of manufacturing methods. In one example, the first layer 612 is co-extruded with the core 610 using known techniques, such as but not limited to metal-on-metal or metal-on-polymer extrusion techniques. Some useful co-extrusion techniques are described in U.S. Pat. Nos. 7,416,802, 7,268,562, 7,153,458, 7,280,879, 5,324,328 and 6,434,430, the entire contents of each of which are incorporated by reference herein. In one example, a stainless steel inner body (not shown here) is co-extruded with a platinum first layer 612, such as but not limited to through a die, to form a thin reel of 0.005-inch diameter wire having a stainless steel core with a 100-micro-inch layer of platinum thereon.

In some examples, the first layer 612 is applied to the core 610 (which, in some examples, is pre-treated as described above) using a thin film or thick film technique (e.g., spraying, electro-depositing, vapor-depositing, dipping, spin coating, sputtering, evaporation, printing or the like). For example, in one example, the first layer 612 is applied by dipping the core 610 into a solution of the first layer 612 material and drawing out the core 610 at a speed that provides the appropriate first layer 612 thickness. However, any known thin or thick film method can be used to apply the first layer 612 to the core 610, as will be appreciated by one skilled in the art. Some examples of thin and/or thick film manufacturing techniques can be found in U.S. Patent Application Publication No. US-2005-0181012-A1, U.S. Patent Application Publication No. US-2006-0036143-A1, U.S. Patent Application Publication No. US-2007-0163880-A1, U.S. Patent Application Publication No. US-2006-0270923-A1, U.S. Patent Application Publication No. US-2007-0027370-A1, U.S. Patent Application Publication No. US-2006-0015020-A1, U.S. Patent Application Publication No. US-2006-0189856-A1, U.S. Patent Application Publication No. US-2007-0197890-A1, U.S. Patent Application Publication No. US-2006-0257996-A1, U.S. Patent Application Publication No. US-2006-0229512-A1, U.S. Patent Application Publication No. US-2007-0173709-A1, U.S. Patent Application Publication No. US-2006-0253012-A1, U.S. Patent Application Publication No. US-2006-0195029-A1, U.S. Patent Application Publication No. US-2008-0119703-A1, U.S. Patent Application Publication No. US-2008-0108942-A1, and U.S. Patent Application Publication No. US-2008-0200789-A1, the entire contents of each of which are incorporated by reference herein.

In some examples, the first layer 612 is deposited onto the core 610. In one example, the first layer 612 is plated (e.g., electroplated) onto the core 610. In one example, a thin layer of platinum is plated onto a tantalum core by immersing the inner body in a platinum-containing solution and applying a current to the inner body for an amount of time, such that the desired thickness of platinum first layer 612 is generated and/or achieved. Description of deposition methods and devices therefore can be found in U.S. Pat. Nos. 7,427,338, 7,425,877, 7,427,560, 7,351,321 and 7,384,532, the entire contents of each of which are incorporated by reference herein.

In still other examples, the core 610 is embedded in insulator and a working electrode body 612 is attached, such that the core 610 and the working electrode body are electrically (e.g., functionally, operably) connected, such as described in U.S. Pat. No. 8,828,201, the entire contents of which are incorporated by reference herein. In one example, a working electrode body is formed as a foil that is attached to the core 610, such as with adhesive, welding and/or an intermediate layer of conductive material to provide adhesion between the core 610 and the working electrode body material (e.g., at tie layer). In some examples, multiple layers are applied on top of the core 610. In some examples, each layer possesses a finite interface with adjacent layers or together forms a physically continuous structure having a gradient in chemical composition. In another example, the working electrode body is a C-clip or snap-ring that is attached by compression about and/or around the core 610. In some examples, the working electrode body is attached over a window. In other examples, there is no window, instead, the working electrode body is configured to pierce the insulator and to physically contact the underlying core 610, such that the working electrode body and the core are operably connected. In some examples, a conductive metal C-clip is attached to the core 610 with adhesive, welding and/or a tie layer. In yet another example, an adhesive is attached to the core 610, followed by wrapping a conductive foil there-around.

The elongated conductive body 602 can be manufactured using a variety of manufacturing techniques. In some examples, the first layer 612 is applied to the core 610 in a substantially continuous process. In one example, the manufacturing of the elongated conductive body 602 involves a reel-to-reel process. In other examples, a sheet-fed technique is used. In some examples, application of the first layer 612 to the core 610 can be by either a semi-automated or fully-automated process. Automation of some or all manufacturing steps generally requires the use of one or more machines, such as robotic devices, that are configured and arranged to perform the manufacturing step(s). In some examples, one manufacturing step can be automated, such as production of the elongated conductive body 602. However, in other examples, two or more of the manufacturing steps can be automated. For example, a device can be configured to perform two or more of the steps, or two or more devices can perform the steps. In some examples, when multiple devices are used, the devices are connected, coupled together, interconnected, and linked functionally and/or physically. In one example, the product of one device is fed directly into the next device, and so on. In one example, a reel of previously manufactured core 610, such as a stainless-steel, tantalum or titanium wire, can be fed substantially continuously through a device configured to electroplate the core 610 with platinum, gold, carbon or the like, such that a reel of plated wire is generated. For example, a manufacturing device and/or system can be configured to automatically co-extrude stainless-steel and platinum to generate/produce a reel of wire-shaped elongated conductive body 602 including a stainless-steel core and platinum first layer (e.g., the first layer 612). Examples of continuous manufacturing processes can be found in U.S. Pat. Nos. 6,103,33, 5,879,828, 5,714,391, 7,429,552, 7,402,349 and 7,387,811, the entire contents of each of which are incorporated by reference herein.

In a further example, the first layer 612 includes a working electrode (e.g., the portion exposed through the window 606). For example, if the sensor is configured to detect an analyte other than an ion, the analyte enzymatically reacts with an enzyme in the membrane covering at least a portion of the working electrode, whereas the enzyme can generate ions from the analyte, the concentration of which can be measured using ionophores and the working electrode in a manner such as described elsewhere herein. Or, for example, if the sensor is configured to detect an ion, the concentration of the ion can be measured using the ionophore and working electrode in a manner such as described elsewhere herein.

As described with reference to FIG. 6A and as shown in FIG. 6C, an insulator 604 is disposed on (e.g., located on, covers) at least a portion of the elongated conductive body 602. In some examples, the sensor is configured and arranged such that the elongated body includes a core 610 and a first layer 612, and a portion of the first layer 612 is exposed via window 606 in the insulator. In other examples, the sensor is configured and arranged such that the elongated body includes a core embedded in an insulator, and a portion of the core 610 is exposed via the window in the insulator. In one example, the insulating material is applied to the elongated body (e.g., screen-, ink-jet and/or block-printed) in a configuration designed to leave a portion of the first layer's 612 surface (or the core's 610 surface) exposed. For example, the insulating material can be printed in a pattern that does not cover a portion of the elongated body. In another example, a portion of the elongated body is masked prior to application of the insulating material. Removal of the mask, after insulating material application, exposes the portion of the elongated body.

In some examples, the insulating material 604 includes a polymer, for example, a non-conductive (e.g., dielectric) polymer. Dip-coating, spray-coating, vapor-deposition, printing and/or other thin film and/or thick film coating or deposition techniques can be used to deposit the insulating material on the elongated conductive body 602 and/or core 610. In one example, the insulating material is applied as a layer of from about less than 5, 5, 60 or 65-microns to about 20, 25, 30 or 35-microns or more in thickness. In some examples, the insulator is applied as a single layer of material. In other examples, the insulator is applied as two or more layers, which are included of either the same or different materials. In some examples, the insulating material includes at least one of polyurethane, polyimide and parylene. In one example, the insulating material includes parylene, which can be an advantageous polymer coating for its strength, lubricity, and electrical insulation properties. Generally, parylene is produced by vapor deposition and polymerization of para-xylylene (or its substituted derivatives). However, any suitable insulating material, such as but not limited to a dielectric ink, paste or paint, can be used, for example, fluorinated polymers, polyethyleneterephthalate (PET), polyurethane, polyimide, other nonconducting polymers, or the like. In some examples, glass or ceramic materials can also be employed. Other materials suitable for use include surface energy modified coating systems such as are marketed under the trade names AMC18, AMC148, AMC141, and AMC321 by Advanced Materials Components Express of Bellefonte, Pa. In some alternative examples, however, the core 610 is conductive and may not require a coating of insulator. In some examples a surface of the conductive core (e.g., a portion of the first layer 612) either remains exposed during the insulator application or a portion of applied insulator is removed to expose a portion of the core's 610 surface, as described above.

In some examples, in which the sensor has an insulated elongated body, a portion of the insulating material is stripped or otherwise removed, for example, by hand, excimer lasing, chemical etching, laser ablation, grit-blasting (e.g., with sodium bicarbonate or other suitable grit), or the like, to expose the working electrode. In one example, grit blasting is implemented to expose working electrode, for example, by utilizing a grit material that is sufficiently hard to ablate the polymer material yet also sufficiently soft so as to minimize or avoid damage to the underlying metal electrode (e.g., a platinum electrode). Although a variety of "grit" materials can be used (e.g., sand, talc, walnut shell, ground plastic, sea salt, and the like), in some examples, sodium bicarbonate is an advantageous grit-material because it is sufficiently hard to ablate, e.g., a parylene coating without damaging, e.g., an underlying platinum conductor. One additional advantage of sodium bicarbonate blasting includes its polishing action on the metal as it strips the polymer layer, thereby eliminating a cleaning step that might otherwise be necessary. In some examples, the opening in the insulator, through which the surface of the first layer 612 is exposed, is referred to as a "window" 606.

Due to the small sizes of the sensors in some examples, it can be difficult to precisely remove the insulator over one insulated conductive core without affecting, and possibly removing, the insulator over an adjacent conductive core or over other parts of the sensor. However, in some examples, the insulator is configured such that the precision of laser ablation is substantially improved. In one example, the insulator is configured such that two different types of lasers can be used to ablate separate portions of the insulator. For example, if the insulators of two elongated bodies are different materials (i.e. one is polyurethane and another is a fluoropolymer such as TEFLON® or another type of polytetrafluoroethylene), then it is possible to selectively ablate the insulator off of one of the elongated bodies and to not remove insulator from the other elongated body in the same region of the sensor. In some examples, the two insulation materials require different laser parameters for optimal ablation, such that a first laser setup could be used to ablate a first material but not the second material, and a second laser setup could be used to ablate a second material but not the first material. In another example, for a sensor containing two elongated bodies, the insulator covering one elongated body can be configured for laser ablation with an ultraviolet laser (e.g., using a wavelength of about 200 nm), and the other elongated body can be configured for laser ablation with an infrared laser (e.g., using a wavelength of about 1000 nm). In another example, the insulator materials are selected such that the insulator of a first elongated body requires a substantially higher laser power to be ablated than the insulator of a second elongated body. For example, the insulator over the two elongated bodies can be the same, except that the insulator of the first elongated body is thicker than the insulator of the second elongated body. In another example, the insulator on each of the elongated bodies has a different thickness, such that a single laser is used to remove the insulator over both cores, except that the window in the thinner insulator is formed more quickly than the window in the thicker insulator. For example, the insulator of one elongated body can be from about 0.0001 inches to about 0.0003 inches in thickness, and the insulator of one elongated body can be from about 0.0008 inches to about 0.0010 inches in thickness. In yet another example, a colorant can be added to the insulator of one of the elongated bodies, to modify the amount of energy that is absorbed from the laser. For example, adding a dark colorant or other absorptive material to the first insulator but not the second insulator can cause the first insulator to absorb much more energy of the laser than the non-colored second insulator. In this way, a small amount of laser energy would ablate one wire but not the other, but a large amount of laser energy would ablate both. As is understood by one skilled in the art, the setup of the laser can be adjusted, to fine-tune the insulator removal process. For example, the laser pulse width and power level can be adjusted to modify and/or modulate the amount of insulator removed, the rate of removal, and/or the like. This principle can be used for assemblies (e.g., sensors) of three or more elongated bodies (e.g., cores, wires). The same principle is applied to chemical ablation, where different solvents are required for the different insulation layers such that they can be selectively ablated. The same principle may also be used with plasma ablation, where different plasma settings or amounts of energy are required to ablate the different materials.

In the examples illustrated in FIGS. 6A and 6C, a radial window 606 is formed through the insulating material 604 to expose a circumferential surface of the working electrode (e.g., first layer 612). In other examples, such as described in U.S. Pat. No. 8,828,201, a radial or non-radial window 606 is formed (e.g., for electrical connection to the working electrode body e.g., first layer 612) by removing only a portion of the insulating material 604. Additionally, a surface of the reference electrode 614 is exposed, in some examples (not shown). For example, the sections of surface can be masked during deposition of an outer insulating layer and/or etched after deposition of an outer insulating layer. In some examples, a plurality of micro-windows includes the surface of the working electrode, wherein the sum of the micro-window surface areas is substantially equal to the window 606 surface area. In certain examples, the plurality of micro-windows is spaced and/or staggered along a length of the core 610.

In some examples, the window 606 (or the working electrode body, e.g., the first layer 612) is sized to provide a working electrode having an area such that the sensor has a suitable sensitivity. In some examples, the working electrode has a diameter of from about 0.001 inches or less to about 0.01 inches or more, or from about 0.002 inches to about 0.008 inches, or from about 0.004 inches to about 0.005 inches. The length of the window can be from about 0.1 mm (about 0.004 inches) or less to about 2 mm (about 0.078 inches) or more, or from about 0.5 mm (about 0.2 inches) to about 0.75 mm (0.3 inches). In such examples, the exposed surface area of the working electrode is from about 0.000013 $in^2$ (0.0000839 $cm^2$) to about 0.0025 $in^2$ (0.016129 $cm^2$) (assuming a diameter of from about 0.001 inches to about 0.01 inches and a length of from about 0.004 inches to about 0.078 inches).

In some examples, the exposed surface area of the working electrode (and/or other electrode) (e.g., conductive core/the core 610) can be increased by altering the cross-section of the electrode itself. In one example the cross-section of the working electrode can be defined by a cross, star, cloverleaf, ribbed, dimpled, ridged, irregular, or other non-circular configuration; thus, for any predetermined length of electrode, a specific increased surface area can be achieved (as compared to the area achieved by a circular cross-section). Increasing the surface area of the working electrode can be advantageous in providing an increased signal responsive to the analyte concentration, which in turn can be helpful in improving the signal-to-noise ratio, for example. In some examples, application of the insulator to the conductive core can be accomplished by a substantially continuous process, which can be semi- or fully-automated, such as in a manner similar to some methods described for formation/manufacture of the conductive core.

In some examples, the analyte sensor 600 further includes a reference electrode 614. The reference electrode 614, which can function as a reference electrode alone, or as a dual reference and counter electrode, is formed using a material such as described elsewhere herein. In some examples, the reference electrode 614 is juxta positioned and/or twisted with or around at least a portion of the sensor. For example, in a manner such as described in U.S. Pat. No. 8,828,201, the reference electrode is helically twisted and/or wrapped and/or wound around the working electrode. This assembly of "wires" is then optionally coated or adhered together with an insulating material, similar to that described above, so as to provide an insulating attachment.

Referring to FIGS. 6B-6C, in some examples, the reference electrode 614 includes a material applied over at least a portion of the insulating material 604. In some examples, the material is applied using thin film and/or thick film techniques, such as but not limited to dipping, spraying, printing, electro-depositing, vapor deposition, spin coating, and sputter deposition, as described elsewhere herein. For example, a conductor-containing paint (or similar formulation) is applied to a reel of the insulated conductive core, in one example. In another example, the reel of insulated elongated body (or core) is cut into single unit pieces (e.g., "singularized") and a conductor-containing ink is pad printed thereon. In still other examples, the material is applied as a foil. For example, an adhesive can be applied to an insulated elongated body, around which the foil is then wrapped. Alternatively, the sensor can be rolled in conductive particles, such that a sufficient amount of conductor sticks to and/or embeds into and/or otherwise adheres to the adhesive for the particles to function as the reference electrode. In some examples, the sensor's reference electrode includes a sufficient amount of conductor that the sensor measures and/or detects the analyte for at least three days.

In some examples, the sensor is formed from an elongated body (e.g., elongated conductive body 602), such as that shown in FIG. 6B, wherein the elongated body includes a core 610, a first layer 612 for use in a working electrode, an insulator 604, and a layer of material 614 for use in a reference electrode. In some examples, such as that shown in FIG. 6C, the surface of the elongated body (e.g., also the surface of the first layer 612) is exposed by formation of a window 606 through both the material of the reference electrode and the insulator. In one example, the elongated body of FIG. 6B is provided as an extended length on a reel that is singularized into a plurality of pieces having a length (e.g., less than 0.5, 0.5, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5 or 24-inch or longer lengths) suitable for a selected sensor configuration. For example, a first sensor configured for transcutaneous implantation can employ 2.5-inch lengths, while a second sensor configured for transcutaneous implantation can employ 3-inch lengths. In another example, a first sensor configured for implantation into a peripheral vein of an adult host can employ a 3-inch length, while a second sensor configured for implantation into a central vein of an adult host can employ a 12-inch length. The window is formed on each sensor, such as by scraping and or etching a radial window through the material of the reference electrode and the insulator such that the platinum surface is exposed (e.g., the surface of the "working electrode"). In some examples, a reel of elongated body is singularized and then the windows are formed. In other examples, the windows are formed along the length of the reel of elongated body, and then later singularized. In a further example, additional manufacturing steps are performed prior to singularization. A membrane 608 is positioned on the exposed surface (e.g., the working electrode) defined by the edges of the window, such that the surface can function as the working electrode of the sensor to generate a signal associated with an analyte, e.g., ion (e.g., when the sensor is in contact with a sample of a host). Alternative manufacturing techniques and/or sequences of steps can be used to produce sensors having the configuration shown in FIG. 6C, such as but not limited to masking a portion of the elongated body (or core) prior to application of the insulator and the material for use in the reference electrode.

FIG. 6B is an illustration showing layers cut away, but in the fabrication process the material typically obtained has all layers ending at a tip. A step of removing layers 604 and 614 can be performed so as to form window(s). FIG. 6D illustrates the results of this removal/cutting away process through a side-view/cross-section. The removal process can be accomplished by the methods already described or other methods as known in the art. In one example the removal step is conducted, e.g., by laser skiving, and can be performed in a reel-to-reel process on a continuous strand. The removed area can be stepped, for example, by removing different layers by different lengths (FIG. 6D). In such a fabrication method involving a continuous strand, the sensors can be singularized after the removal step. In some examples, if the core is a metal, an end cap is employed, e.g., by dipping, spraying, shrink tubing, crimp wrapping, etc., an insulating or other isolating material onto the tip. If the core is a polymer (e.g., hydrophobic material), an end cap may not be necessary. For example, in the sensor depicted in FIG. 6D, an end cap 620 (e.g., of a polymer or an insulating material) or other structure is provided over the core (e.g., if the core 610 is not insulating). FIG. 6E can be considered to build on a general structure as depicted in FIG. 6B, in that two or more additional layers are added to create one or more additional electrodes. Methods for selectively removing two or more windows to create two or more electrodes can also be employed. For example, by adding another conductive layer 622 and insulating layer 624 under a reference electrode layer 614, then two electrodes (first and second working electrodes) can be formed, yielding a dual electrode sensor. The same concept can be applied to create a counter electrode, electrodes to measure additional analytes or ions, and the like, for example. FIG. 6F illustrates a sensor having an additional electrode 622 (as compared to FIGS. 6B-6D), wherein the windows are selectively removed to expose working electrodes 612, 622 in between a reference electrode (including multiple segments) 614, with a small amount of insulator 604, 624 exposed therebetween. FIG. 6G illustrates another example, wherein selective removal of the various layers is stepped to expose the electrodes 612, 622 and insulators 604, 624 along the length of the elongated body.

Figures 4A, 4B:
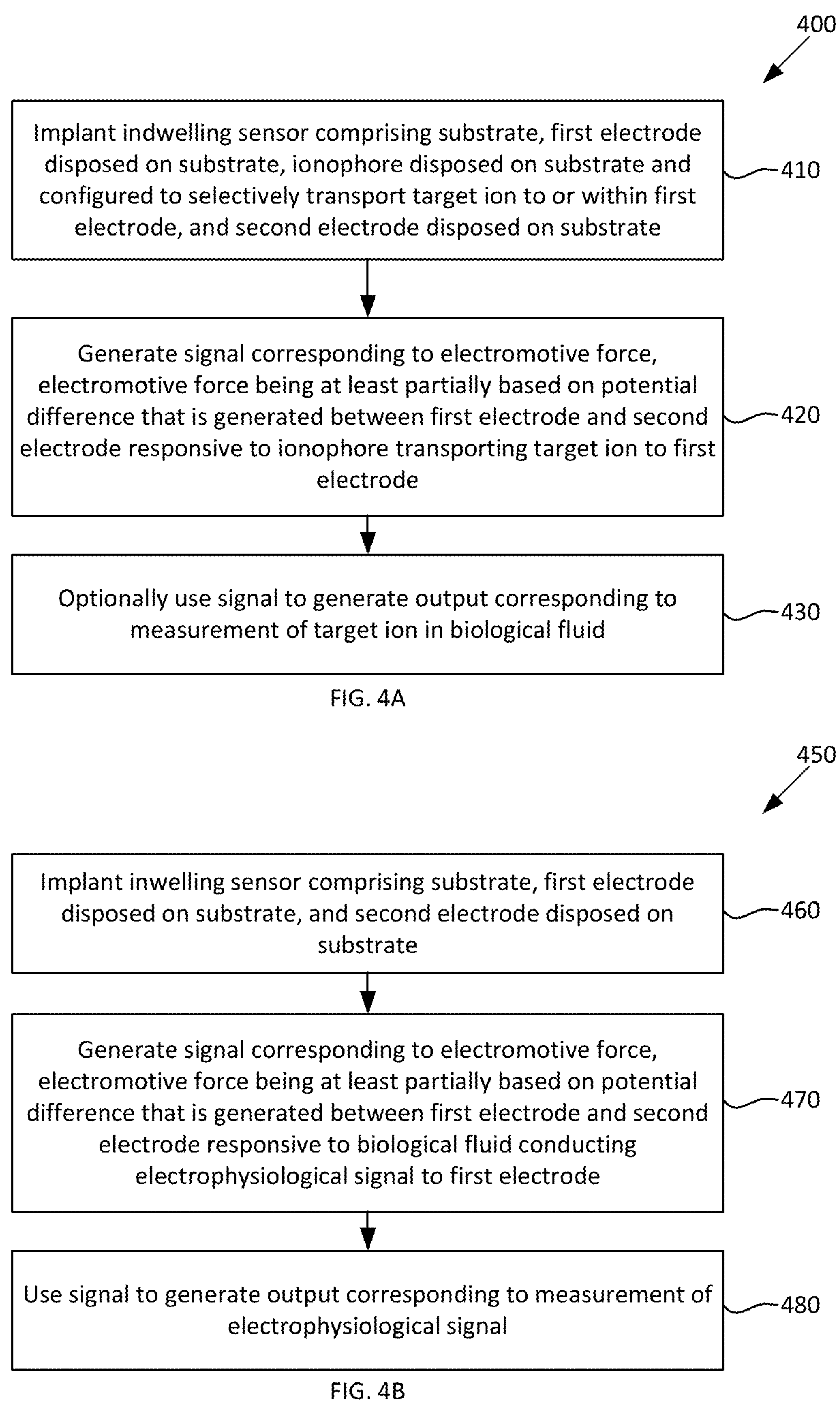
FIG. 4A illustrates a flow of operations in an example method for measuring a concentration of a target ion in a biological fluid in vivo.
FIG. 4B illustrates a flow of operations in an example method for measuring an electrophysiological signal that is conducted via a biological fluid in vivo.

FIG. 4A illustrates a flow of operations in an example method 400 for measuring a concentration of a target ion in a biological fluid in vivo. Method 400 illustrated in FIG. 4A may include implanting an indwelling sensor (operation 410). In preferred embodiments, the indwelling sensor is implanted transcutaneously. In other embodiments, the indwelling sensor is implanted subcutaneously or intracutaneously. In a manner such as described with reference to FIG. 1A-1I or 2A-2G, the sensor may include a substrate (e.g., 101); a first electrode disposed on the substrate (e.g., 111 or 211); an ionophore (e.g., 115) disposed on the substrate and configured to selectively transport the target ion to or within the first electrode; and a second electrode (e.g., 117) disposed on the substrate. Nonlimiting options of these and other components of the sensor are provided elsewhere herein. Method 400 illustrated in FIG. 4A also may include generating a signal corresponding to an electromotive force, the electromotive force being at least partially based on a potential difference that is generated between the first electrode and the second electrode responsive to the ionophore transporting the target ion to the first electrode (operation 420). For example, sensor electronics 120 may generate the signal in a manner such as described with reference to FIG. 1A-1L, 2A-2G, 3, 5A-5B, or 6A-6G. Method 400 illustrated in FIG. 4A optionally also may include using the signal to generate an output corresponding to a measurement of the concentration of the target ion in the biological fluid (operation 430). For example, sensor electronics 120 may generate the output, or may transmit the signal to an external device which generates the output, in a manner such as described with reference to FIGS. 1A-1I, 2A-2G, 3, 5A-5B, and 6A-6G.

FIG. 4B illustrates a flow of operations in an example method 450 for measuring an electrophysiological signal that is conducted via a biological fluid in vivo. Method 450 illustrated in FIG. 4B includes implanting an indwelling sensor (operation 460). In a manner such as described with reference to FIG. 1A-1I or 2A-2G, the sensor may include a substrate (e.g., 101); a first electrode (e.g., 111 or 211) disposed on the substrate; and a second electrode (e.g., 117) disposed on the substrate. Method 450 illustrated in FIG. 4B also may include generating a signal corresponding to an electromotive force, the electromotive force being at least partially based on a potential difference that is generated between the first electrode and the second electrode responsive to the biological fluid conducting the electrophysiological signal to the first electrode (operation 470). For example, sensor electronics 120 may generate the signal in a manner such as described with reference to FIG. 1A-1I, 2A-2G, 3, 5A-5B, 6A-6G, or 7A-7C. Method 450 illustrated in FIG. 4B optionally also may include using the signal to generate an output corresponding to a measurement of the electrophysiological signal (operation 480). For example, sensor electronics 120 may generate the output, or may transmit the output to an external device, in a manner such as described with reference to FIG. 1A-1I, 2A-2G, 3, 5A-5B, 6A-6G, or 7A-7C.

It should be clear from the present disclosure that operations described with reference to FIG. 4A optionally is combined with respective operations from FIG. 4B, and that operations described with reference to FIG. 4B optionally is combined with respective operations from FIG. 4A. For example, operations 410 and 460 is combined, e.g., such that the indwelling sensor which is implanted includes ionophore 115 (e.g., within first electrode 111 or within ISM 212). Additionally, operations 420 and 470 is combined, e.g., such that the signal is generated corresponding to an electromotive force which is partially based on a potential difference that is generated between the first and second electrodes responsive to the ionophore transporting the target ion 11 to the first electrode, and which is partially based on a potential difference that is generated responsive to the biological fluid conducting the electrophysiological signal to the first electrode. Additionally, operations 430 and 480 is combined, e.g., such that the signal is used to generate an output corresponding to the measurement of the target ion in the biological fluid, and an output corresponding to measurement of the electrophysiological signal.

Figures 7A, 7B:
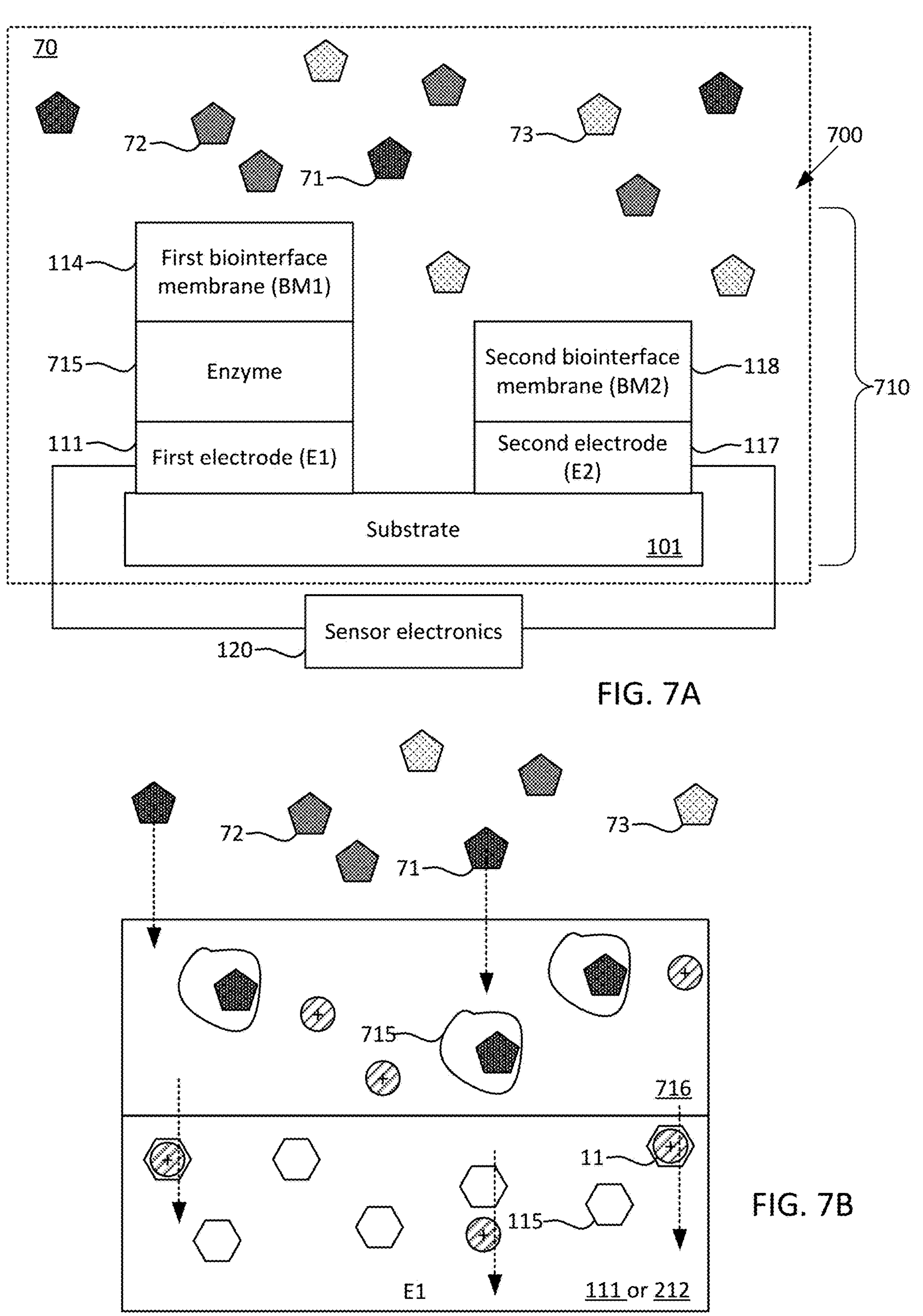
FIGS. 7A-7C schematically illustrate example configurations and components of a device for measuring an electrophysiological signal and/or concentration of a target analyte in a biological fluid in vivo.
Figure 7C:
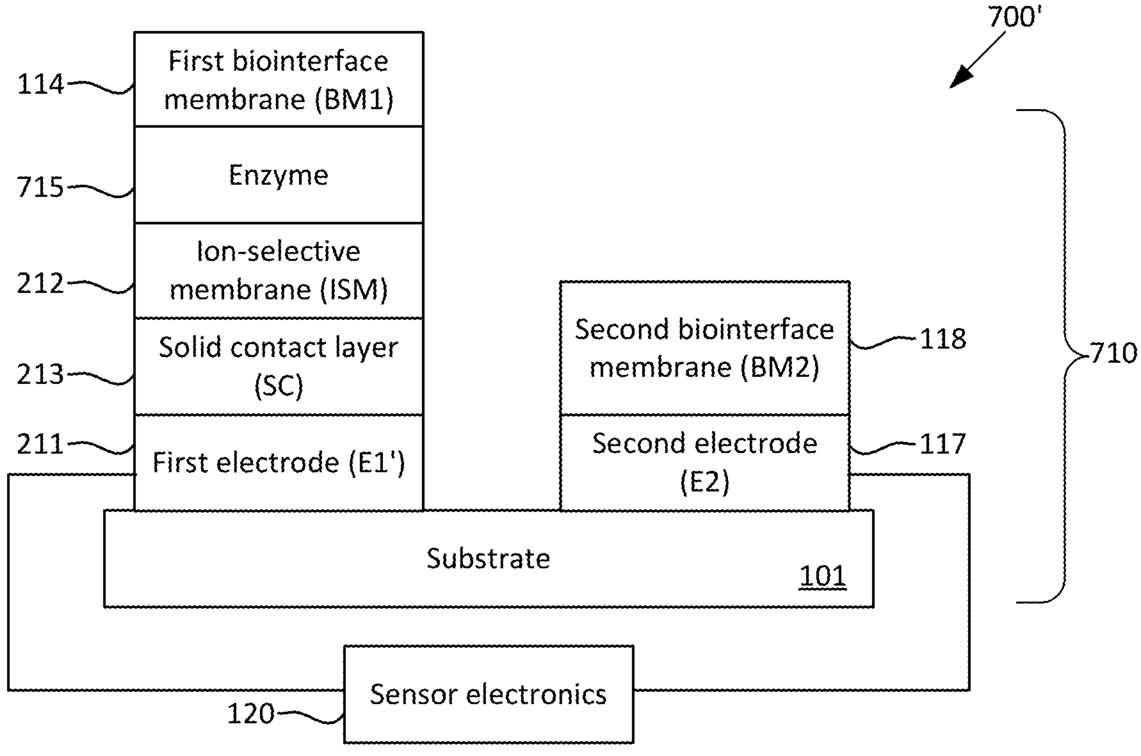

It will be apparent that sensors such as described with referred FIGS. 1A-1I, 2A-2G, 3, 5A-5B, and 6A-6G and methods such as described with reference to FIGS. 4A-4B suitably is adapted for use in measuring a concentration of any suitable analyte. For example, FIGS. 7A-7C schematically illustrate example configurations and components of a device for measuring an electrophysiological signal and/or concentration of a target analyte in a biological fluid in vivo. Similarly as described with reference to FIG. 1A, device 700 includes indwelling sensor 710 and sensor electronics 120. Similarly as described with reference to FIG. 1A, device 700 includes indwelling sensor 710 and sensor electronics 120. Indwelling sensor 710 includes substrate 101 which is configured similarly as described with reference to FIG. 1A, an ionophore disposed on the substrate and configured to selectively transport a target ion to or within the first electrode, an enzyme 715 configured to generate the target ion responsive to acting upon the target analyte, and a second electrode (E2) 117 disposed on the substrate and which is configured similarly as described with reference to FIG. 1A. In one example, the enzyme 715 is located in a material similar to that of to first electrode 111 of FIG. 1A (optionally omitting the ionophore) or similar to that of ion-selective membrane 212 of FIG. 1B (optionally omitting the ionophore).

In the nonlimiting example illustrated in FIG. 7A, the ionophore is located within first electrode (E1) 111 disposed on the substrate and is configured similarly as described with reference to FIG. 1A. Alternatively, in the nonlimiting example illustrated in FIG. 7C, the ionophore is located within ion-selective membrane 212 which is configured in a manner such as described with reference to FIG. 2A, and the first electrode 211 is configured in a manner such as described with reference to FIG. 2A. First electrode 111 or 211 is referred to as a working electrode (WE), while second electrode 117 is referred to as a reference electrode (RE).

In one example, the sensor electronics 120 is configured to generate a signal corresponding to an electromotive force (EMF). In some examples, the EMF is at least partially based on a potential difference that is generated between the first electrode and the second electrode responsive to the ionophore transporting the target ion to the first electrode. In one example, the sensor electronics 120 is configured to use the signal to generate an output corresponding to a measurement of the concentration of the target ion in the biological fluid, and/or is configured to transmit the signal to an external device configured to use the signal to generate an output corresponding to a measurement of the concentration of the target ion in the biological fluid. Optionally, in some examples, the EMF is at least partially based on a potential difference that is generated between the first electrode and the second electrode responsive to biological fluid 10 conducting the electrophysiological signal to first electrode 111, and sensor electronics 120 is configured to use the signal to generate an output corresponding to a measurement of the electrophysiological signal.

In a manner such as illustrated in FIG. 7A, biological fluid 10 may include a plurality of analytes 71, 72, and 73. Device 700 is configured to measure the concentration of analyte 71, and accordingly such analyte is referred to as a "target" analyte. As illustrated in FIG. 7B, enzyme 715 is located within enzyme layer 716, and may selectively act upon target analyte 71 from biological fluid 10 or from biointerface membrane 114 (if provided, e.g., as illustrated in FIG. 7A and configured similarly as described with reference to FIGS. 1A, 2A, and optionally configured similarly as biointerface membrane 114' such as described with reference to FIGS. 1H-1I). The action of enzyme 715 upon the target analyte 71 generates the target ion 11. Ionophore 115 within first electrode 111 or within ion-selective membrane 212 may selectively transport, or selectively bind, target ions 11 from enzyme 715 to and within first electrode 111 or first electrode 211.

It will be appreciated that target analyte 71 is any suitable analyte, enzyme 715 is any suitable enzyme that generates a suitable ion responsive to action upon that analyte, and ionophore 115 is any suitable ionophore that selectively transports and/or binds that ion generated by enzyme 715 so as to generate an EMF such that the concentration of analyte 71 is determined (whether using sensor electronics 120 or an external device to which the sensor electronics 120 transmits the electrophysiological signal and/or signal corresponding to ion concentration). Nonlimiting examples of analytes, enzymes, and ionophores that is used together are listed below in Table 1.

TABLE 1

Enzymatic Potentiometric Sensor Constructs

| Analyte | Enzyme | Ion generated | Ionophore |
|---|---|---|---|
| Urea | Urease | Ammonium | Nonactin |
| Glucose | Glucose oxidase | H+ (via peroxide) | Tridodecylamine, 4-Nonadecylpyridine, N,N-Dioctadecylmethylamine, Octadecyl isonicotinate, Calix[4]-aza-crown |
| Creatinine | Creatinine deaminase | Ammonium | Nonactin |
| Lactate | Lactate oxidase | H+ (via peroxide) | Tridodecylamine, 4-Nonadecylpyridine, N,N-Dioctadecylmethylamine, Octadecyl isonicotinate, |

TABLE 1-continued

| Enzymatic Potentiometric Sensor Constructs | | | |
|---|---|---|---|
| Analyte | Enzyme | Ion generated | Ionophore |
| | | | Calix[4]-aza-crown |
| Cholesterol | Cholesterol oxidase | H+ (via peroxide) | Tridodecylamine, 4-Nonadecylpyridine, N,N-Dioctadecylmethylamine, Octadecyl isonicotinate, Calix[4]-aza-crown |
| Glutamate | Glutamate oxidase/ Glutamate dehydrogenase | Ammonium | Nonactin |
| Galactose | Galactose/ oxidase | H+ (via peroxide) | Tridodecylamine, 4-Nonadecylpyridine, N,N-Dioctadecylmethylamine, Octadecyl isonicotinate, Calix[4]-aza-crown |
| Ketone (β-hydroxy-butyrate (BHB)) | β-hydroxybutyrate dehydrogenase + NADH oxidase | H+ (via peroxide) | potassium ionophore I (valinomycin), potassium ionophore II (BB15C5), potassium ionophore III (BME44) or 2-dodecyl-2-methyl-1,3-propanediyl bis[N-[5'-nitro(benzo-15-crown-5)-4'-yl]carbamate] (BME44) |

Figure 8:
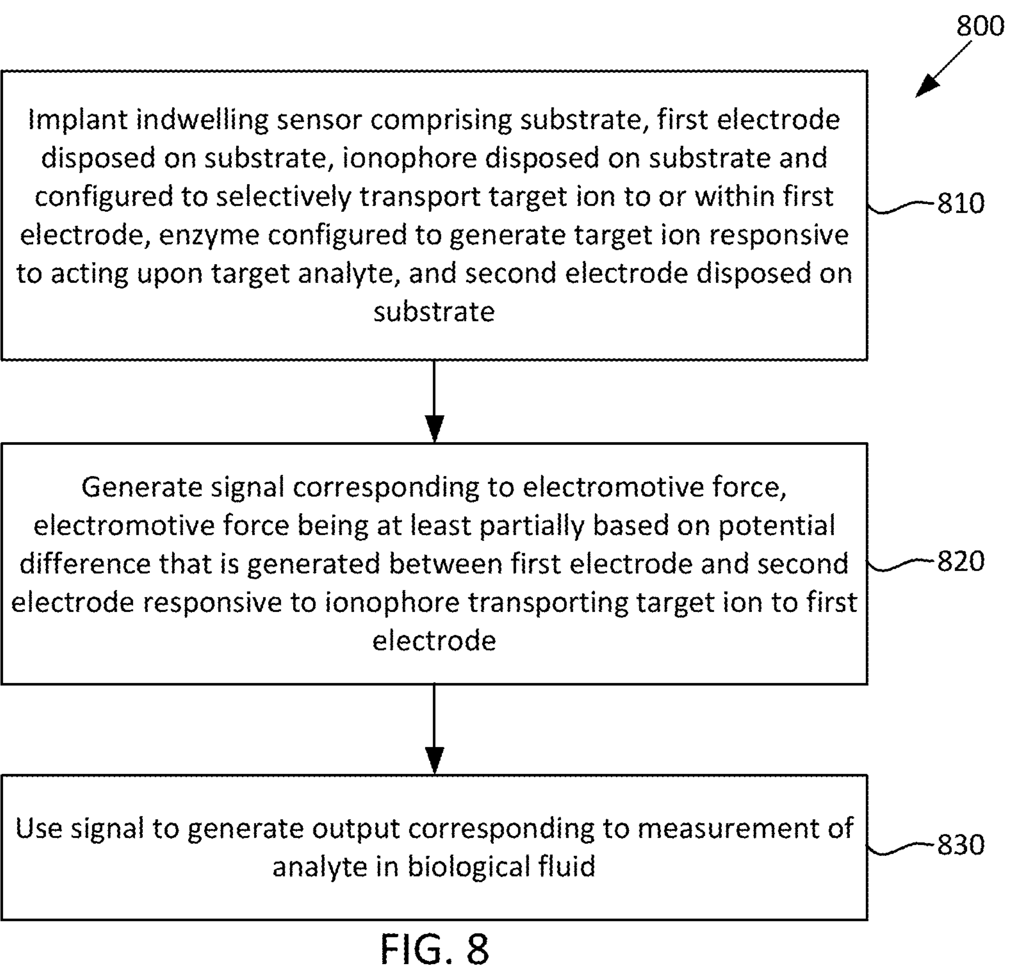
FIG. 8 illustrates a flow of operations in an example method for measuring a concentration of target analyte in a biological fluid in vivo.

FIG. 8 illustrates a flow of operations in an example method for measuring a concentration of target analyte in a biological fluid in vivo. Method 800 illustrated in FIG. 8 includes implanting an indwelling sensor (operation 810). In a manner such as described with reference to FIGS. 7A-7C, the sensor may include a substrate; a first electrode disposed on the substrate; an ionophore disposed on the substrate and configured to selectively transport a target ion to or within the first electrode; an enzyme configured to generate the target ion responsive to acting upon the target analyte; a second electrode disposed on the substrate. Method 800 also may include generating a signal corresponding to an electromotive force, the electromotive force being at least partially based on a potential difference that is generated between the first electrode and the second electrode responsive to the ionophore transporting the target ion to the first electrode (operation 820). Method 800 optionally also may include using the signal to generate an output corresponding to a measurement of the concentration of the analyte in the biological fluid (operation 830). For example, sensor electronics 120 may generate the output, or may transmit the signal to an external device which generates the output, in a manner similar to that described with reference to FIGS. 1A-11, 2A-2G, 3, 5A-5B, and 6A-6G.

Figure 17:
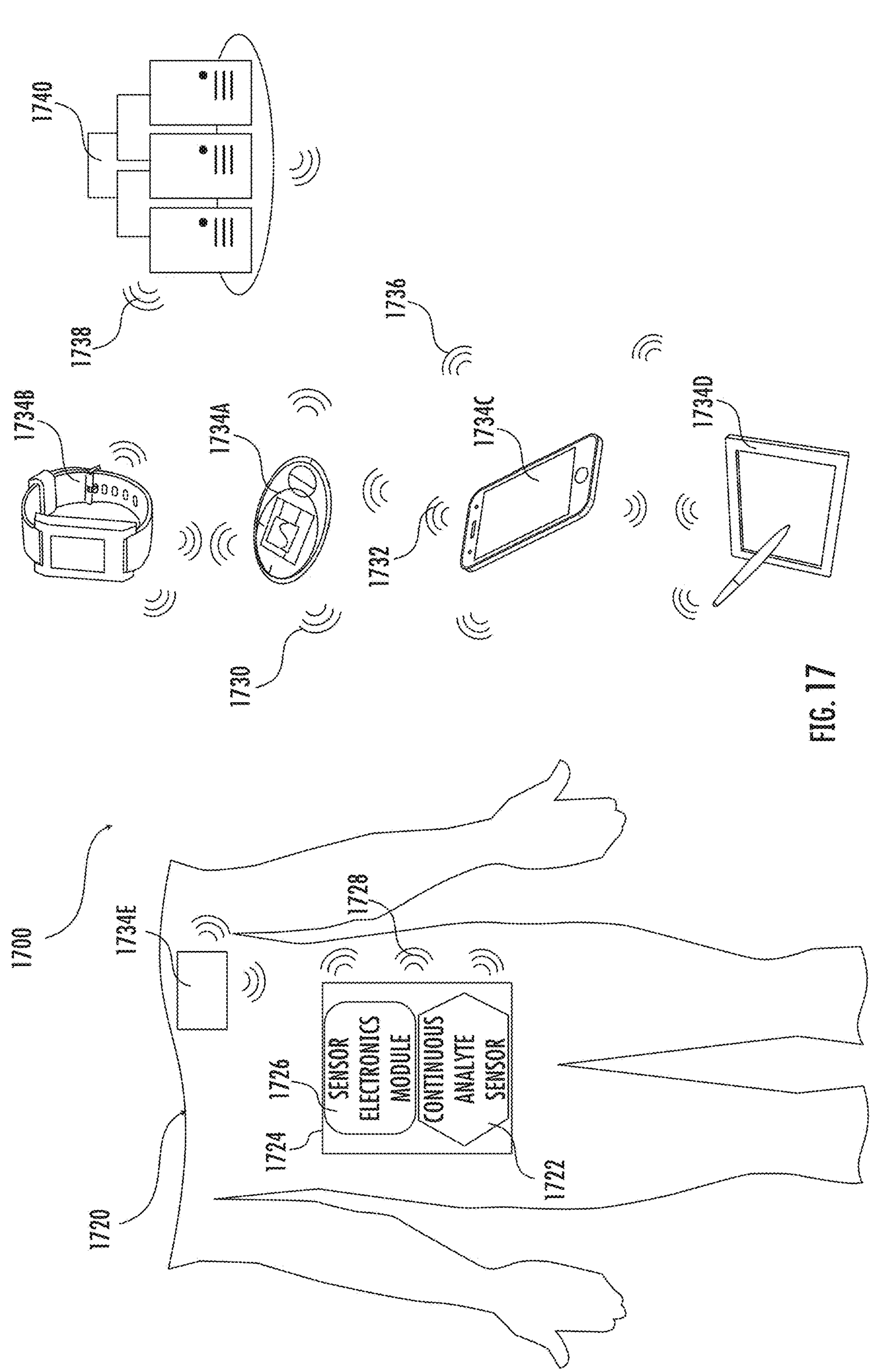
FIG. 17 is a diagram depicting an example continuous analyte monitoring system configured to measure target ions and/or other analytes as discussed herein.

FIG. 17 is a diagram depicting an example continuous analyte monitoring system 1700 configured to measure one or more target ions and/or other analytes as discussed herein. The monitoring system 1700 includes an analyte sensor system 1724 operatively connected to a host 1720 and a plurality of display devices 1734 *a-e* according to certain aspects of the present disclosure. It should be noted that the display device 1734*e* alternatively or in addition to being a display device, is a medicament delivery device that can act cooperatively with the analyte sensor system 1724 to deliver medicaments to host 1720. In one example, the analyte sensor system 1724 may include a sensor electronics module 1726 and a continuous analyte sensor 1722 associated with the sensor electronics module 1726. In one example, the sensor electronics module 1726 is in direct wireless communication with one or more of the plurality of the display devices 1734*a-e* via wireless communications signals.

As will be discussed in greater detail below, display devices 1734*a-e* may also communicate amongst each other and/or through each other to analyte sensor system 1724. For ease of reference, wireless communications signals from analyte sensor system 1724 to display devices 1734*a-e* can be referred to as "uplink" signals 1728. Wireless communications signals from, e.g., display devices 1734*a-e* to analyte sensor system 1724 can be referred to as "downlink" signals 1730. Wireless communication signals between two or more of display devices 1734*a-e* is referred to as "cross-link" signals 1732. Additionally, wireless communication signals can include data transmitted by one or more of display devices 1734*a-d* via "long-range" uplink signals 1736 (e.g., cellular signals) to one or more remote servers 1740 or network entities, such as cloud-based servers or databases, and receive long-range downlink signals 1738 transmitted by remote servers 1740.

The sensor electronics module 1726 includes sensor electronics that are configured to process sensor information and generate transformed sensor information. In certain embodiments, the sensor electronics module 1726 includes electronic circuitry associated with measuring and processing data from continuous analyte sensor 1722, including prospective algorithms associated with processing and calibration of the continuous analyte sensor data. The sensor electronics module 1726 can be integral with (non-releasably attached to) or releasably attachable to the continuous analyte sensor 1722 achieving a physical connection therebetween. In one example, the sensor electronics module 1726 may include hardware, firmware, and/or software that enables analyte level measurement. For example, the sensor electronics module 1726 can include a potentiostat, a power source for providing power to continuous analyte sensor 1722, other components useful for signal processing and data storage, and a telemetry module for transmitting data from itself to one or more display devices 1734*a-e*. Electronics can be affixed to a printed circuit board (PCB), or the like, and can take a variety of forms. For example, the electronics can take the form of an integrated circuit (IC), such as an Application-Specific Integrated Circuit (ASIC), a microcontroller, and/or a processor. Examples of systems and methods for processing sensor analyte data are described in more detail herein and in U.S. Pat. Nos. 7,310,544 and 6,931,327 and U.S. Patent Publication Nos. 2005/0043598, 2007/0032706, 2007/0016381, 2008/0033254, 2005/0203360, 2005/0154271, 2005/0192557, 2006/0222566, 2007/0203966 and 2007/0208245, each of which are incorporated herein by reference in their entirety for all purposes.

Display devices 1734*a-e* are configured for displaying, alarming, and/or basing medicament delivery on the sensor information that has been transmitted by the sensor electronics module 1726 (e.g., in a customized data package that is transmitted to one or more of display devices 1734*a-e* based on their respective preferences). Each of the display devices 1734*a-e* can include a display such as a touchscreen display for displaying sensor information to a user (most often host 1720 or a caretaker/medical professional) and/or receiving inputs from the user. In some embodiments, the display devices 1734*a-e* may include other types of user interfaces such as a voice user interface instead of or in addition to a touchscreen display for communicating sensor information to the user of the display device 1734*a-e* and/or receiving user inputs. In some embodiments, one, some or all of the display devices 1734*a-e* are configured to display or otherwise communicate the sensor information as it is communicated from the sensor electronics module 1726 (e.g., in a data package that is transmitted to respective display devices 1734*a-e*), without any additional prospective processing required for calibration and real-time display of the sensor information.

In the embodiment of FIG. 17, one of the plurality of display devices 1734*a-e* is a custom display device 1734*a* specially designed for displaying certain types of displayable sensor information associated with analyte values received from the sensor electronics module 1726 (e.g., a numerical value and an arrow, in some embodiments). In some embodiments, one of the plurality of display devices 1734*a-e* is a handheld device 1734*c*, such as a mobile phone based on the Android, iOS operating system or other operating system, a palm-top computer and the like, where handheld device 1734*c* may have a relatively larger display and be configured to display a graphical representation of the continuous sensor data (e.g., including current and historic data). Other display devices can include other handheld devices, such as a tablet 1734*d*, a smart watch 1734*b*, a medicament delivery device 1734*e*, a blood glucose meter, and/or a desktop or laptop computer.

As discussed above, because the different display devices 1734*a-e* provide different user interfaces, content of the data packages (e.g., amount, format, and/or type of data to be displayed, alarms, and the like) can be customized (e.g., programmed differently by the manufacture and/or by an end user) for each particular display device and/or display device type. Accordingly, in the embodiment of FIG. 1, one or more of display devices 1734*a-e* can be in direct or indirect wireless communication with the sensor electronics module 1726 to enable a plurality of different types and/or levels of display and/or functionality associated with the sensor information, which is described in more detail elsewhere herein.

Continuous Analyte Sensor

Generally, continuous analyte sensor 1722 is an implantable analyte sensor that utilizes at least potentiometric sensing technology to measure one or more analyte concentrations. Electrodes comprising continuous analyte sensor 1722 may include a working electrode, a counter electrode, and/or a reference electrode. In one embodiment, the counter electrode is provided to balance the current generated by the species being measured at the working electrode.

In some alternative embodiments, additional electrodes can be included within the assembly, for example, a three-electrode system (working, reference, and counter electrodes) and an additional working electrode (e.g., an electrode which can be used to generate oxygen, which is configured as a baseline subtracting electrode, or which is configured for measuring additional analytes). U.S. Pat. No. 7,081,195, U.S. Patent Publication No. 2005/0143635, and U.S. Patent Publication No. 2007/0027385, each of which are incorporated herein by reference in its entirety, describe some systems and methods for implementing and using additional working, counter, and reference electrodes.

Working Examples

Figures 9A, 9B:
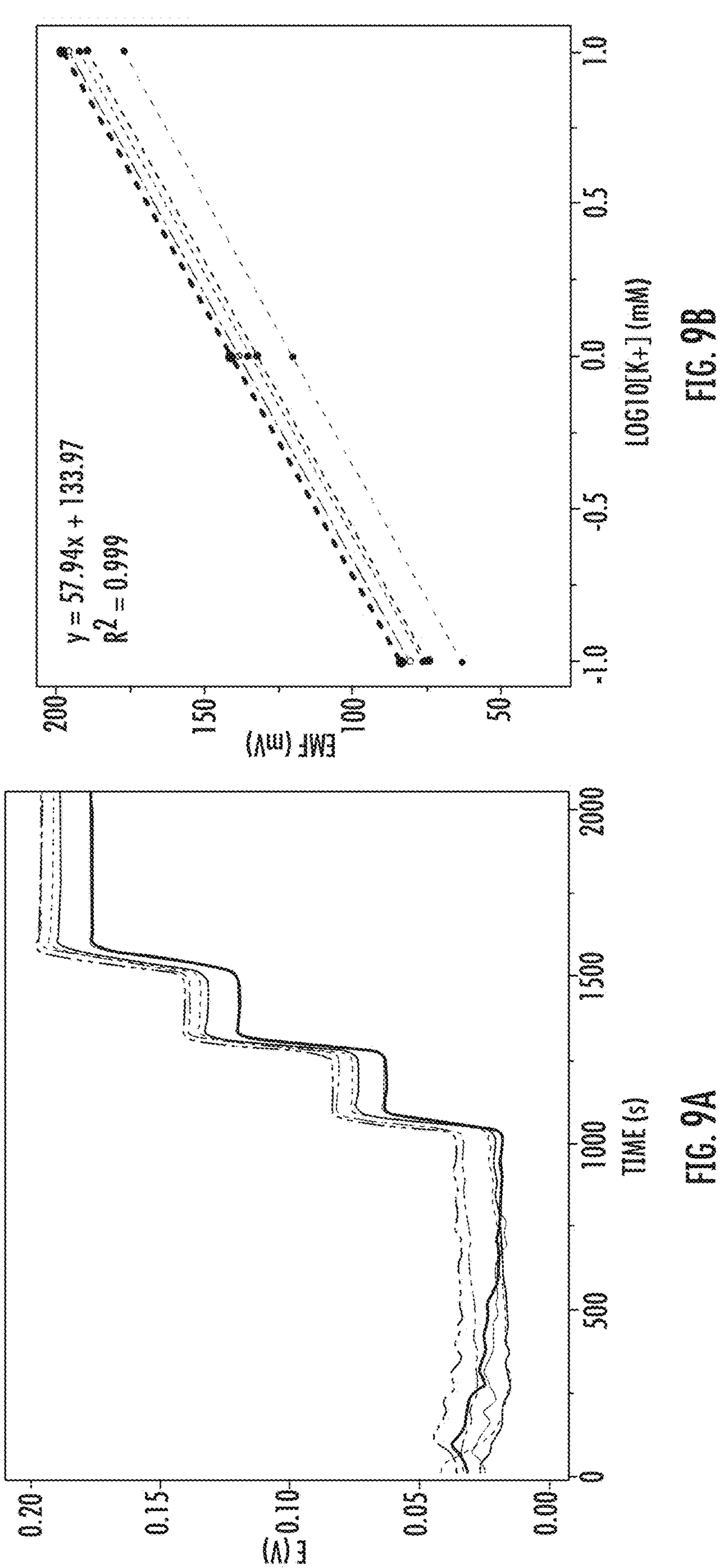
FIGS. 9A-9B are plots illustrating the measured sensitivity of an example device towards potassium ions.
Figures 10A, 10B:
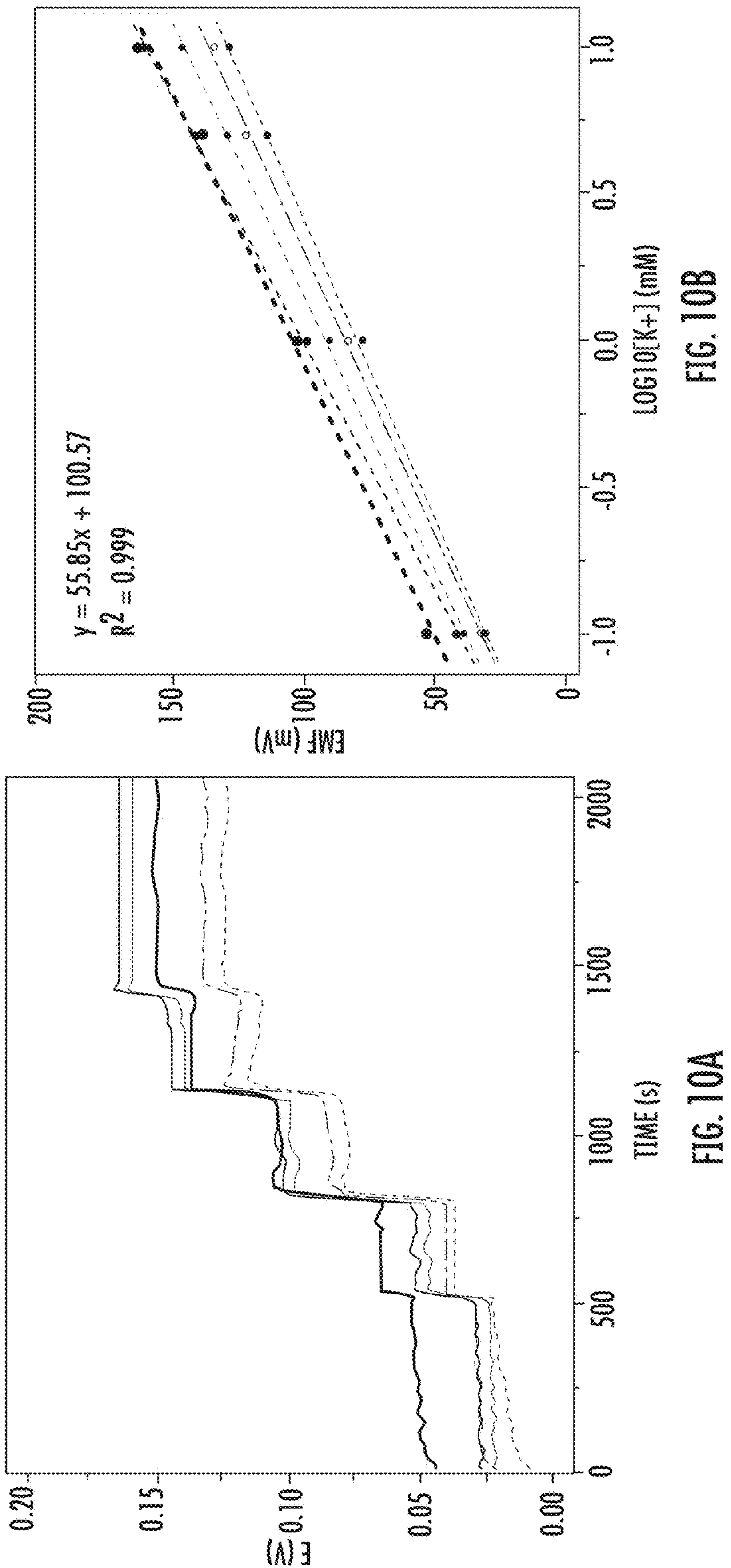
FIGS. 10A-10B are plots illustrating the measured sensitivity of the example device described with reference to FIGS. 9A-9B towards potassium ions in the presence of interfering ions.
Figure 11:
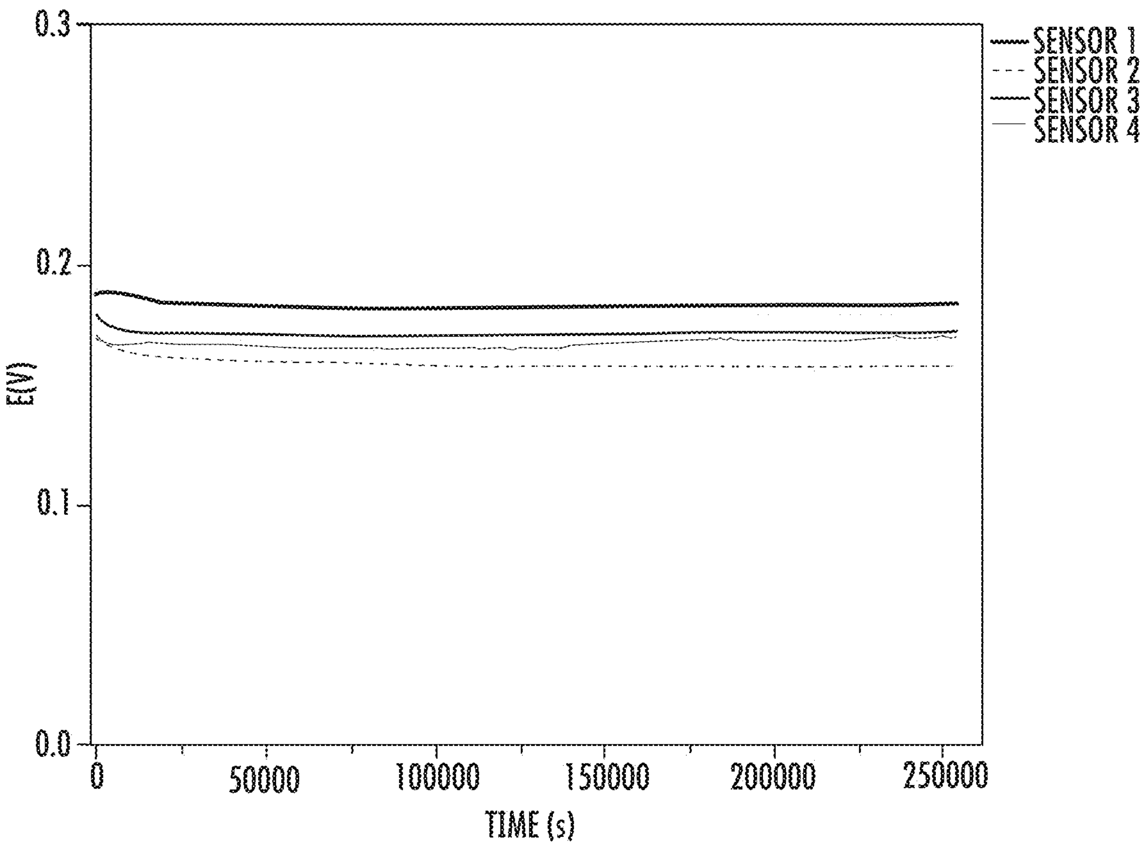
FIG. 11 is a plot illustrating the drift of the example device described with reference to FIGS. 9A-9B and 10A-10B.

The following examples are intended to be purely illustrative, and not limiting of the present disclosure. FIGS. 9A-9B are plots illustrating the measured sensitivity of an example device towards potassium ions. More specifically, an example sensor was prepared on a coaxial gold wire modified with a PEDOT(PSS) layer functioning as a solid contact (SC) and subsequent fluorosilicone ISM containing potassium ionophore 2 and KTClPB (1.0 wt. % and 0.3 wt. %, respectively) as sensing components. The sensor displayed close-to Nernstian (~58 mV per decade of concentration, n=6) response in an aqueous sample containing different concentrations of potassium ions, as demonstrated in FIGS. 9A-9B. FIGS. 10A-10B are plots illustrating the measured sensitivity of substantially identical composition devices towards potassium ions in the presence of interfering ions. More specifically, the selectivity of the potassium ion sensor was evaluated by measuring changes in potassium activities in a sample containing different interfering ions (140 mM NaCl, 1.2 mM $CaCl_2$, 1 mM $MgCl_2$) (FIGS. 10A-10B), demonstrating again close-to Nernstian sensitivity (~56 mV per decade of concentration, n=5) and validating the potential use of such sensor in real samples. FIG. 11 is a plot illustrating the drift of the example device described with reference to FIGS. 9A-9B and 10A-10B. More specifically, to demonstrate the potential use of the present ion sensor for the continuous monitoring of ions, the potassium ion sensor was immersed in a 10 mM KCl solution and left drifting over 70 h (FIG. 11). The drift in the potentiometric response calculated from 4 identical sensors that were immersed in a 10 mM KCl solution for 72 h was 2±1 mV.

Figure 12:
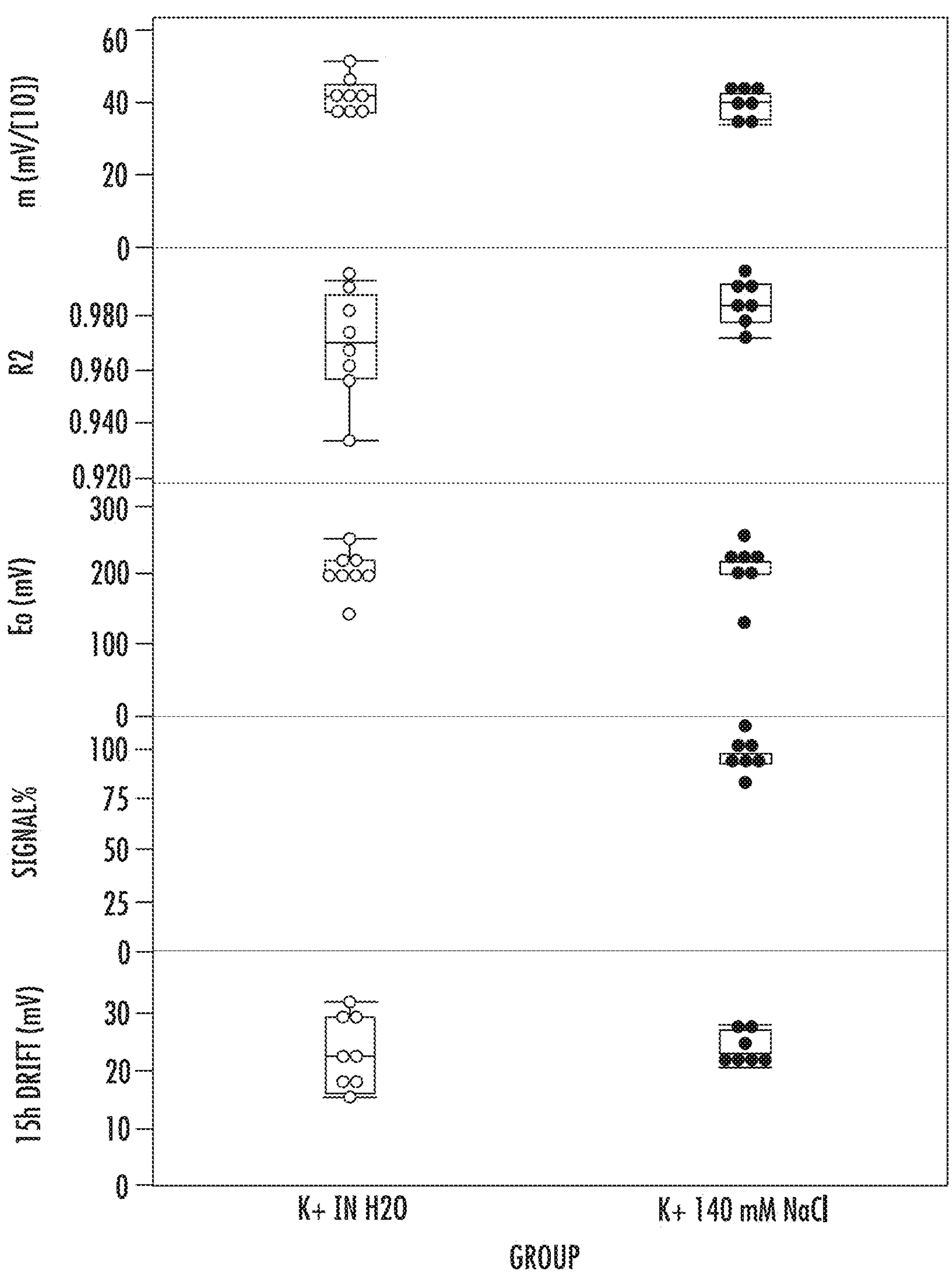
FIG. 12 illustrates plots of the measured absolute potential ($E_0$), potential slope (m), and drift of another example device in water (left) and interferent solution (right).

FIG. 12 illustrates plots of the measured absolute potential ($E_0$), potential slope (m), and drift of another example device both in water and in a 140 mM NaCl solution (green and orange, respectively; n=8). More specifically, the sensor of the device included a coaxial carbon-coated gold wire modified by dip coating techniques with a P30T-doped fluorosilicone ISM (1 wt. % potassium ionophore 2; 0.3 wt. % KTClPB; 5 mg/mL P30T). The sensors exhibited the absolute potential ($E_0$), potential slope (m), and drift characteristics illustrated in FIG. 12. Sensors demonstrated similar performance in absence of presence of the model interferent ion (sodium), showing minimum drop in sensitivity when measuring potassium in presence of sodium.

Figures 13A, 13B:
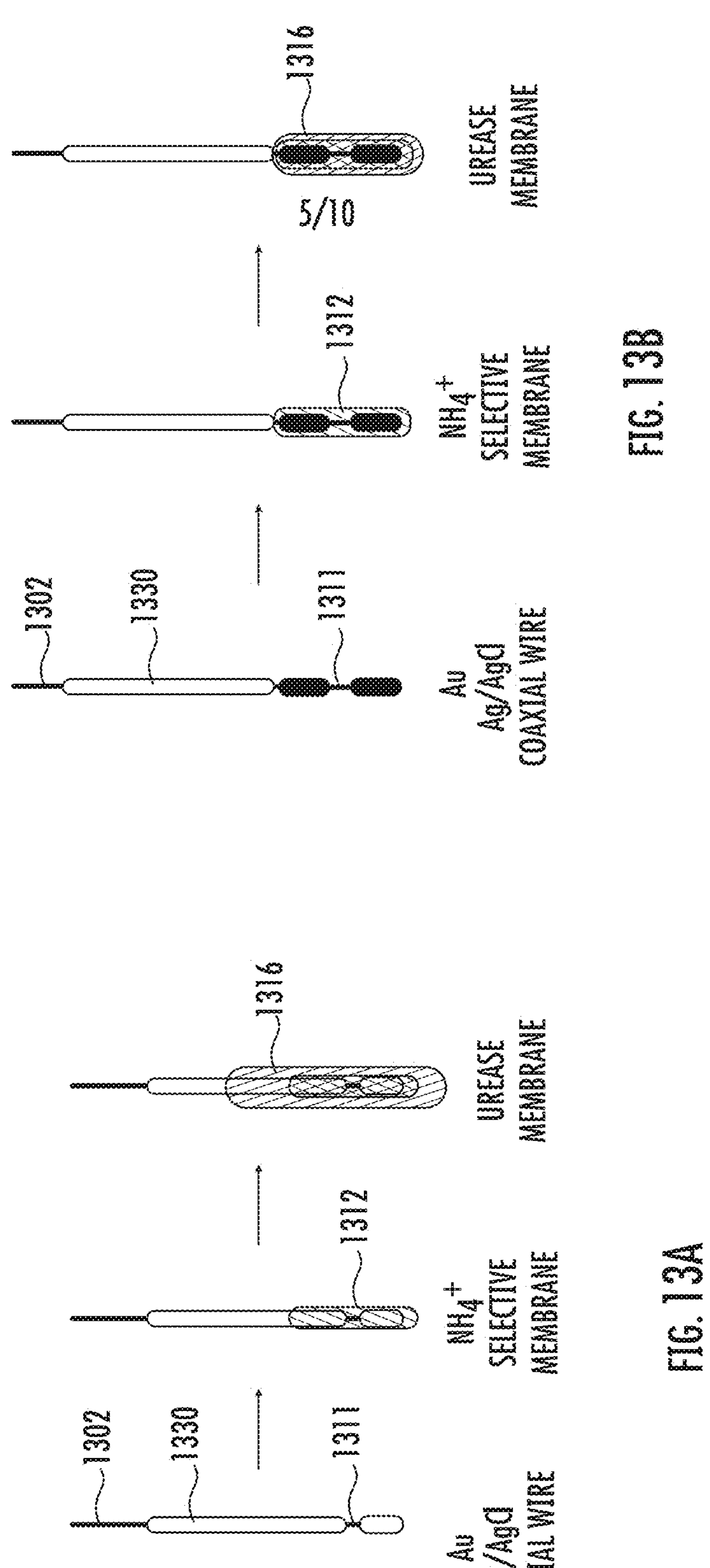
FIGS. 13A-13B schematically illustrate example devices configured to detect urea using a urease enzyme and an ionophore which is selective for ammonium ions.

It will be appreciated that potassium ions are a nonlimiting example of ions that is detected using the present devices and methods. For example, FIGS. 13A-13B schematically illustrate example devices configured to detect urea using a urease enzyme and an ionophore which is selective for ammonium ions. As illustrated in FIGS. 13A-13B, a gold wire (core or substrate) 1301 is partially coated with Ag/AgCl 1330 (reference electrode) leaving a window within which the gold is exposed to form a first electrode (working electrode) 1311 in a manner such as described with reference to FIGS. 6A-6G. The working electrode 1311 is formed by removing a portion of one or more overlying layers, for example, by etching processes including but not limited to laser ablation/skiving/etching, grit-blasting, or other method or combinations of methods. In some examples, an insulating material as discussed herein is positioned in between the working electrode 1311 and the reference electrode 1330. In other examples, no insulating material is positioned between the working electrode 1311 and the reference electrode 1330. An ammonium-selective membrane 1312, e.g., ion-selective membrane 212 described with reference to 2A and including the ammonium-selective ionophore nonactin, is deposited over the first electrode 1311. In one example, the reference electrode is devoid of any ion-selective membrane and ionophore. A urease membrane 1316, e.g., enzyme layer 716 described with reference to FIGS. 7A-7C and including urease as the enzyme 715, is deposited over the ammonium-selective membrane.

Figures 14A, 14B:
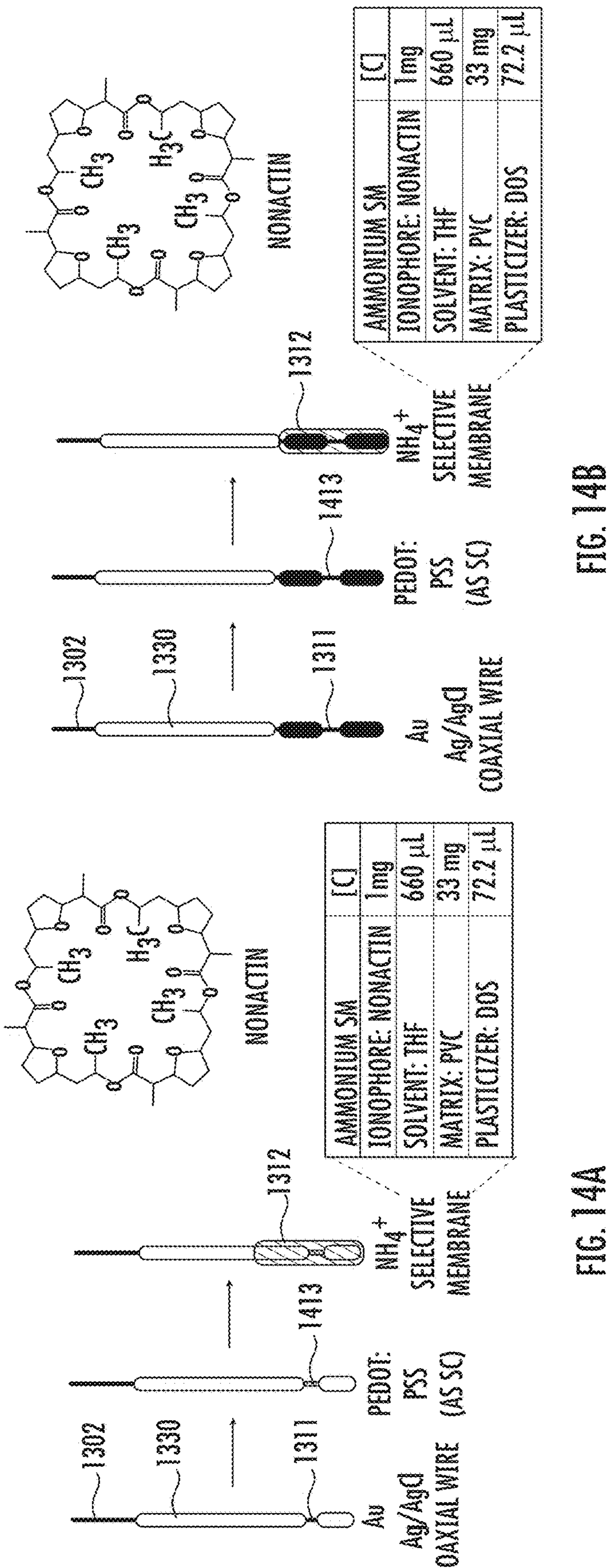
FIGS. 14A-14B schematically illustrate example devices using an ionophore which is selective for ammonium ions.

FIGS. 14A-14B schematically illustrate example devices using an ionophore which is selective for ammonium ions.

More specifically, for purposes of characterizing the ammonium-selective membrane 1312 described with reference to FIGS. 13A-13B, a device was prepared. As illustrated in FIGS. 14A-14B and similarly as described with reference to FIGS. 13A-13B, a gold wire (core or substrate) 1301 was partially coated with Ag/AgCl 1330 leaving a window within which the gold is exposed to form a first electrode (working electrode) 1311 in a manner such as described with reference to FIGS. 6A-6G. A solid-contact layer (SC) including PEDOT:PSS was deposited over the first electrode 1311. An ammonium-selective membrane 1312, e.g., ion-selective membrane 212 described with reference to 2A and including the ammonium-selective ionophore nonactin, was deposited over the SC layer 1413. In one example, the reference electrode is devoid of any ion-selective membrane and ionophore. The ammonium-selective membrane 1312 was prepared by repeatedly dipping the distal tip of the device into a solution including about 1 mg of nonactin dissolved in about 660 microliters (μL) of tetrahydrofuran (THF), 33 mg of PVC, and 72.2 μL of the plasticizer dioctyl sebacate (DOS), allowing the tip to dry between dips into the solution.

Figure 15:
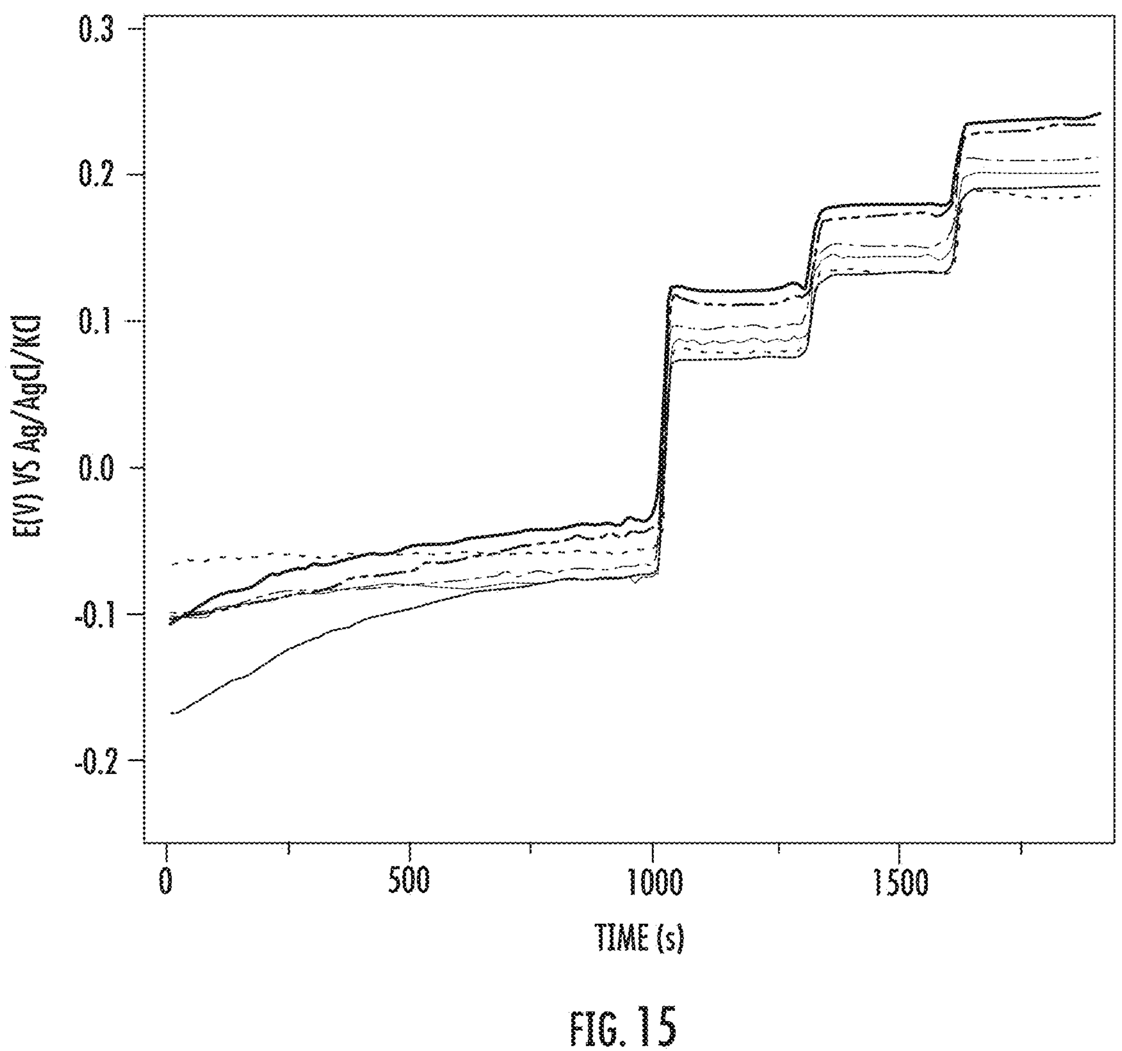
FIG. 15 is a plot illustrating the measured sensitivity of the example device of FIGS. 14A-14B towards ammonium ions.
Figure 16:
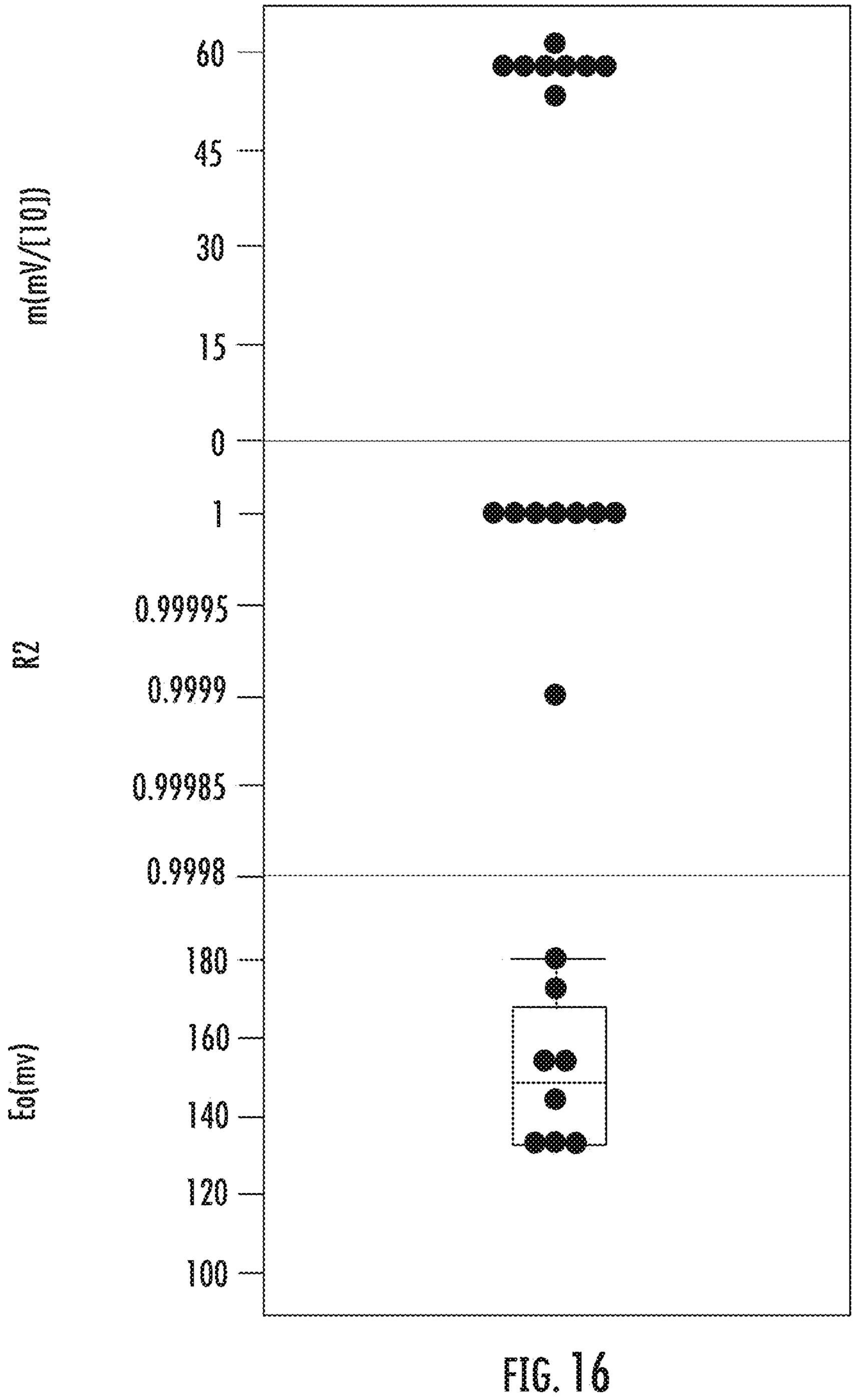
FIG. 16 illustrates plots of the measured absolute potential ($E_0$), potential slope (m), and R2 of the example device of FIGS. 14A-14B and 15 towards ammonium ions.

The response of the device of FIGS. 14A-14B to aqueous ammonium ions was characterized as a way of approximately simulating the response of the device of FIGS. 13A-13B to urea, e.g., as a way of approximately simulating urease's generation of ammonium ions responsive to action upon urea. FIG. 15 is a plot illustrating the measured sensitivity of the example device of FIGS. 14A-14B towards ammonium ions. More specifically, the device first was conditioned for about 2 h in about 0.1 M ammonium chloride, and then was dipped into aqueous ammonium chloride solutions having concentrations of about 0.1 mM, 1 mM, and 10 mM, respectively. The sensor displayed close-to Nernstian sensitivity (~57 mV per decade of concentration, n=8) in an aqueous sample containing different concentrations of ammonium ions, as demonstrated in FIG. 15. FIG. 16 illustrates plots of the measured absolute potential ($E_0$), potential slope (m), and R-squared (R2) of the example device of FIGS. 14A-14B and 15 towards ammonium ions. The R2 value is the coefficient of determination that indicates a strength in the relationship between the linear model and the dependent variable, for example, the potential response with respect to ion concentration, values close to 1.000 is desirable. The determination of ammonium yielded a linear response range of 0.1 to 10 mM with R2 values ≥0.999. The analytical characteristics summarized in FIG. 16 demonstrate the performance of the ammonium selective electrode towards the detection of ammonium ions in aqueous samples.

Selectivity Coefficient Calculation

Figures 18A, 18B:
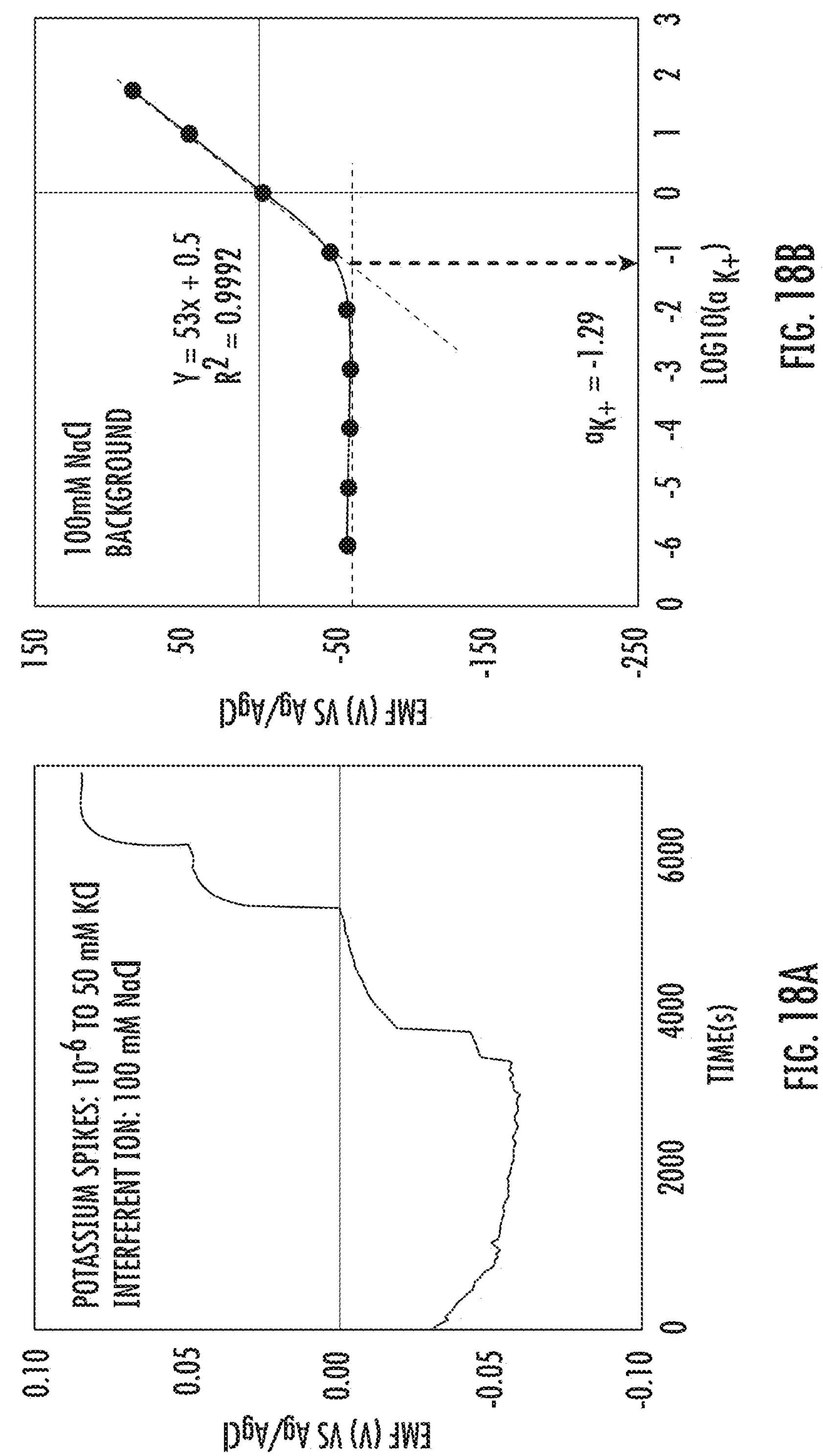
FIGS. 18A and 18B illustrate plots of the measured sensitivity of an example device.

FIGS. 18A and 18B illustrate the selectivity of an example continuous potassium ion sensor as discussed herein. Selectivity of the ISEs can be expressed by its selectivity coefficient '$K_a$/b', a numerical measure of how well the ISM can discriminate the target ion (a) against the interfering ion (b). In some examples as discussed herein, '$K_a$/b'<1 is desirable. The selectivity coefficient discussed herein was calculated for a sensor having a first (working) electrode formed from carbon-coated gold (Au), and a second electrode formed from silver/silver chloride. The ISM formed on the sensor overlying the first electrode includes 1 wt. % potassium ionophore 2; 0.3 wt. % KTClPB; 6 wt. % DEX4041; 5 mg/mL P30T (Poly(3-octylthiophene-2,5-diyl)); and tetrahydrofuran (THF).

Selectivity Coeff. of the sensor was calculated using the Fixed Interference Method. Thus, the response of the sensor to a primary ion (range: 10-6 to 50 mM KCl) was evaluated in a solution with a fixed background of an interfering ion (100 mM NaCl). The activity of potassium ($a_{K+}$) was calculated from the intersection of the extrapolated linear portions of the EMF response to the −log of the activity of the primary ion (see plots described below).

Calculate $K^{pot}_{K+/Na+}$:

$$K^{pot}_{A,B} = a_A \Big/ (a_B)^{z_A/z_B}$$

$a_A$, activity primary ion $a_B$, activity interfering ion

Z, charge numbers of primary and interfering ions (same signs).

FIG. 18A illustrates the EMF generated when the KCl is introduced to the solution containing the 100 mM NaCl. FIG. 18A shows the response of the sensor to the addition of KCl in the solution. FIG. 18B presents data that was calculated based on FIG. 18A and shows the EMF generated in response to the increasing concentration of KCl, the slope change indicated by the arrow in FIG. 18B indicates where the sensor is able to detect KCl over NaCl (selectivity of KCl over NaCl is about −1.29 (activity of potassium). As shown in FIG. 18B, the continuous potassium ion sensor demonstrated adequate selectivity to measure K+ in the range of 0.1-50 mM in presence of 100 mM Na+:

$$\text{Log } K^{POT}_{K+,Na+} = -1.29/2 = -0.64$$

$$K^{POT}_{K+,Na+} = 5.1E^{-2} \Big/ 100 = 5.1E^{-4}$$

0.1-50 mM range of sensor operation, m (slope)=53 mV/decade of concentration.

Figures 19A, 19B:
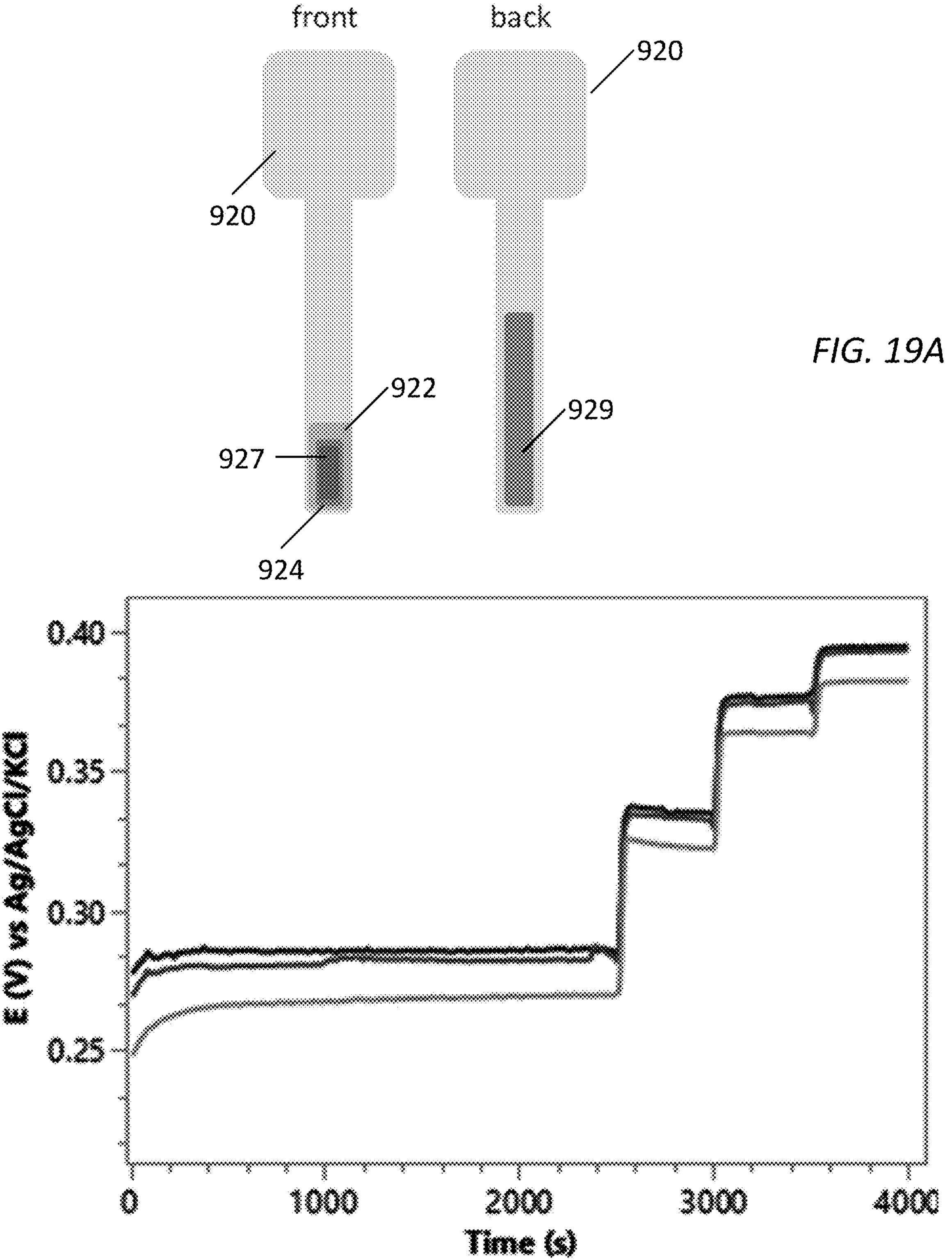
FIGS. 19A and 19B illustrate plots of the measured sensitivity of an example planar sensor device.

FIG. 19A depicts a planar configuration of an exemplary potassium ion sensor device 920 of the present disclosure consisting of a platinum WE 922 modified with a solid contact layer 924 and a sensing membrane 927 comprising 24 10 wt. %, polyurethane polymer with polysiloxane soft segment, 2.2 mg potassium ionophore III: bis[(benzo-15-crown-5)-4-methyl]pimelate (BB15C5), and 0.5 mg KTFPB, with a Ag/AgCl RE 929 situated on the opposite side of the planar substrate. Device 920 is configured to be inserted into a host's dermis or subcutaneous tissue to potentiometrically monitor the electrophysiological signal and/or the concentration of a selected ion in the host's interstitial fluid. A resistance membrane (not shown) can be employed over the WE and/or the RE. In one example, the resistance membrane is used to attenuate leaching of plasticizer from the ISM. In one example, the resistance membrane is used to attenuate leaching of plasticizer from a plasticized polyvinyl chloride (PVC) ISM. A biointerface membrane (not shown) can be employed with or without a releasable anti-inflammatory. In one example, the resistance membrane is used to attenuate leaching of silver and/or chloride from the second electrode (degradation) during use.

FIG. 19B depicts experimental data of $E_0$ verses potassium ion concentration obtained from three exemplary planar devices 920, demonstrating acceptable stability and sensitivity for continuous monitoring. Thus, FIG. 19B depicts sensitivity to potassium and $E_0$ displayed by the planar potassium ion sensor of FIG. 19A (n=3) vs Ag/AgCl/KCl (potassium break in solution: 0.1 mM KCl; potassium spikes were: 1, 5, 10 mM KCl, respectively). The data in FIG. 19B demonstrates repeatable sensitivity and resistance to drift of the sensor device 920 construct of FIG. 19A.

Interferent Testing Data

Figures 20A, 20B:
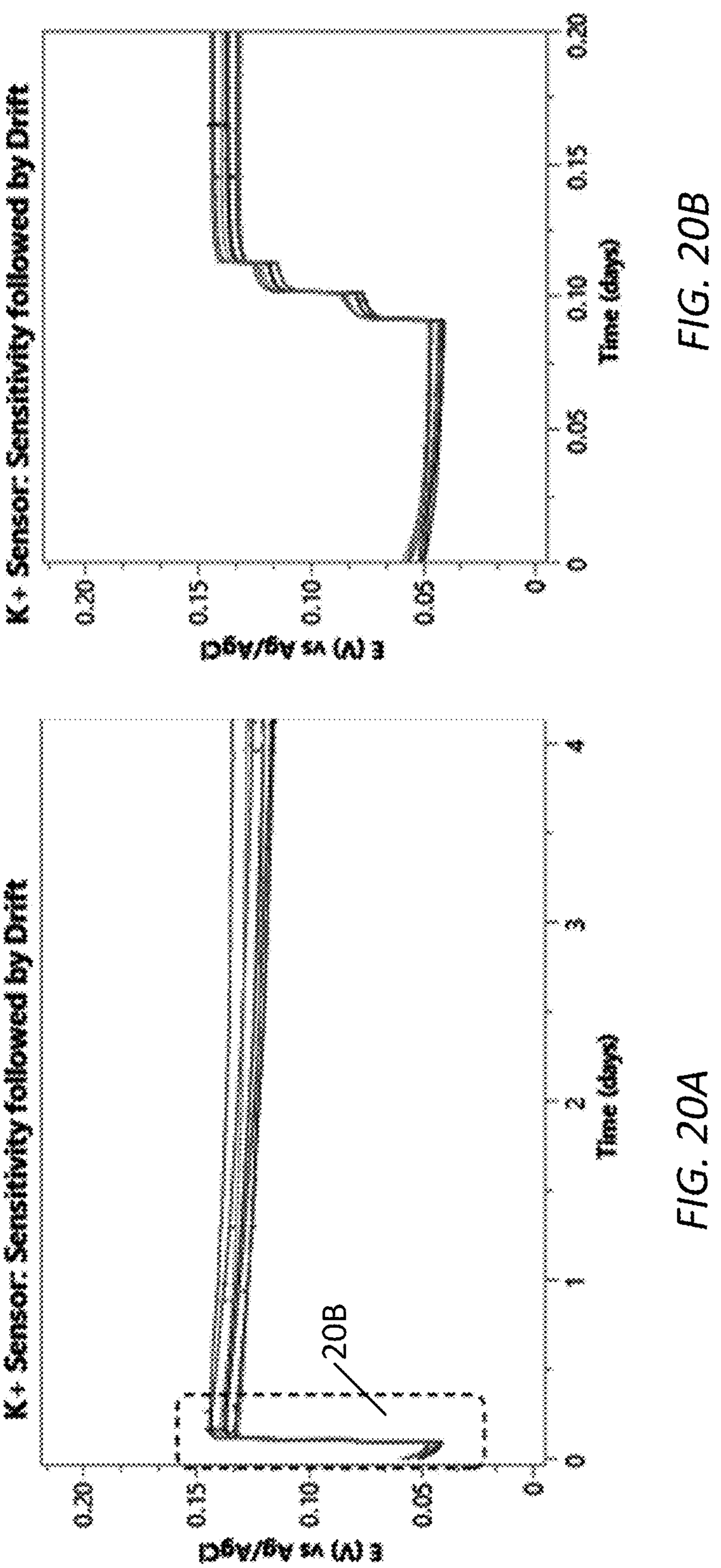
FIGS. 20A and 20B illustrate plots of the measured sensitivity of an example device in the presence of interfering ions.
Figures 20C, 20D:
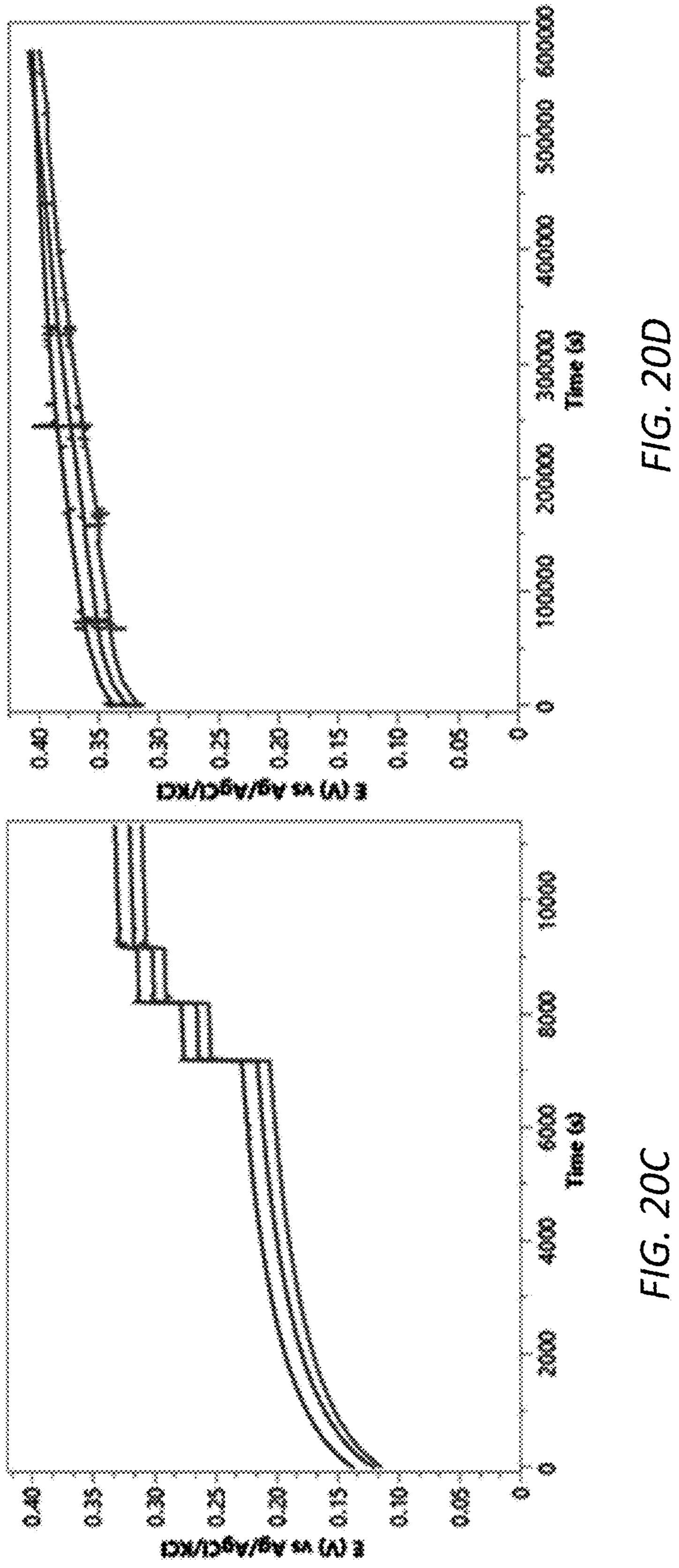
FIGS. 20C and 20D illustrate plots of the measured sensitivity of an example device in the presence of interfering ions.

In another example, an exemplary potassium ion sensor was developed comprising a gold wire/Carbon ink WE as first electrode, coated with ISM comprising 2-nitrophenyl octyl ether plasticized-PVC, BME44 ionophore, and KTFPB salt, with a Ag/AgCl RE as second electrode dip coated with a resistance membrane (polyvinyl pyrrolidone-CARBOSIL® blend using 25% Ethanol, 6% solids) and subjected to interferent (sodium chloride (NaCl)). FIG. 20A depicts data from seven identically prepared sensors and their sensitivity to potassium in presence of 140 mM NaCl interferent after 0.1 mM potassium ion spikes of: 1, 5, 10 mM KCl (FIG. 20B shows expanded section 20B of FIG. 20A), followed by 4 days drift in 10 mM KCl/140 mM NaCl (n=7) and corresponding measured sensitivity (m), absolute potential ($E_0$) as measured after 4 Days drift of the exemplary potassium ion sensor. This data demonstrates the stability and sensitivity of the sensor to pharmacologically relevant concentrations of potassium ion in the presence of pharmacologically relevant concentrations of interferent (e.g., sodium ion). Additional data was obtained using gold wire first electrode, a carbon ink solid contact layer and a fluorocarbon based ISM material FS730 Dupont) comprising BME44 ionophore, and KTFPB salt, with a Ag/AgCl RE as second electrode. FIG. 20C depicts data from three identically prepared sensors and their sensitivity to potassium in presence of 140 mM NaCl interferent after 0.1 mM potassium ion spikes of: 1, 5, 10 mM KCl and FIG. 20D depicts drift data of the sensors. This data demonstrates the stability and sensitivity of the sensor to pharmacologically relevant concentrations of potassium ion in the presence of pharmacologically relevant concentrations of interferent (e.g., sodium ion).

Solid Contact Layer Data

In some examples, GO material was compared with alternative carbon-based solid contact (SC) layer materials. Thus, gold wire electrodes were modified with different commercial carbon inks (Dupont 7102 and BQ221, hereinafter "7102" and "BQ221"), one of them supplemented with MWCNTs (10-20 μm). Sensors built with these conductive carbon inks as the SC showed response to potassium ion in the presence of interfering sodium ions. Samples were prepared using polyurethane polymer with polysiloxane soft segment as ISM with BME44 ionophore and compared to 2-nitrophenyl octyl ether plasticized PVC with the same ionophore sensors as control.

Figures 21A, 21B, 21C:
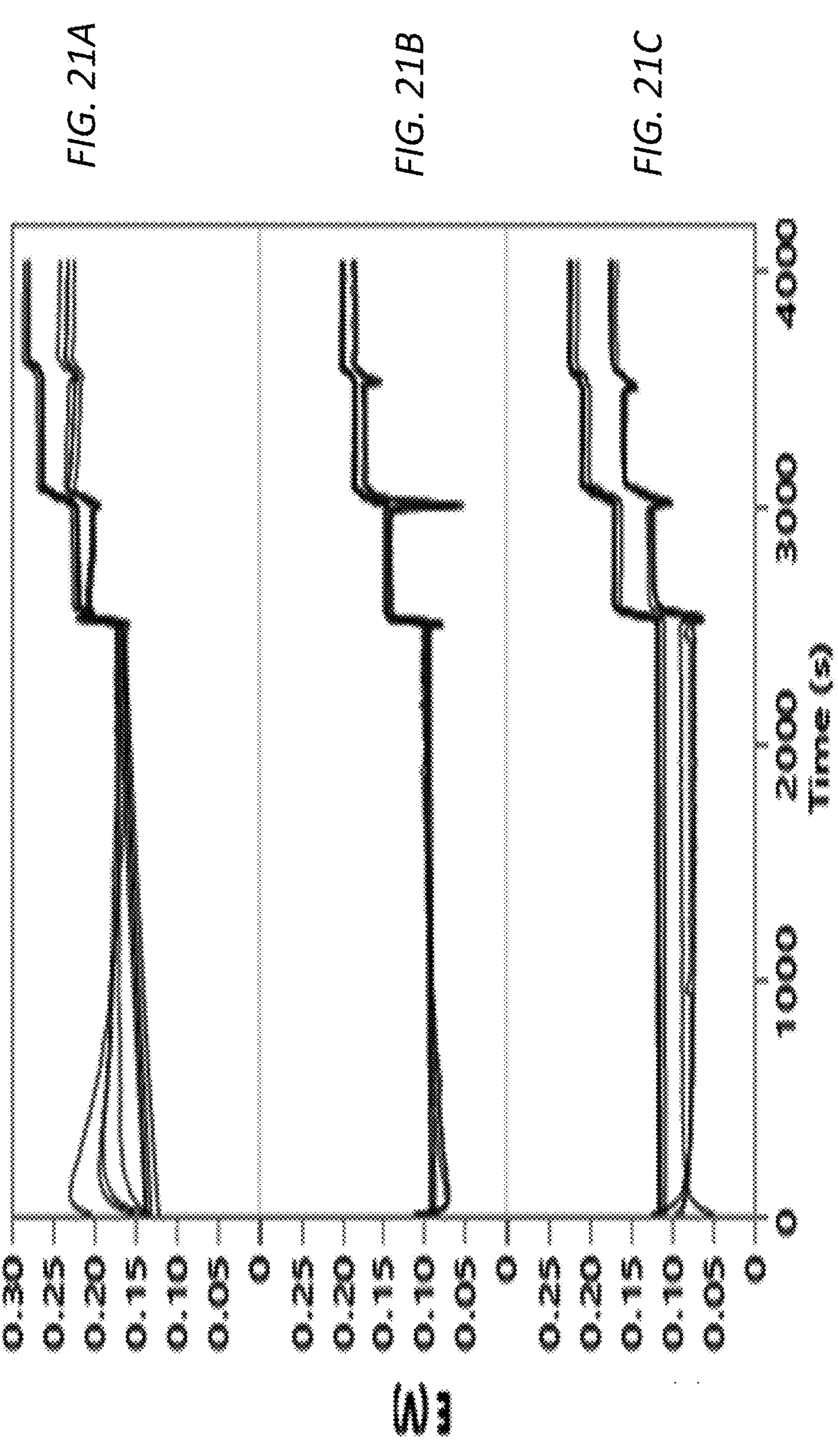
FIGS. 21A, 21B and 21C illustrate plots of the measured sensitivity of an example device with selected solid contact materials.

Thus, as depicted in FIGS. 21A, 21B, and 21C wire potassium ion sensor was developed comprising exemplary solid contact (SC) layers disposed between the first electrode and plasticized ISM 965 and polyurethane-polysiloxane-polycarbonate ion-selective membranes, where FIG. 21A represents identically prepared sensors with a SC comprising BQ221 in plasticized ISM and polyurethane-polysiloxane-polycarbonate ion-selective membranes, FIG. 21B represents identically prepared sensors with a SC comprising 7102 plasticized ISM 965 and polyurethane-polysiloxane-polycarbonate ion-selective membranes, and FIG. 21C represents identically prepared sensors with a SC comprising 7102 and carbon nanotubes plasticized ISM and polyurethane-polysiloxane-polycarbonate ion-selective membranes. This data demonstrates improvement in sensitivity and stability using SC comprising 7102. Carbon nanotube containing conductive inks did not show any significant improvement in m, $E_0$ or drift compared to other conductive inks tested.

Resistance Membrane Data

Figure 22A:
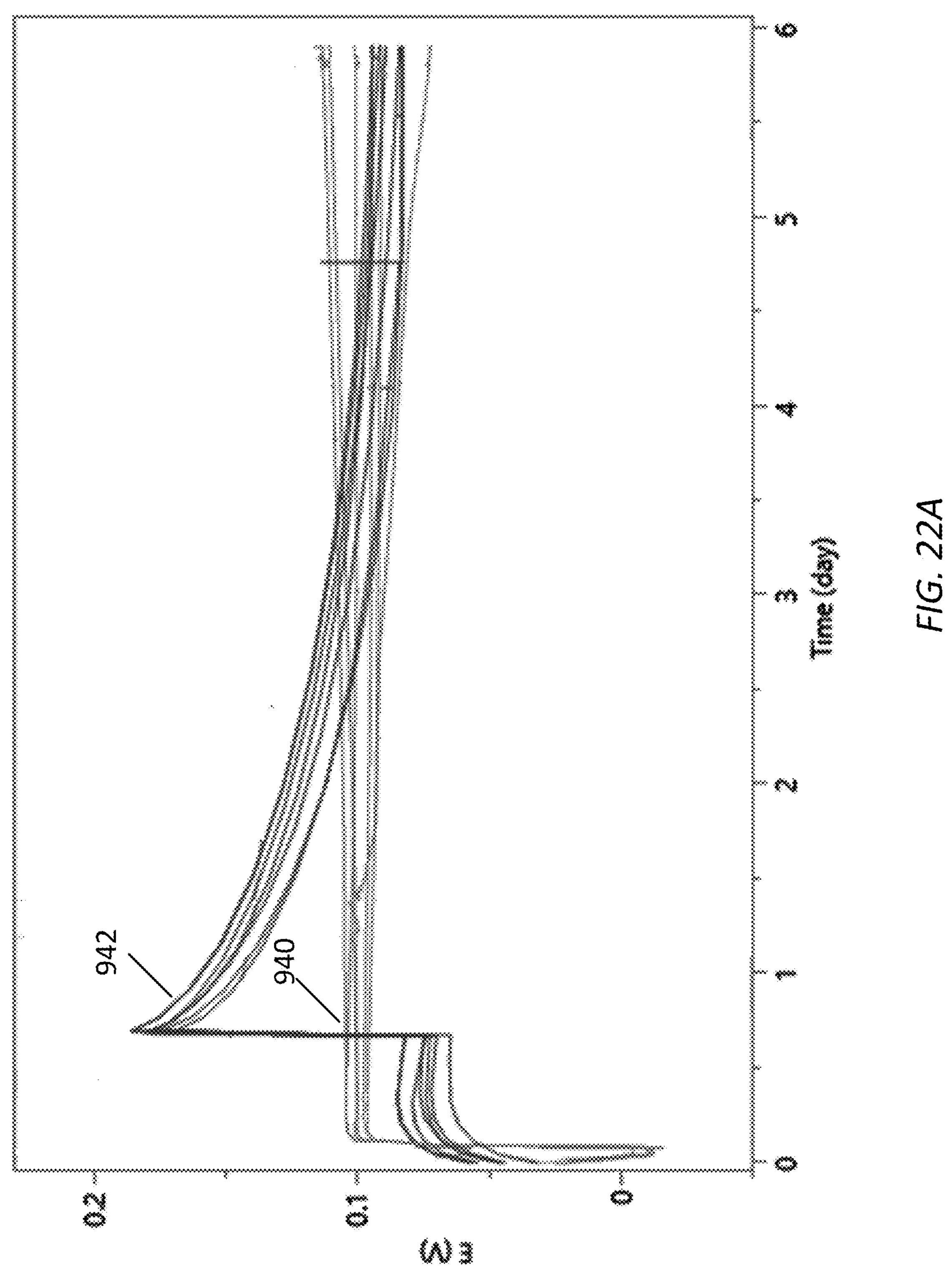
FIGS. 22A, 22B, and 22C illustrate data of measured sensitivity of an example device with resistance membrane.

FIG. 22A depicts the effect of sensitivity and stability of using a resistance membrane (RM) disposed on the first electrode and on the second electrode. Thus, in one example, a resistance membrane (RM) of (polyvinyl pyrrolidone-CARBOSIL® (a thermoplastic silicone polycarbonate polyurethane blend) was coated over a 2-nitrophenyl octyl ether plasticized-PVC ISM gold wire sensor 940 with solid contact carbon paste material 7102 and showed significantly improved drift compared to plasticized-PVC control sensor 942 without a RM. In one example, the resistance membrane is selected to minimize and/or attenuate plasticizer leaching from the ISM, thus enhancing continuous operation as well as reducing or eliminating degradation of the second electrode. In one example, the RM material is selected to minimize migration of low MW materials (e.g., plasticizers) to improve sensor life and minimize plasticizer leaching. In one example, biocompatible plasticizers for PVC are used, for example polyethylene glycol (PEG).

Figure 22B:
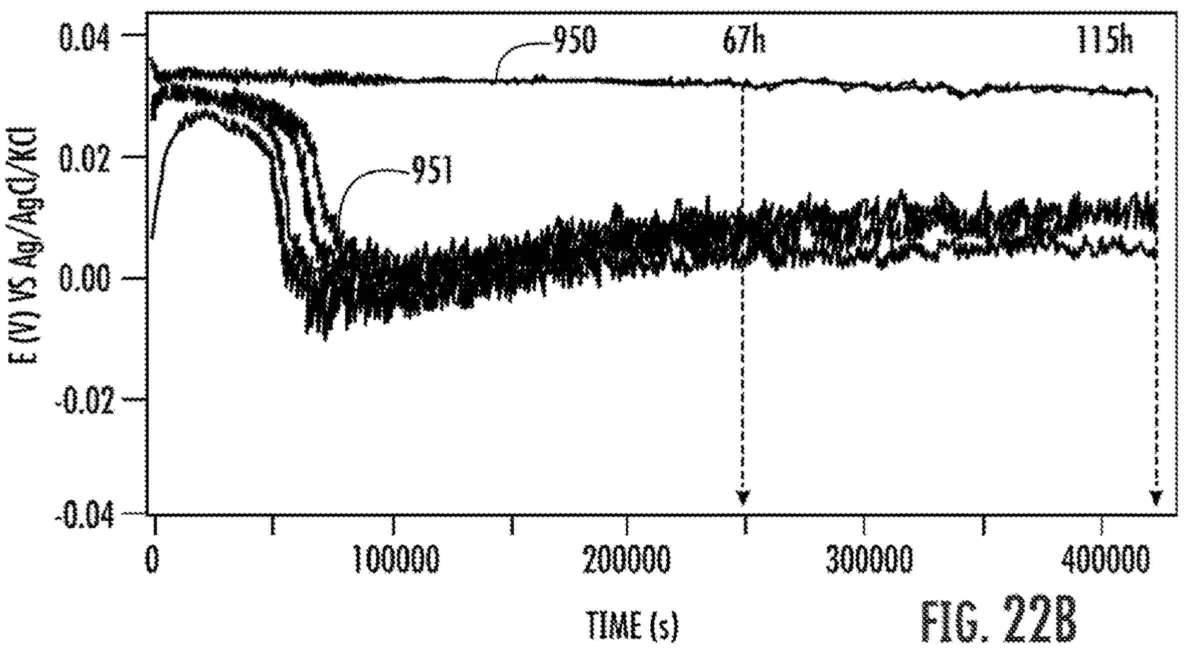
Figure 22C:
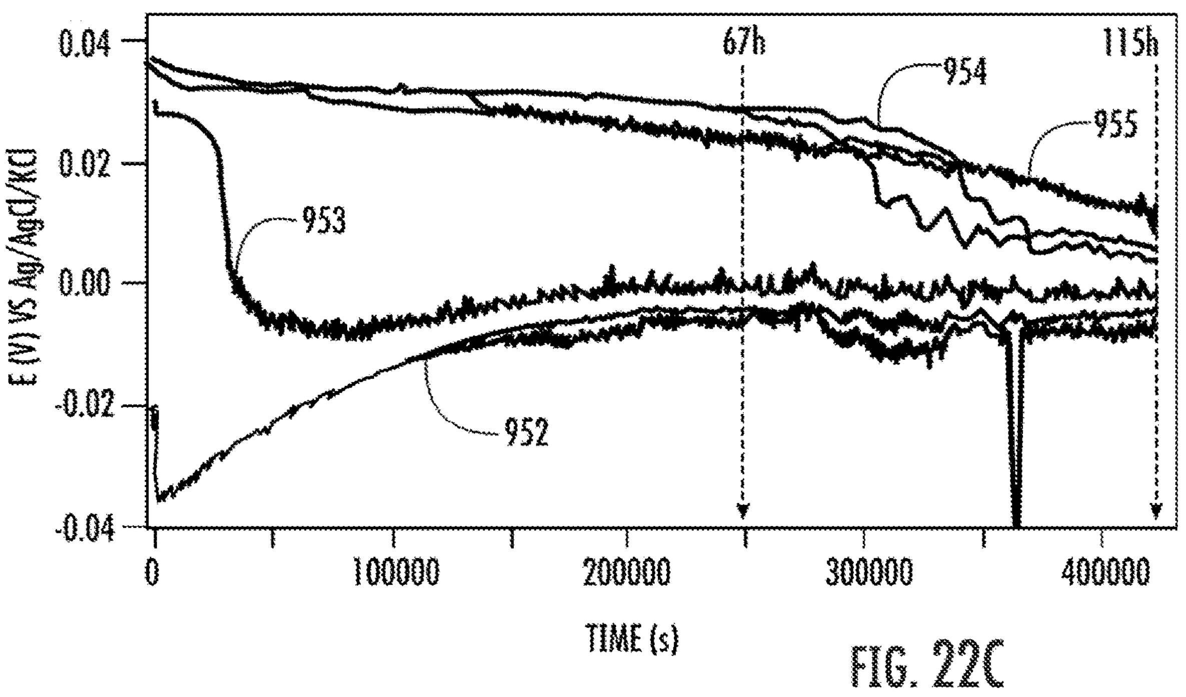

FIGS. 22B and 22C depict the effect of thickness and second electrode composition, respectively, on continuous ion sensor performance in the presence of physiological amounts of potassium and sodium ions. Thus, with constant second electrode composition (AgCl wt. %), second electrode thickness of at least 0.9 thousandths of an inch (23 microns) provided near constant drift data 950 compared with a reference electrode thickness of less than 0.6 thousandths of an inch (15 microns) drift data 951. FIG. 22C shows data for second electrodes of varying composition, where data 952 represents an AgCl wt. % of 0, data 953 represents an AgCl wt. % of 15, data 954 represents an AgCl wt. % of 40, data 955 represents an AgCl wt. % of 50. Thus, this data demonstrates improvement in sensor stability performance with higher amounts of AgCl in the second electrode in the presence of pharmacological amounts of potassium and sodium ions.

Figures 23A, 23B:
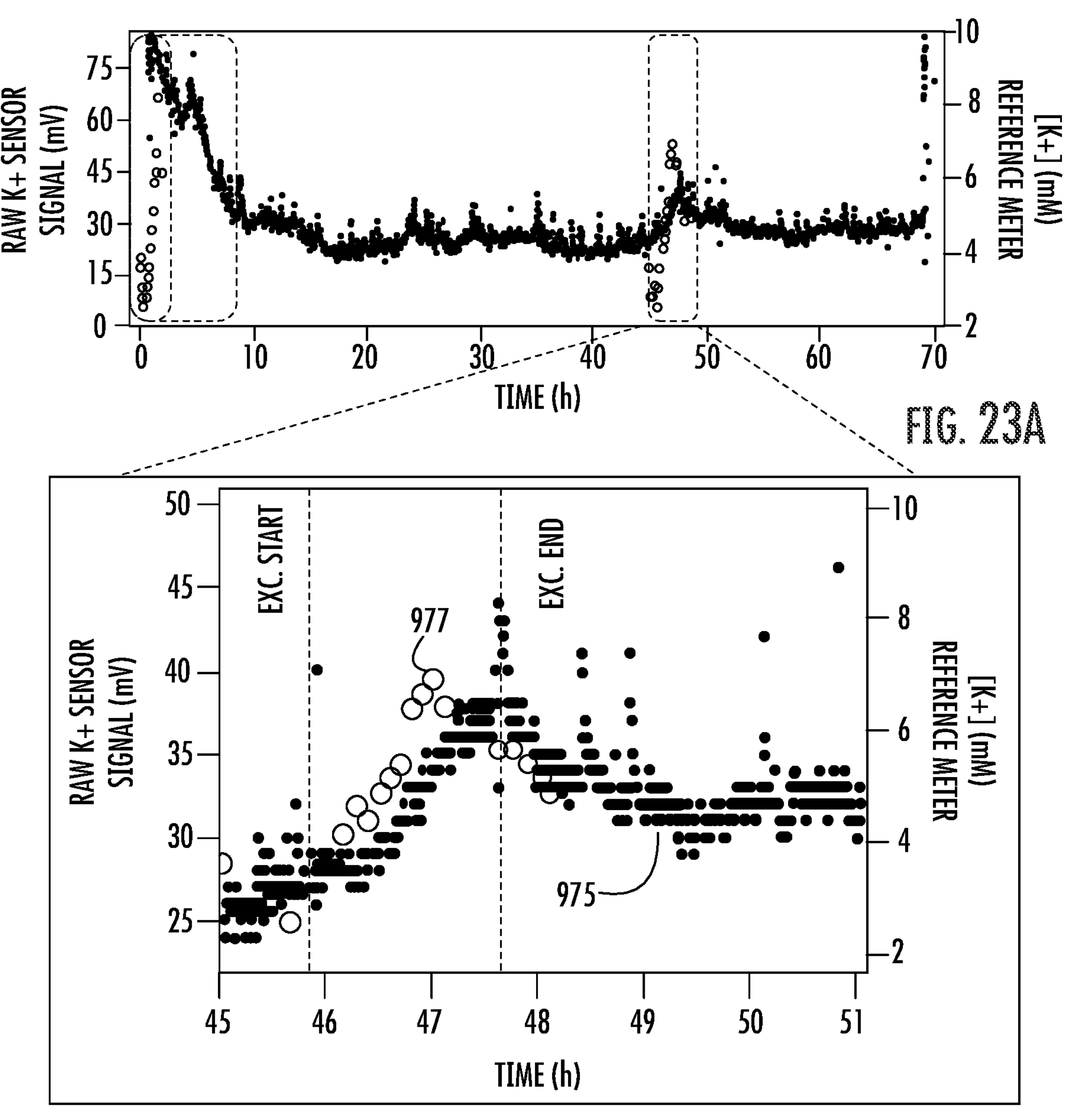
FIGS. 23A, 23B, and 23C illustrate plots of the measured sensitivity of exemplary devices in vivo.

FIGS. 23A and 23B depict in vivo animal data of an exemplary coaxial potassium ion sensor representative of the present disclosure utilizing a gold wire first electrode with graphene oxide solid contact layer coated with polyurethane-polycarbonate-polyol ISM comprising BB15C5 and KTFPB with a polyvinyl pyrrolidone-CARBOSIL® resistance membrane coating; a Ag/AgCl RE as second electrode coated with the same resistance membrane. The data of FIG. 23A shows raw signal of a potassium ion sensor 975 in an in vivo environment and FIG. 23B depicts enlarged section of FIG. 23A demonstrating correlation of blood potassium ion concentration (dots) measured in vivo with the presently disclosed potassium ion sensor 975 and in vitro (blood samples using a bench analyzer (Radiometer ABL90)) measurements 977.

Figure 23C:
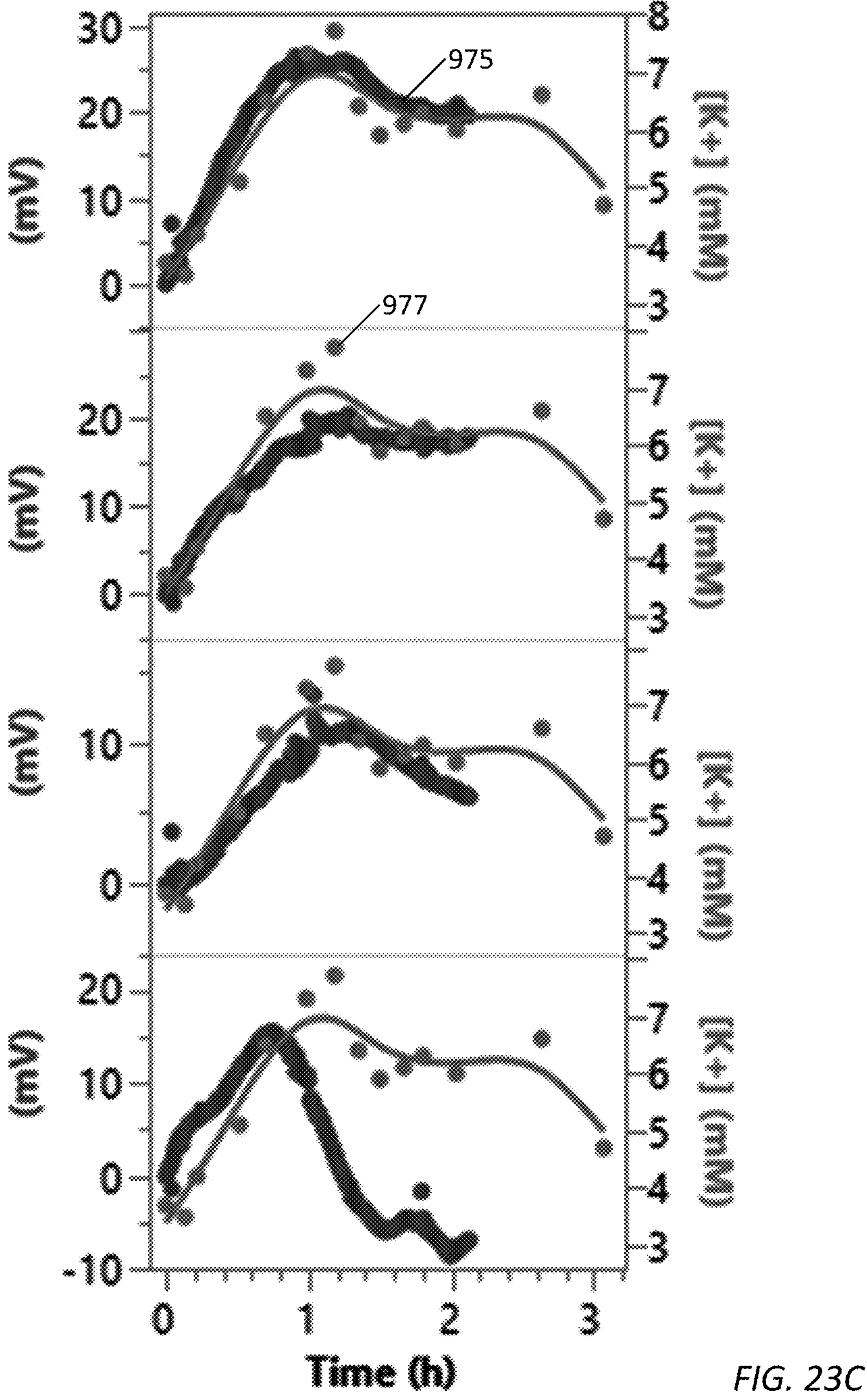

FIG. 23C depicts additional in vivo animal data of another exemplary coaxial potassium ion sensor representative of the present disclosure utilizing a gold wire first electrode with 7102 carbon ink solid contact layer coated with 2-nitrophenyl octyl ether plasticized-PVC ISM comprising BBE44 and KTFPB with a polyvinyl pyrrolidone-CARBOSIL® resistance membrane coating; a Ag/AgCl RE as second electrode coated with the same resistance membrane. The data of FIG. 23C demonstrating correlation of blood potassium ion concentration measured in vivo with the presently disclosed potassium ion sensor and in vitro (blood samples using a bench analyzer (Radiometer ABL90)) measurements.

Sterilization

Figures 24A, 24B:
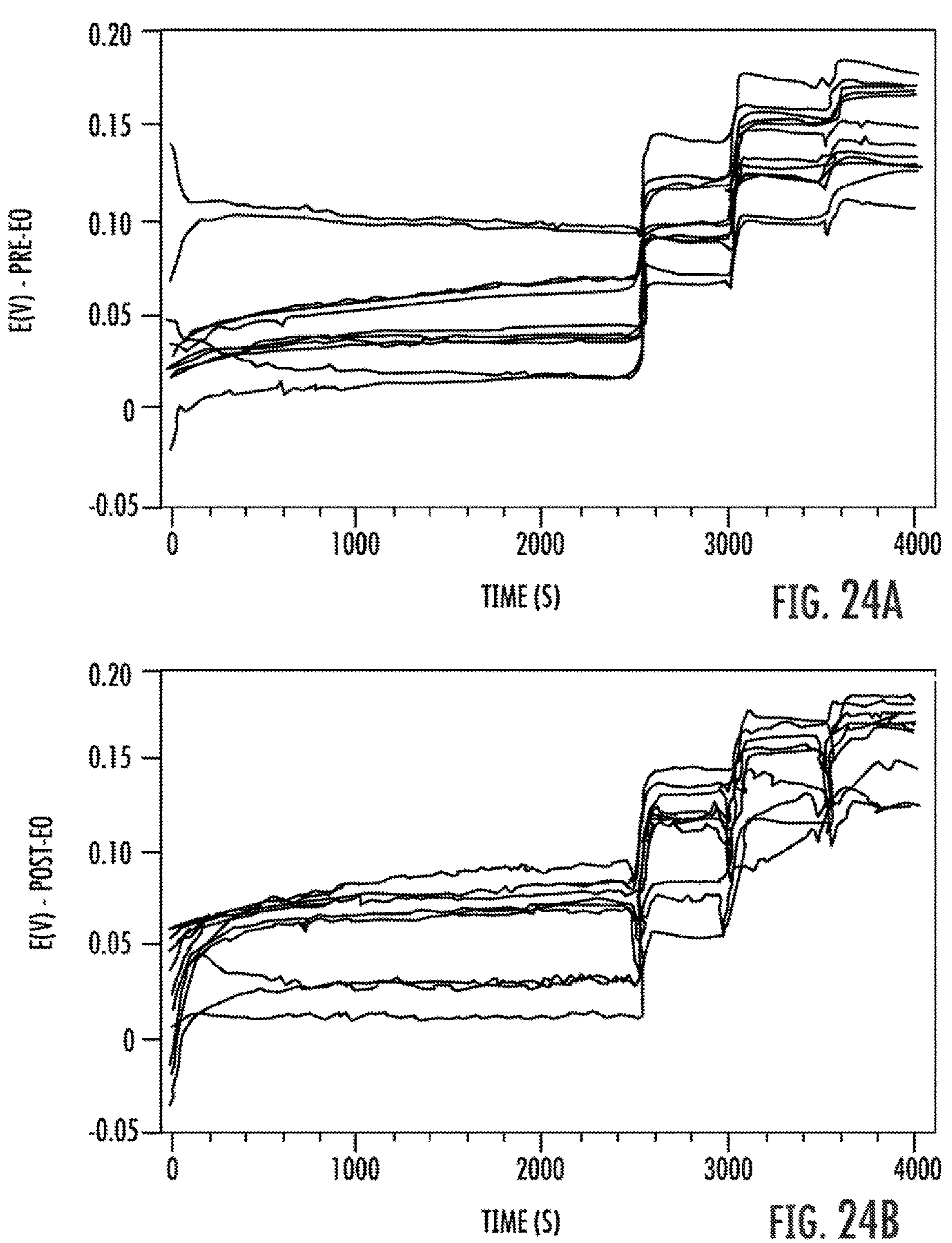
FIGS. 24A and 24B illustrate plots of the measured sensitivity of an example device before and after sterilization.

In one example, exemplary presently disclosed potassium ion sensors are sterilized. In one example, the presently disclosed potassium ion sensors are sterilized with high energy radiation. In one example, the presently disclosed potassium ion sensors are sterilized with ethylene oxide (EtO). FIG. 24A depicts sensitivity and calibration data before EtO sterilization of 23 identically prepared sensors utilizing a gold wire first electrode with 7102 solid contact layer coated with polyurethane-polycarbonate-polyol ISM comprising BBE44 and KTFPB with a polyvinyl pyrrolidone-CARBOSIL® resistance membrane coating; a Ag/AgCl RE as second electrode coated with the same resistance membrane, and FIG. 24B depicts sensitivity and calibration data after EtO sterilization of the sensors. The data of FIGS. 24A and 24B show a significant difference in $E_0$ between untreated and EtO-sterilized sensors (n=23/each). Post-EtO sensors displayed a positive $E_0$ offset and improved distribution as compared to pre-EtO sterilized controls. Microscopic characterization indicated no significant membrane change post-EtO sterilization. Thus, EtO sterilization appears compatible with the presently disclosed sensor chemistry.

Unless indicated otherwise, WE is used as an abbreviation for working electrode throughout this disclosure. Unless indicated otherwise, RE is used as an abbreviation for reference electrode throughout this disclosure.

All references cited herein, including but not limited to published and unpublished applications, patents, and literature references, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material.

The term "comprising" as used herein is synonymous with "including," "containing," or "characterized by," and is inclusive or open-ended and does not exclude additional, unrecited elements or method steps.

All numbers expressing quantities of ingredients, reaction conditions, and so forth used in the specification are to be understood as being modified in all instances by the term "about." Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

The above description discloses several methods and materials of the present disclosure. This disclosure is susceptible to modifications in the methods and materials, as well as alterations in the fabrication methods and equipment. Such modifications will become apparent to those skilled in the art from a consideration of this disclosure or practice of the disclosure disclosed herein. Consequently, it is not intended that this disclosure be limited to the specific examples disclosed herein, but that it covers all modifications and alternatives coming within the true scope and spirit of the disclosure.

While certain examples of the present disclosure have been illustrated with reference to specific combinations of elements, various other combinations may also be provided without departing from the teachings of the present disclosure. Thus, the present disclosure should not be construed as being limited to the particular examples described herein and illustrated in the Figures, but may also encompass combinations of elements of the various illustrated examples and aspects thereof.

What is claimed is:

1. A device for continuously measuring a concentration of at least one target analyte in a biological fluid in vivo, the device comprising:

a transcutaneous analyte sensor configured to be inserted into interstitial fluid, the transcutaneous analyte sensor comprising:

a substrate;

a working electrode disposed directly on the substrate;

a solid contact layer disposed on the working electrode, the solid contact layer comprising a conductive polymer;

an ion-selective membrane comprising an ionophore, the ion-selective membrane disposed directly on the solid contact layer opposite the working electrode and configured to selectively transport the at least one target analyte to or within the working electrode;

a first membrane disposed directly on the ion-selective membrane, the first membrane configured to limit leaching from at least the ion-selective membrane;

a reference electrode disposed directly on the substrate; and a second membrane disposed directly on the reference electrode, the second membrane configured to limit leaching from at least the reference electrode; and sensor electronics coupled to the transcutaneous analyte sensor, the sensor electronics-comprising at least one processor and memory, wherein the at least one processor executes operations comprising:

determining an electromotive force at least partially based on a potential difference that is generated between the working electrode and the reference electrode responsive to the ionophore transporting the at least one target analyte to the working electrode and responsive to the biological fluid conducting an electrophysiological signal to the working electrode, wherein a first contribution to the electromotive force from the electrophysiological signal varies rapidly relative to a second contribution to the electromotive force from the concentration of the at least one target analyte in the biological fluid, and wherein determining the electromotive force further comprises identifying the first contribution and the second contribution;

generating a signal corresponding to the electromotive force; and determining the concentration of the at least one target analyte based at least on the signal.

2. The device of claim 1, wherein the ion-selective membrane is a fluorosilicone rubber, a polydimethylsiloxane polymer, a silicone rubber, a polyurethane with a polysiloxane soft segment, a polyurethane with a hard and soft segment, a water-based polyurethane, polyvinyl butyral, polymethylmethacrylate, polyvinyl acrylate, or blends or graft polymers thereof.

3. The device of claim 1, wherein the working electrode or the reference electrode, independently, is a metal, metal alloy, or conductive polymer selected from the group consisting of poly(3,4-ethylenedioxythiophene) (PEDOT), poly (3,4-ethylenedioxythiophene) polystyrene sulfonate (PEDOT:PSS), polyaniline (PANI), poly(pyrrole) (PPy), and poly(3-octylthiophene) (POT).

4. The device of claim 1, wherein the ionophore is selected from the group consisting of: 4-tert-butylcalix[4]

arene-tetraacetic acid tetraethyl ester (sodium ionophore X); calix[4]arene-25,26,27,28-tetrol (calix[4]arene); potassium ionophore I (valinomycin); potassium ionophore II: bis [(benzo-15-crown-5)-4'-ylmethyl] pimelate (BB15C5); potassium ionophore III: 2-dodecyl-2-methyl-1,3-propanediyl bis[N-[5'-nitro (benzo-15-crown-5)-4'-yl]carbamate] (BME44); 4,5-bis(benzoylthio)-1,3-dithiole-2-thione (Bz2dmit); 1,3,5-Tris[10-(1-adamantyl)-7,9-dioxo-6,10-diazaundecyl]benzene (magnesium ionophore VI); calcium ionophore I (ETH 1001); calcium ionophore II (ETH129); tridodecylmethylammonium chloride (TDMAC); and nonactin.

5. The device of claim 1, the ion-selective membrane further comprising a lipophilic salt selected from the group consisting of sodium tetrakis [3,5-bis(trifluoromethyl)phenyl]borate (NaTPFB), sodium tetraphenylborate (NaTPB), potassium tetrakis [3,5-bis(trifluoromethyl)phenyl]borate (KTFPB), and potassium tetrakis(4-chlorophenyl) borate (KTClPB).

6. The device of claim 1, wherein the at least one target analyte is selected from the group consisting of sodium ion, potassium ion, hydrogen ion, lithium ion, magnesium ion, calcium ion, chloride ion, sulfite ion, sulfate ion, phosphate ion, ammonium ion, uric acid, urea, ketone, and glucose.

7. The device of claim 1, further comprising a biointerface membrane disposed on the ionophore and the working electrode, wherein the biointerface membrane comprises a polymer selected from the group consisting of polyvinyl butyral (PVB), polyurethane, and silicone.

8. The device of claim 1, further configured to release a therapeutic compound into the biological fluid.

9. The device of claim 1, wherein the sensor electronics comprises a galvanostat.

10. The device of claim 1, wherein the sensor electronics is configured to: (a) measure the electromotive force with a dynamically configurable frequency; (b) maintain the reference electrode at a substantially constant potential; or (c) combinations thereof.

11. The device of claim 1, wherein the electrophysiological signal comprises a cardiac electrical signal.

12. The device of claim 1, further comprising an enzyme configured to generate a target ion responsive to acting upon the at least one target analyte, wherein the enzyme is selected from an oxidase.

13. The device of claim 1, wherein the sensor electronics further comprises an amplifier.

14. A method for continuously measuring a concentration of a target analyte in a biological fluid in vivo, the method comprising:

generating, via a transcutaneous analyte sensor configured to be inserted into interstitial fluid, a signal corresponding to an electromotive force, wherein the transcutaneous analyte sensor comprises:

a substrate;

a working electrode disposed on the substrate;

a solid contact layer disposed on the working electrode, the solid contact layer comprising a conductive polymer;

an ionophore disposed on the solid contact layer opposite the working electrode and configured to selectively transport a target ion to or within the working electrode;

a first membrane disposed over the ionophore opposite the solid contact layer, the first membrane configured to limit leaching from the working electrode;

a reference electrode disposed on the substrate; and a second membrane disposed on the reference electrode, the second membrane configured to limit leaching from at least the reference electrode, wherein the electromotive force is at least partially based on a potential difference that is generated between the working electrode and the reference electrode responsive to the ionophore transporting the target ion to the working electrode and responsive to the biological fluid conducting an electrophysiological signal to the working electrode, wherein a first contribution to the electromotive force from the electrophysiological signal varies rapidly relative to a second contribution to the electromotive force from the concentration of the target analyte in the biological fluid, and wherein generating the signal corresponding to the electromotive force further comprises identifying the first contribution and the second contribution; and determining the concentration of the target analyte in the biological fluid in vivo based at least on the signal.

15. The method of claim 14, further comprising an enzyme configured to generate the target ion.

* * * * *